US012790323B2

(12) United States Patent
Hsieh et al.

(10) Patent No.: US 12,790,323 B2
(45) Date of Patent: Nov. 10, 2026

(54) CDK19-SELECTIVE INHIBITORS, AND METHODS OF USE THEREOF

(71) Applicants: CZ BIOHUB SF, LLC, San Francisco, CA (US); THE BOARD OF TRUSTEES OF THE LELAND STANFORD JUNIOR UNIVERSITY, Stanford, CA (US)

(72) Inventors: Robert W. Hsieh, Stanford, CA (US); Mark Smith, Stanford, CA (US); Michael F. Clarke, Stanford, CA (US); Vincent Alford, Stanford, CA (US); Andre Henri St. Amant, Stanford, CA (US); Angera Hsiao-Chi Kuo, Foster City, CA (US)

(73) Assignees: THE BOARD OF TRUSTEES OF THE LELAND STANFORD JUNIOR UNIVERSITY, Stanford, CA (US); CZ BIOHUB SF, LLC, San Francisco, CA (US)

( * ) Notice: Subject to any disclaimer, the term of this patent is extended or adjusted under 35 U.S.C. 154(b) by 764 days.

(21) Appl. No.: 18/040,122

(22) PCT Filed: Jul. 30, 2021

(86) PCT No.: PCT/US2021/043896
§ 371 (c)(1),
(2) Date: Jan. 31, 2023

(87) PCT Pub. No.: WO2022/026823
PCT Pub. Date: Feb. 3, 2022

(65) Prior Publication Data

US 2024/0270735 A1 Aug. 15, 2024

Related U.S. Application Data

(60) Provisional application No. 62/706,119, filed on Jul. 31, 2020.

(51) Int. Cl.

| | |
|---|---|
| ***C07D 417/04*** | (2006.01) |
| ***A61K 31/4439*** | (2006.01) |
| ***A61K 45/06*** | (2006.01) |
| ***A61P 35/00*** | (2006.01) |
| ***C07D 249/14*** | (2006.01) |
| ***C07D 263/48*** | (2006.01) |
| ***C07D 271/113*** | (2006.01) |
| ***C07D 277/48*** | (2006.01) |
| ***C07D 285/135*** | (2006.01) |
| ***C07D 413/04*** | (2006.01) |
| ***C07D 417/06*** | (2006.01) |
| ***C07D 417/10*** | (2006.01) |
| ***C07D 417/14*** | (2006.01) |

(52) U.S. Cl.
CPC ........ *C07D 417/04* (2013.01); *A61K 31/4439* (2013.01); *A61K 45/06* (2013.01); *A61P 35/00* (2018.01); *C07D 249/14* (2013.01); *C07D 263/48* (2013.01); *C07D 271/113* (2013.01); *C07D 277/48* (2013.01); *C07D 285/135* (2013.01); *C07D 413/04* (2013.01); *C07D 417/06* (2013.01); *C07D 417/10* (2013.01); *C07D 417/14* (2013.01)

(58) Field of Classification Search
None
See application file for complete search history.

(56) References Cited

U.S. PATENT DOCUMENTS

2007/0197532 A1 8/2007 Cao et al.

FOREIGN PATENT DOCUMENTS

WO 99/28309 A1 6/1999

OTHER PUBLICATIONS

Rosenthal et al. ((2013), Synthesis and SAR studies of 5-(pyridin-4-yl)-1,3,4-thiadiazol-2-amine derivatives as potent inhibitors of Bloom helicase, Bioorg. Med. Chem. Lett., 23, 5660-5666) (Year: 2013).*
Lima et al. ((2005), Bioisosterism: A Useful Strategy for Molecular Modification and Drug Design, 12, 23-49) (Year: 2005).*
Wu et al., Automated microfluidic chromatin immunoprecipitation from 2,000 cells, Lab. Chip., 9(10):1365-1370 (2009).
Wu et al., Quantitative assessment of single-cell rnA-sequencing methods, Nat. Methods., 11(1):41-6 (2014).

(Continued)

*Primary Examiner* — Juliet C Switzer
*Assistant Examiner* — Dawanna Shar-Day White
(74) *Attorney, Agent, or Firm* — MARSHALL, GERSTEIN & BORUN LLP

(57) ABSTRACT

Provided herein are compounds or pharmaceutically acceptable salts thereof, having a structure of formula (I): wherein substituents are as described herein. Also provided is a pharmaceutical composition comprising a compound or pharmaceutically acceptable salt having a structure of formula (I). Further provided are a method of inhibiting cyclin dependent kinase 19 (CDK19) a method of treating cancer (e.g., breast cancer) with the disclosed compounds.

(I)

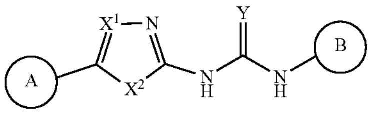

1 Claim, 1 Drawing Sheet

(56) References Cited

OTHER PUBLICATIONS

Zarnegar et al., Targeted chromatin ligation, a robust epigenetic profiling technique for small cell Nos., Nucleic Acids. Res., 5(17):e153 (2017).
Adorno et al., Usp16 contributes to somatic stem-cell defects in Down's syndrome, Nat., 501(7467):380-4 (2013).
Akala et al., Long-term haematopoietic reconstitution by Trp532/2p16Ink4a2/2p19Arf2/2 multipotent progenitors, Nat., 453(7192):228-32 (2008).
Al-Hajj et al., Prospective identification of tumorigenic breast cancer cells, Proc. Natl. Acad. Sci. U. S. A., 100(7):3983-3988 (2003).
Audetat et al., A Kinase-Independent Role for Cyclin-Dependent Kinase 19 in p53 Response, Mol. Cell Biol., 37(13): e00626-16 (2017).
Bockhorn et al., MicroRNA-30c targets cytoskeleton genes involved in breast cancer cell invasion, Breast Cancer Res. Treat., 137(2):373-382 (2013).
Broude et al., Expression of CDK8 and CDK8-interacting Genes as Potential Biomarkers in Breast Cancer, Curr. Cancer Drug Targ., 15(8):739-749 (2015).
Brown et al., The International Mouse Phenotyping Consortium: past and future perspectives on mouse phenotyping, Mamm Gen., 23(9-10):632-640 (2012).
Cai et al., A Quiescent Bcl11b High Stem Cell Population Is Required for Maintenance of the Mammary Gland, Cell Stem Cell., 20(2):247-260 (2017).
Chen et al., CDK8/19 Mediator kinases potentiate induction of transcription by NF?B, Proc. Natl. Acad. Sci. U. S. A. 114(38):10208-10213 (2017).
Chen et al., KIT Signaling Promotes Growth of Colon Xenograft Tumors in Mice and Is Up-Regulated in a Subset of Human Colon Cancers, Gastroent., 149(3):705-717 (2015).
Chio et al., NRF2 Promotes Tumor Maintenance by Modulating mRNA Translation in Pancreatic Cancer, Cell, 166(4):963-976 (2016).
Cho et al., Isolation and Molecular Characterization of Cancer Stem Cells in MMTV-Wnt-1 Murine Breast Tumors, Stem Cells., 26(2):364-371 (2008).
Clarke et al., Assessing the mechanism and therapeutic potential of modulators of the human Mediator complex-associated protein kinases, Elife, 5:e20722 (2016).
Consortium, Genetic effects on gene expression across human tissues, Nat., 550(7675):204-213 (2017).
Consortium, Single-cell transcriptomics of 20 mouse organs creates a Tabula Muris, Nat., 562(7727): 367-372 (2018).
Dalerba et al., CDX2 as a Prognostic Biomarker in Stage II and Stage III Colon Cancer, N. Engl. J. Med., 374(3): 211-222 (2016).
Dalerba et al., Single-cell dissection of transcriptional heterogeneity in human colon tumors, Nat. Biotechnol., 29(12):1120-1127 (2011).
Derose et al., Tumor grafts derived from women with breast cancer authentically reflect tumor pathology, growth, metastasis and disease outcomes, Nat Med., 17(11):1514 (2011).
Diehn et al., Association of reactive oxygen species levels and radioresistance in cancer stem cells, Nat., 458(7239):780-783 (2009).
Dinardo et al., Venetoclax combined with decitabine or azacitidine in treatment-naive, elderly patients with acute myeloid leukemia, Blood., 133(1):7-17 (2019).
Galbraith et al., CDK8: a positive regulator of transcription, Transcr., 1(1):4-12 (2010).
Gulati et al., Single-cell transcriptional diversity is a hallmark of developmental potential, Scien., 367(6476):405-411 (2020).
International Application No. CT/US2021/043896, Invitation to Pay Additional Fees, mailed Oct. 19, 2021.
International Application No. PCT/US2021/043896, International Preliminary Report on Patentability, mailed Feb. 9, 2023.
International Application No. PCT/US2021/043896, International Search Report and Written Opinion, mailed Dec. 30, 2021.
Isobe et al., miR-142 regulates the tumorigenicity of human breast cancer stem cells through the canonical WNT signaling pathway, Elife., 18;3:e01977 (2014).
Jiang et al., Ferroptosis as a p53-mediated activity during tumour suppression, Nat., 520(7545):57-62 (2015).
Johannessen et al., Small-molecule studies identify Cd K8 as regulator of IL-10 in myeloid cells, Nat. Chem. Biol., 13(10):1102-1108 (2017).
Kalimutho et al., Targeted Therapies for Triple-Negative Breast Cancer: Combating a Stubborn Disease, Trends. Pharmacol. Sci., 36(12):822-846 (2015).
Li et al., Identification of Pancreatic Cancer Stem Cells, Cancer Res., 67(3):1030-7 (2007).
Liberzon, The Molecular Signatures Database Hallmark Gene Set Collection, Cell Syst., 1(6):417-425 (2015).
Liu et al., Analysis of gene expression and chemoresistance of CD133+ cancer stem cells in glioblastoma, Mol. Cancer., 5(67):10.1186/1476-4598-5-67 (2006).
Liu et al., Cancer stem cells from human breast tumors are involved in spontaneous metastases in orthotopic mouse models, Proc. Natl. Acad. Sci., 107(42):18115-20 (2010).
Liu et al., The Prognostic Role of a Gene Signature from Tumorigenic Breast-Cancer Cells, N. Engl. J. Med., 356(3):217-26 (2007).
Molofsky et al., Bmi-1 dependence distinguishes neural stem cell self-renewal from progenitor proliferation, Nat., 425(6961):962-967 (2003).
Morrison et al., A Genetic Determinant That Specifically Regulates the Frequency of Hematopoietic Stem Cells, J. Immunol., 168(2):635-42 (2002).
Network et al., The Cancer Genome Atlas Pan-Cancer analysis project, Nat. Genet., 45(10):1113-20 (2013).
Oshimori et al., TGF-b Promotes Heterogeneity and Drug Resistance in Squamous Cell Carcinoma, Cell, 160(5):963-976 (2015,).
Parashurama et al., Remodeling of Endogenous Mammary Epithelium by Breast Cancer Stem Cells, 30(10):2114-27 (2012).
Park et al., Bmi-1 is required for maintenance of adult self-renewing haematopoietic stem cells, Nat., 423(6937):302-5 (2023).
Park et al., Molecular Cloning and Characterization of a Novel Regulator of G-protein Signaling from Mouse Hematopoietic Stem Cells, J. Biol. Chem., 276(2):915-23 (2001).
Pollyea et al., Venetoclax with azacitidine disrupts energy metabolism and targets leukemia stem cells in patients with acute myeloid leukemia, Nat. Med., 24(12):1859-1866 (2018).
Porter et al., Cyclin-dependent kinase 8 mediates chemotherapy induced tumor-promoting paracrine activities, Proc. Natl. Acad. Sci., 109(34):13799-804 (2012).
Prince et al., Identification of a subpopulation of cells with cancer stem cell properties in head and neck squamous cell carcinoma, Proc. Natl. Acad. Sci., 104(3):973-8 (2007).
Rothenberg et al., Identification of a cKit! Colonic Crypt Base Secretory Cell That Supports Lgr5+ Stem Cells in Mice, Gastroe., 142(5):1195-1205 (2012).
Scheeren et al., A cell-intrinsic role for TLR2-MYD88 in intestinal and breast epithelia and oncogenesis, Nat. Cell Biol., 16(12):1238-48 (2014).
Shimono et al., Downregulation of miRNA-200c Links Breast Cancer Stem Cells with Normal Stem Cells, Cell, 138(3):592-603 (2009).
Sikander et al., Role of epithelial to mesenchymal transition associated genes in mammary gland regeneration and breast tumorigenesis, Nat. Commun., 8(1):1669 (2017).
Subramaniana et al., Gene set enrichment analysis: A knowledge-based approach for interpreting genome-wide expression profiles, Proc. Natl. Acad. Sci., 102(43):15545-50 (2005).
Willinghama et al., The CD47-signal regulatory protein alpha (SIRPa) interaction is a therapeutic target for human solid tumors, Proc. Natl. Acad. Sci., 109(17):6662-6667 (2012).

* cited by examiner

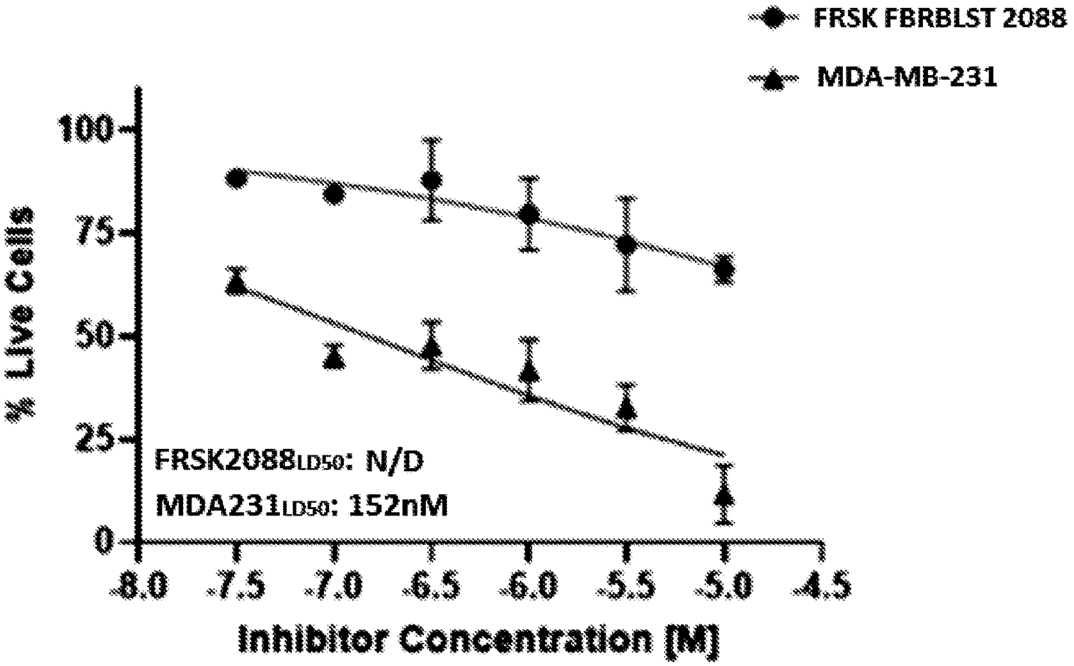
FRSK FBRBLST 2088
MDA-MB-231
100
75
50
25
0
% Live Cells
-8.0
-7.5
-7.0
-6.5
-6.0
-5.5
-5.0
-4.5
Inhibitor Concentration [M]
FRSK2088LD50: N/D
MDA231LD50: 152nM

CDK19-SELECTIVE INHIBITORS, AND METHODS OF USE THEREOF

STATEMENT OF GOVERNMENT INTEREST

This invention was made with Government support under contract W81XWH-13-1-0281 awarded by the Department of Defense. The Government has certain rights in the invention.

BACKGROUND

Although the survival rate of breast cancer patients has improved over the past 30 years, breast cancer still remains the leading cause of cancer-related death among women worldwide. This decrease in patient mortality rates can be primarily attributed to early cancer detection methods such as routinely administered mammograms and screening of genetic biomarkers associated within high risk patient populations. Unfortunately, scientific advancements in targeted therapeutic strategies have proven more difficult to achieve. For example, target-specific therapies such as tamoxifen and Herceptin display efficacy in more commonly diagnosed breast cancer cases yet have shown to be completely ineffective in treating a subset of patients diagnosed with triple-negative breast cancer (TNBC). TNBC is an aggressive, invasive breast cancer subtype that is characterized as estrogen receptor (ER) negative, progesterone receptor (PR) negative, and HER2-negative, that is, a "triple-negative" phenotype. For this reason, the only therapeutic intervention left available to these patients is chemotherapy, which is known to be non-specific and highly cytotoxic. For example, current strategies for treating TNBC include inhibiting transcriptional co-factors and targeting cancer stem cells, of which both approaches are limited by toxicity. Accordingly, patients diagnosed with TNBC often experience worse survival outcomes than non-TNBCs (median survival 9 months vs 22 months, respectively).

Cyclin dependent kinase 19 (CDK19), and a related isoform CDK8, are oncogenic transcription-regulating kinases that play a role in certain cancers, including TNBC. Other cancers include, but are not limited to, prostate cancer, cancer of the gastrointestinal tract (e.g., colorectal cancer), bladder cancer, sarcoma, cervical cancer, esophageal adenocarcinoma, acute myeloid leukemia, melanoma, glioma, and ovarian cancer. Compounds that non-selectively inhibit CDK19 and CDK8 have been explored for their anticancer properties, but have shown to have undesired side effects due to the CDK8 inhibition. Inhibition of CDK8 typically leads to greater side-effects due to its wider tissue distribution as compared to CDK19. For example, compounds that inhibit CDK8 typically result in greater gastrointestinal side-effects owing to the relatively high expression of CDK8 in the colon. It is believed that compounds that selectively inhibit CDK19 would result in a greater therapeutic index and would have less systemic toxicity.

In view of the foregoing, there remains a need for compounds that selectively inhibit CDK19 over CDK8, as well as new methods of treating cancer, such as TNBC, which comprising administering these compounds.

SUMMARY

The disclosure provides compounds of formula (I), as described herein, or pharmaceutically acceptable salts thereof, and their use as inhibitors of CDK19,

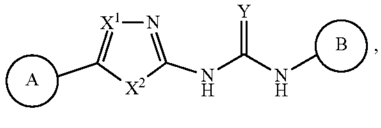
(I)

wherein:

ring A comprises a $C_6$-$C_{10}$aryl, a $C_3$-$C_{10}$cycloalkyl, a $C_5$-$C_{10}$heterocycloalkyl having 1-4 ring heteroatoms independently selected from N, O, S, or a 5-10 membered heteroaryl having 1-4 ring heteroatoms selected from N, O, and S, and ring A is optionally substituted with 1-2 $R^A$;

ring B comprises a $C_6$-$C_{10}$aryl or a 5-10 membered heteroaryl having 1-4 ring heteroatoms selected from N, O, and S, and ring B is optionally substituted with 1-3 $R^B$;

each $R^A$ is independently selected from the group consisting of $C_1$-$C_6$alkyl, $C_1$-$C_6$haloalkyl, $C_3$-$C_6$cycloalkyl, $C_1$-$C_6$alkoxy, $C_1$-$C_6$haloalkoxy, $C_1$-$C_3$alkylene-$C_6$-$C_{10}$aryl, cyano, halo, nitro,

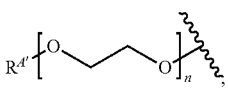
, $C_1$-$C_3$alkylene-$C_5$-$C_{10}$heterocycloalkyl having 1-4 ring heteroatoms independently selected from N, O, S, and a 5-10 membered cycloheteroalkyl having 1-4 heteroatoms selected from N, O, and S;

$R^{A'}$ is $C_1$-$C_3$alkyl;

n is 1-5;

each $R^B$ is independently selected from the group consisting of $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_3$-$C_6$cycloalkoxy, $C_1$-$C_3$alkylene-$C_3$-$C_6$cycloalkyl, $C_1$-$C_3$alkylene-$C_6$-$C_{10}$aryl, —O—$C_1$-$C_3$alkylene-$C_6$-$C_{10}$aryl, —O—$C_1$-$C_3$alkylene-$C_1$-$C_6$alkoxy, —C(O)O$R^{B'}$, —S$R^{B'}$, —C(Z)$C_1$-$C_6$haloalkyl, —CN, nitro, halo, —$C_1$-$C_3$alkylene-O$R^{B'}$, —$C_1$-$C_3$alkylene-$C_6$-$C_{10}$heterocycloalkyl having 1-4 ring hetereoatoms independently selected from N, O, S, and —$C_1$-$C_3$alkylene-$C_5$-$C_6$heteroaryl having 1-4 ring heteroatoms independently selected from N, O, S;

or two ortho $R^B$ taken together with the atoms to which they are attached form a 5 or 6 membered cycloalkyl or a 5 or 6 membered cycloheteroalkyl comprising 1-3 ring heteroatoms independently selected from N, O, S;

$R^{B'}$ is H, $C_1$-$C_3$alkyl, or $C_1$-$C_6$haloalkyl;

Z is O or S;

$X^1$ is N or $CR^1$, and $R^1$ is H or $C_1$-$C_6$alkyl;

$X^2$ is NH, O, or S;

Y is O or S; and with the proviso that (a) when ring A is unsubstituted 4-pyridinyl, Y is O, and $X^1$ is N and $X^2$ is S, ring B is not: phenyl, 2-fluorophenyl, 2-chlorophenyl, 2-methoxyphenyl, 3-fluorophenyl, 3-chlorophenyl, 3-cyanophenyl, 3-methylphenyl, 3-methoxyphenyl, 3,4-difluorophenyl, 4-methylphenyl, 4-cyanophenyl, 4-methoxyphenyl, 4-ethoxyphenyl, 4-bromophenyl, 4-chlorophenyl, 4-fluorophenyl, 4-tert-butylphenyl, 2,3-dichlorophenyl, 2,4-dichlorophenyl, 2,4-difluorophenyl, 2,5-dimethoxyphenyl, 3,4-dimethylphenyl, 3,4-dichlorophenyl, 3,4-dibromophenyl, 3,4-difluorophenyl, 3-chloro-4-cyanophenyl, 3-bromo-4-cyanophenyl, 3-cyano-4-fluorophenyl, 3-fluoro-4-(trifluoromethyl)phenyl, 4-bromo-3-cyanophenyl, 4-bromo-3-methylphenyl, 4-bromo-3-(trifluoromethyl)phenyl, 4-chloro-3-cyano-phenyl, 4-chloro-3-methylphenyl, 4-chloro-3-(trifluoromethyl)phenyl, 4-cyano-3-methylphenyl, 4-cyano-3-(trifluoromethyl)phenyl, 4-fluoro-3-(trifluoromethyl) phenyl, or 5-chloro-2-methoxyphenyl;

(b) when ring A is unsubstituted 4-pyridinyl, Y is O, and $X^1$ is CH and $X^2$ is S, ring B is not: 3,4-dichlorophenyl or 2-chlorophenyl; and (c) when ring A is unsubstituted 3-pyridinyl, Y is O, and $X^1$ is N and $X^2$ is S, ring B is not: phenyl, 2-chloro-phenyl, 2-fluorophenyl, 3-methylphenyl, 4-methylphenyl, 4-isopropylphenyl, 4-methoxyphenyl, 4-chloro-phenyl, 4-bromophenyl, 4-fluorophenyl, 2,3-dichlorophenyl, 2,4-dimethylphenyl, 3,4-dimethylphenyl, 3,4-dichlorophenyl, 3-chloro-4-fluorophenyl, or naphthyl.

The disclosure also provides pharmaceutical compositions comprising a compound, or pharmaceutically acceptable salt thereof, as disclosed herein, and methods of using the disclosed compounds, such as methods of inhibiting CDK19, and methods of treating cancer, including breast cancer (e.g., triple negative breast cancer).

BRIEF DESCRIPTION OF THE FIGURES

FIG. 1 shows results of lethal dose studies of Compound A133 in triple negative breast cancer (TNBC) cells (MDA-MB-231) and normal fibroblast cells. Normal human fibroblast cells (red line) and TNBC cells (blue) blue line were treated with various concentrations of Compound A133 and live cell counts were performed and plotted to determine a $LD_{50}$.

DETAILED DESCRIPTION

The compounds disclosed herein are inhibitors of CDK19. Inhibition of CDK19 has been shown to be effective against breast cancer, such as triple negative breast cancer. In some embodiments, the disclosed compounds inhibit CDK19 selectively over CDK8, which is a structurally similar CDK but is much more prevalent throughout the body and can lead to many undesired effects, due to its wider tissue distribution as compared to CDK19. In particular, CDK8 inhibition has been shown to have high incidences of gastrointestinal side effects due to the high levels of CDK8 in the colon.

The disclosed compounds bind to and inhibit the activity of CDK19. In some embodiments, the disclosed compounds selectively inhibit CDK19 over CDK8. The compounds disclosed herein can selectively inhibit CDK19 over the isoform CDK8 such that such side effects due to CDK8 inhibition are minimized or avoided, compared to other CDK19 inhibitors.

Compounds of the Disclosure

Provided herein are compounds, or pharmaceutically acceptable salts thereof, that have a structure of formula (I):

(I)

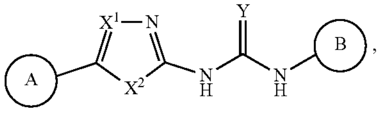

wherein:

ring A comprises a $C_6$-$C_{10}$aryl, a $C_3$-$C_{10}$cycloalkyl, a $C_5$-$C_{10}$heterocycloalkyl having 1-4 ring heteroatoms independently selected from N, O, S, or a 5-10 membered heteroaryl having 1-4 ring heteroatoms selected from N, O, and S, and ring A is optionally substituted with 1-2 $R^A$;

ring B comprises a $C_6$-$C_{10}$aryl or a 5-10 membered heteroaryl having 1-4 ring heteroatoms selected from N, O, and S, and ring B is optionally substituted with 1-3 $R^B$;

each $R^A$ is independently selected from the group consisting of $C_1$-$C_6$alkyl, $C_1$-$C_6$haloalkyl, $C_3$-$C_6$cycloalkyl, $C_1$-$C_6$alkoxy, $C_1$-$C_6$haloalkoxy, $C_1$-$C_3$alkylene-$C_6$-$C_{10}$aryl, cyano, halo, nitro,

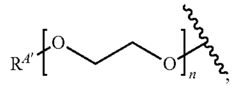

$C_1$-$C_3$alkylene-$C_5$-$C_{10}$heterocycloalkyl having 1-4 ring heteroatoms independently selected from N, O, S, and a 5-10 membered cycloheteroalkyl having 1-4 heteroatoms selected from N, O, and S;

$R^{A'}$ is $C_1$-$C_3$alky;

n is 1-5;

each $R^B$ is independently selected from the group consisting of $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_3$-$C_6$cycloalkoxy, $C_1$-$C_3$alkylene-$C_3$-$C_6$cycloalkyl, $C_1$-$C_3$alkylene-$C_6$-$C_{10}$aryl, —O—$C_1$-$C_3$alkylene-$C_6$-$C_{10}$aryl, —O—$C_1$-$C_3$alkylene-$C_1$-$C_6$alkoxy, —C(O)$OR^{B'}$, —$SR^{B'}$, —C(Z)$C_1$-$C_3$haloalkyl, —CN, nitro, halo, —$C_1$-$C_3$alkylene-$OR^{B'}$, —$C_1$-$C_3$alkylene-$C_6$-$C_{10}$heterocycloalkyl having 1-4 ring hetereoatoms independently selected from N, O, S, and —$C_1$-$C_3$alkylene-$C_5$-$C_6$heteroaryl having 1-4 ring heteroatoms independently selected from N, O, S;

or two ortho $R^B$ taken together with the atoms to which they are attached form a 5 or 6 membered cycloalkyl or a 5 or 6 membered cycloheteroalkyl comprising 1-3 ring heteroatoms independently selected from N, O, S;

$R^{B'}$ is H, $C_1$-$C_6$alkyl, or $C_1$-$C_6$haloalkyl;

Z is O or S;

$X^1$ is N or $CR^1$, and $R^1$ is H or $C_1$-$C_6$alkyl;

$X^2$ is NH, O, or S;

Y is O or S; and with the proviso that (a) when ring A is unsubstituted 4-pyridinyl, Y is O, and $X^1$ is N and $X^2$ is S, ring B is not: phenyl, 2-fluoro-phenyl, 2-chlorophenyl, 2-methoxyphenyl, 3-fluoro-phenyl, 3-chlorophenyl, 3-cyanophenyl, 3-methylphenyl, 3-methoxyphenyl, 4-methylphenyl, 4-cyanophenyl, 4-methoxyphenyl, 4-ethoxyphenyl, 4-bromophenyl, 4-chlorophenyl, 4-fluorophenyl, 4-tert-butylphenyl, 2,3-dichlorophenyl, 2,4-dichloro-phenyl, 2,4-difluorophenyl, 2,5-dimethoxyphenyl, 3,4-dimethylphenyl, 3,4-dichlorophenyl, 3,4-dibromophenyl, 3,4-difluorophenyl, 3-chloro-4-cyanophenyl, 3-bromo-4-cyanophenyl, 3-cyano-4-fluorophenyl, 3-fluoro-4-(trifluoromethyl)phenyl, 4-bromo-3-cyanophenyl, 4-bromo-3-methylphenyl, 4-bromo-3-(trifluoromethyl)phenyl, 4-chloro-3-cyanophenyl, 4-chloro-3-methylphenyl, 4-chloro-3-(trifluoromethyl)phenyl, 4-cyano-3-methylphenyl, 4-cyano-3-(trifluoromethyl)phenyl, 4-fluoro-3-(trifluoromethyl)phenyl, or 5-chloro-2-methoxyphenyl, (b) when ring A is unsubstituted 4-pyridinyl, Y is O, and $X^1$ is CH and $X^2$ is S, ring B is not: 3,4-dichlorophenyl or 2-chlorophenyl, and (c) when ring A is unsubstituted 3-pyridinyl, Y is O, and $X^1$ is N and $X^2$ is S, ring B is not: phenyl, 2-chlorophenyl, 2-fluorophenyl, 3-methylphenyl, 4-methylphenyl, 4-isopropylphenyl, 4-methoxyphenyl, 4-chlorophenyl, 4-bromophenyl, 4-fluorophenyl, 2,3-dichlorophenyl, 2,4-dimethylphenyl, 3,4-dimethylphenyl, 3,4-dichlorophenyl, 3-chloro-4-fluorophenyl, or naphthyl.

The compounds disclosed herein include all pharmaceutically acceptable isotopically-labeled compounds wherein one or more atoms of the compounds disclosed herein are replaced by atoms having the same atomic number, but an atomic mass or mass number different from the atomic mass or mass number usually found in nature, examples of which include isotopes of hydrogen, such as 2H and 3H. In some cases, one or more hydrogen atoms of the compounds disclosed herein are specifically deuterium (2H).

It is understood that, in any compound disclosed herein having one or more chiral centers, if an absolute stereochemistry is not expressly indicated, then each center may independently be of (R)-configuration or (s)-configuration or a mixture thereof. Thus, a compound provided herein may be contain substantially (e.g., at least 90%, or at least 95%) a single enantiomer, or be a mixture, e.g., a mixture of enantiomers and/or diastereomers. Further, compounds provided herein may be racemic mixtures. In addition, it is understood that in any compound having one or more double bond(s) generating geometrical isomers that can be defined as (E) or (Z) each double bond may independently be (E) or (z) or a mixture thereof. Likewise, a compound shown as a specific tautomer is meant to embrace all tautomeric forms of that compound.

The term "alkyl" as used herein means a saturated straight or branched chain hydrocarbon. The term "cycloalkyl" refers to a non-aromatic carbon only containing ring system which is saturated, having three to 10 carbon atoms (e.g., three to six ring carbon atoms). Examples of $C_1$-$C_6$ alkyl groups include but are not limited to methyl, ethyl, isopropyl, n-propyl, isobutyl, n-butyl, sec-butyl, tert-butyl, isopentyl, n-pentyl, neopentyl, sec-pentyl, 3-pentyl, sec-isopentyl, active pentyl, isohexyl, n-hexyl, sec-hexyl, neohexyl, and tert-hexyl. Contemplated cycloalkyl groups include cyclopropyl, cyclobutyl, cyclopentyl, and cyclohexyl. An illustrative $C_{10}$ cycloalkyl group is the bicyclic adamantyl group. An alkylene group is an alkyl group that is further substituted. For example, "alkylene-cycloalkyl" refers to an alkyl group substituted with a cycloalkyl group.

The term "haloalkyl" refers to an alkyl substituted with one or more halogen atoms. This term includes perfluorinated alkyl groups, such as $—CF_3$ and $—CF_2CF_3$.

The term "alkoxy" refers to an —O-alkyl group wherein the moiety is attached through an oxygen atom.

The term "haloalkoxy" refers to an alkoxy group substituted with one or more halogen atoms. This term includes perfluorinated alkoxy groups, such as $—OCF_3$ and $—OCF_2CF_3$.

As used herein, the term "cyano" refers to —CN.

As used herein, the term "aryl" refers to a monocyclic or bicyclic aromatic group having 6 to 10 ring carbons. Aryl groups can be isolated (e.g., phenyl) or fused to another aryl group (e.g., naphthyl), or a cycloalkyl group (e.g. tetrahydronaphthyl). The aryl ring can be substituted as disclosed herein or unsubstituted.

As used herein, the term "heteroaryl", refers to ring having five to ten (5-10) members of which 1 to 4 (or 1 to 3) ring atoms are heteroatoms selected from N, O, and S, including monocyclic heteroaromatic rings and polycyclic aromatic rings in which a monocyclic aromatic ring is fused to one or more other aromatic ring.

Examples of heteroaryl groups include, but are not limited to, pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

Ring A and $R^A$

In some embodiments, ring A comprises a 5-10 membered heteroaryl having 1-3 ring heteroatoms selected from N, O, and S, wherein ring A is optionally substituted with 1-2 $R^A$. In some embodiments, ring A is selected from the group consisting of 3-methyl-4-pyridinyl, 3-ethyl-4-pyridinyl, 3-isopropyl-4-pyridinyl, 3-cyclopropyl-4-pyridinyl, 3,5-dimethyl-4-pyridinyl, 5-methyl-3-pyridinyl, 4-methyl-3-pyridinyl, and 5-chloro-3-pyridinyl.

In some embodiments, ring A comprises pyridinyl optionally substituted with 1-2 $R^A$. In some cases, ring A is substituted pyridinyl. In some embodiments, the pyridinyl comprises a 3-pyridinyl, which may be substituted or unsubstituted. In some embodiments, the pyridinyl comprises a 4-pyridinyl, which may be substituted or unsubstituted.

In some embodiments, ring A comprises quinolinyl (e.g., 4-quinolinyl and 8-quinolinyl).

In some embodiments, ring A comprises a $C_6$-$C_{10}$aryl. Suitable nonlimiting examples of $C_6$-$C_{10}$aryl ring A include phenyl and furanyl.

In some embodiments, ring A comprises a $C_3$-$C_{10}$cycloalkyl. Suitable non limiting examples of $C_3$-$C_{10}$cycloalkyl ring A include cyclopropyl and cyclohexyl. Moreover, in some embodiments the $C_3$-$C_{10}$cycloalkyl ring A is adamantly.

In some embodiments, ring A comprises a $C_5$-$C_{10}$heterocycloalkyl having 1-4 ring heteroatoms independently selected from N, O, S. Suitable non limiting examples of $C_5$-$C_{10}$heterocycloalkyl ring A include morpholinyl and tetrahydrofuranyl.

In some embodiments, in conjunction with other above or below embodiments, ring A is optionally substituted with 1 or 2 $R^A$ substituents independently selected from the group consisting of $C_1$-$C_6$alkyl, $C_1$-$C_6$haloalkyl, $C_3$-$C_6$cycloalkyl, $C_1$-$C_6$alkoxy, $C_1$-$C_6$haloalkoxy, cyano, and halo. In some cases, ring A is unsubstituted. In some cases, ring A is substituted with 1 $R^A$. In some cases, ring A is substituted with 2 $R^A$.

As described herein, each $R^A$ is independently selected from the group consisting of $C_1$-$C_6$alkyl, $C_1$-$C_6$haloalkyl, $C_3$-$C_6$cycloalkyl, $C_1$-$C_6$alkoxy, $C_1$-$C_6$haloalkoxy, cyano, and halo. In some embodiments, at least one $R^A$ is $C_1$-$C_6$alkyl, $C_3$-$C_6$cycloalkyl, or halo.

In some embodiments, $R^A$ is $C_1$-$C_6$ alkyl such as, for example, methyl.

In some embodiments, $R^A$ is $C_1$-$C_6$alkoxy such as, for example, methoxy or hexoxy.

In some embodiments, $R^A$ is nitro.

In some embodiments, $R^A$ is

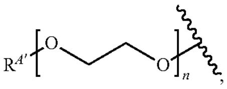, wherein n is 3. In some embodiments, in conjunction with other above or below embodiments, RA' is methyl.

In some embodiments, $R^A$ is a $C_1$-$C_3$alkylene-$C_5$-$C_{10}$heterocycloalkyl having 1-4 ring heteroatoms independently selected from N, O, S. For example, in some embodiments, $R^A$ is morpholinyl.

In some embodiments, in conjunction with above or below embodiments, ring A (including $R^A$ when present) is selected from the group consisting of:

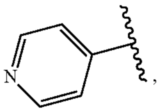, 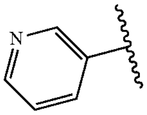, 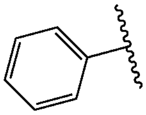,

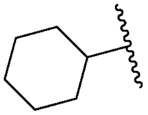, 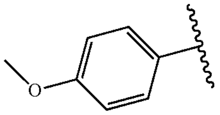,

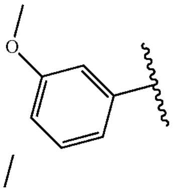, 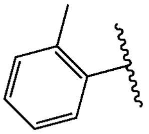,

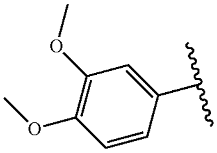, 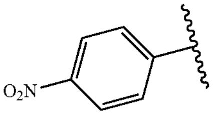,

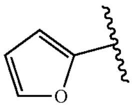, 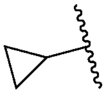,

-continued

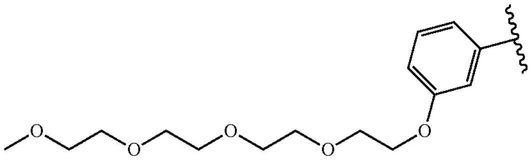,

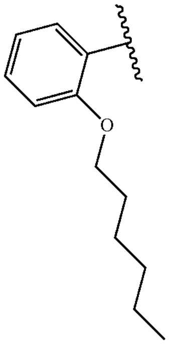, 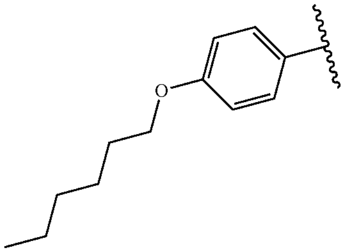,

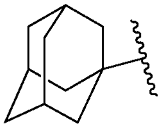, 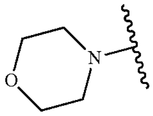, 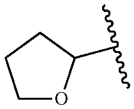,

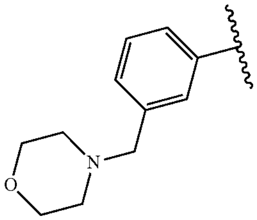, 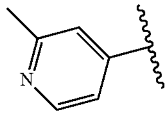,

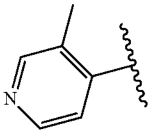, 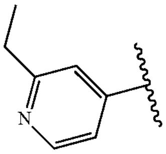, 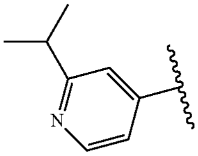,

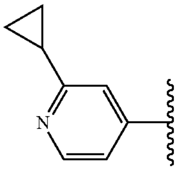, 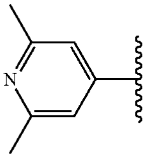, 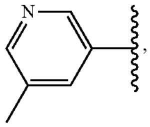,

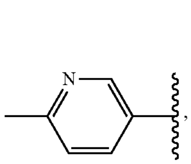, 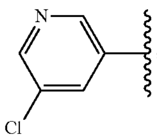, 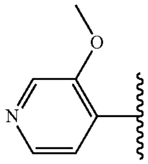,

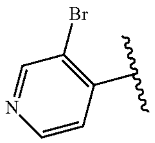, and 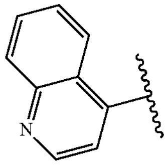.

In some embodiments, ring A is

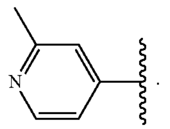 [SMILES: *c1ccnc(C)c1]

In some embodiments, ring A is

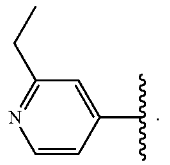

In some embodiments, ring A is

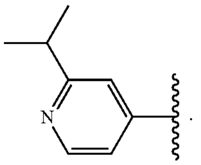 [SMILES: *c1ccnc(C(C)C)c1]

In some embodiments, ring A is

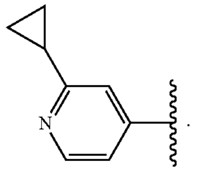 [SMILES: *c1ccnc(C2CC2)c1]

In some embodiments, ring A is

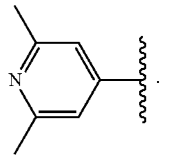 [SMILES: *c1cc(C)nc(C)c1]

In some embodiments, ring A is

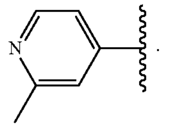 [SMILES: *c1ccnc(C)c1]

In some embodiments, ring A is

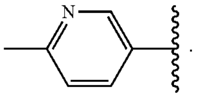 [SMILES: *c1ccc(C)nc1]

In some embodiments, ring A is

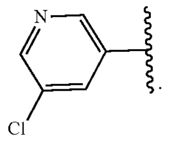 [SMILES: *c1cncc(Cl)c1]

Ring B and $R^B$

The disclosure provides compounds comprising a ring B moiety. In some embodiments, ring B is substituted with 1-3 substituents ($R^B$), as described herein.

In some embodiments, ring B comprises a $C_6$-$C_{10}$aryl. Suitable nonlimiting examples of $C_6$-$C_{10}$aryl ring B include phenyl and naphthyl.

In some embodiments, ring B comprises a 5-10 membered heteroaryl having 1-4 ring heteroatoms selected from N, O, and S. Suitable nonlimiting examples of a 5-10 membered heteroaryl ring B include quinolinyl (e.g., 8-quinolinyl and 4-quinolinyl).

As described herein, in some embodiments ring B is substituted with 1-3 $R^B$. In some embodiments, in conjunction with above or below embodiments, $R^B$ is halo (e.g., fluoro, chloro, and/or bromo).

In some embodiments, in conjunction with above or below embodiments, $R^B$ is $C_1$-$C_6$aryl (e.g., phenyl).

In some embodiments, in conjunction with above or below embodiments $R^B$ is $C_1$-$C_6$haloalkyl (e.g., trifluoromethyl).

In some embodiments, in conjunction with above or below embodiments $R^B$ is nitro.

In some embodiments, in conjunction with above or below embodiments $R^B$ is $C_1$-$C_6$alkoxy. Suitable nonlimiting examples of $C_1$-$C_6$alkoxy $R^B$ include methoxy, ethoxy, isopropoxy, and isobutoxy.

In some embodiments, in conjunction with above or below embodiments $R^B$ is —C(O)$OR^{B'}$, wherein $R^{B'}$ is $C_1$-$C_3$alkyl (e.g., methyl or ethyl).

In some embodiments, in conjunction with above or below embodiments, $R^B$ is $C_1$-$C_3$alkylene-$C_6$-$C_{10}$aryl (e.g., benzyl).

In some embodiments, in conjunction with above or below embodiments, $R^B$ is $C_1$-$C_6$haloalkoxy. Suitable nonlimiting examples of $C_1$-$C_6$haloalkoxy $R^B$ include trifluoromethoxy, difluoromethoxy, and 1,1-difluoro-2,2-difluoroethoxy. In some embodiments, $R^B$ is difluromethoxy.

In some embodiments, in conjunction with above or below embodiments, $R^B$ is —O—$C_1$-$C_3$alkylene-$C_6$-$C_{10}$aryl (e.g., benzyloxy).

In some embodiments, in conjunction with above or below embodiments, $R^B$ is $C_1$-$C_6$alkyl as described herein (e.g., methyl, ethyl, propyl, or isopropyl, butyl, isobutyl, sec-butyl, and tert-butyl).

In some embodiments, in conjunction with above or below embodiments, $R^B$ is $C_3$-$C_6$cycloalkyl (e.g., cyclopropyl or cyclobutyl).

In some embodiments, in conjunction with above or below embodiments, $R^B$ is $C_3$-$C_6$cycloalkoxy (e.g., cyclopropoxy or cyclobutoxy).

In some embodiments, in conjunction with above or below embodiments, two ortho $R^B$ are taken together with the atoms to which they are attached form a 5 or 6 membered cycloheteroalkyl comprising 1-3 ring heteroatoms independently selected from N, O, S. For example, in some embodiments two ortho $R^B$ form a 1,3-dioxolane.

In some embodiments, in conjunction with above or below embodiments, two ortho $R^B$ are taken together with the atoms to which they are attached form a 5 or 6 membered cycloalkyl (e.g., cyclohexyl).

In some embodiments, in conjunction with above or below embodiments, two ortho $R^B$ are taken together with the atoms to which they are attached form a 5 or 6 membered cycloheteroalkyl comprising 1-3 ring heteroatoms independently selected from N, O, S (e.g., 2,2-dimethylchromanyl).

In some embodiments, $R^B$ comprises $R^{B'}$, wherein $R^{B'}$ is H, $C_1$-$C_3$alkyl, or $C_1$-$C_6$haloalkyl. In some embodiments, in conjunction with above or below embodiments, $R^B$ is —$SR^{B'}$. For example, in some embodiments —$SR^{B'}$ is —$SC_1$-$C_6$alkyl or —$SC_1$-$C_6$haloalkyl such as —$SCH_3$ or —$SCF_3$. In some embodiments, in conjunction with above or below embodiments, $R^B$ is —$C_1$-$C_3$alkylene-$OR^{B'}$ (e.g., —$CH_2$—$CH_2$—OH).

In some embodiments, in conjunction with above or below embodiments, $R^B$ is —$C_1$-$C_3$alkylene-$C_5$-$C_6$heteroaryl having 1-4 ring heteroatoms independently selected from N, O, S. Suitable nonlimiting examples of $C_1$-$C_3$alkylene-$C_5$-$C_6$heteroaryl include (1,2,4-triazol-1-yl)methyl.

In some embodiments, in conjunction with above or below embodiments, $R^B$ is —O—$C_1$-$C_3$alkylene-$C_1$-$C_6$alkoxy (e.g., 2-methoxyethoxy).

In some embodiments, in conjunction with above or below embodiments, $R^B$ is —CN.

In some embodiments, in conjunction with above or below embodiments, $R^B$ is —$C_1$-$C_3$alkylene-$C_3$-$C_6$cycloalkyl (e.g., cyclopropylmethyl).

In some embodiments, in conjunction with above or below embodiments, $R^B$ is a $C_1$-$C_3$alkylene-$C_6$-$C_{10}$heterocycloalkyl having 1-4 ring hetereoatoms independently selected from N, O, S (e.g., (4-methylpiperazin-1-yl)methyl.

In some embodiments, in conjunction with above or below embodiments, $R^B$ is —C(Z)$C_1$-$C_6$haloalkyl, wherein Z is O or S. For example, in some embodiments, $R^B$ is —C(Z)$CF_3$ such that $R^B$ is —C(O)$CF_3$ or —C(S)$CF_3$.

In some embodiments, the disclosure provides compounds wherein $R^B$ is independently selected from the group consisting of $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_1$-$C_3$alkylene-$C_3$-$C_6$cycloalkyl, cyano, and halo.

In some embodiments, the disclosure provides compounds or salts of formula (I), wherein ring B has a structure of:

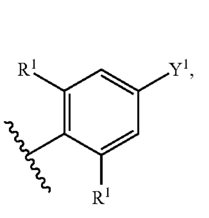
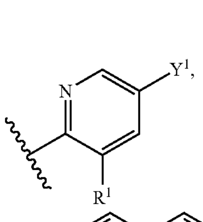
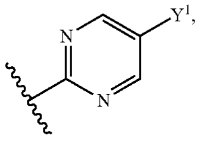
or
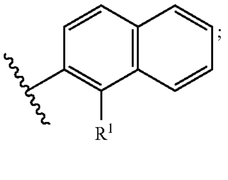

each $R^1$ is independently hydrogen, halogen, $C_1$-$C_3$alkyl, $C_3$-$C_6$cycloalkyl, $C_1$-$C_6$alkoxy, and $C_1$-$C_6$haloalkoxy; and $Y^1$ is independently selected from the group consisting of $C_1$-$C_6$alkyl, $C_3$-$C_6$cycloalkyl, $C_1$-$C_6$haloalkyl, $C_1$-$C_6$haloalkoxy, $C_1$-$C_6$alkoxy, and $C_3$-$C_6$cycloalkoxy.

In some embodiments, $R^1$ is independently selected from the group consisting of H, D, fluoro, methyl, ethyl, and isopropyl.

In some embodiments, each $Y^1$ is independently selected from the group consisting of fluoromethyl, difluoromethyl, trifluoromethyl, trifluoromethoxy, pentafluoropropyl, isopropyl, isobutyl, cyclopropyl, 1,2-(difluoro)ethoxy, cyclopropyloxy, isopropoxy, ethoxy, and methoxy. In some embodiments $Y^1$ is isobutyl.

In some embodiments, the disclosure provides compounds or salts of formula (I), wherein ring B comprises a $C_{6-10}$aryl or a 5-10 membered heteroaryl having 1-4 ring heteroatoms selected from N, O, and S, and is optionally substituted with 1-3 $R^B$. In some embodiments, ring B comprises a phenyl, pyridinyl, pyrimidinyl, or naphthyl.

As described herein, each $R^B$ is independently selected from the group consisting of $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_1$-$C_3$alkylene-$C_3$-$C_6$cycloalkyl, cyano, and halo.

In some embodiments, in conjunction with above or below embodiments, ring B (including $R^B$ and $R^{B'}$ when present) is selected from the group consisting of:

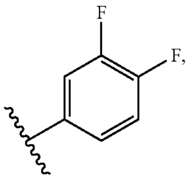
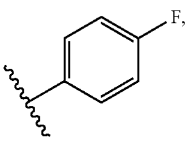
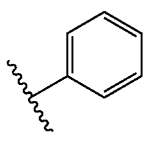
,
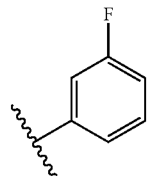
,
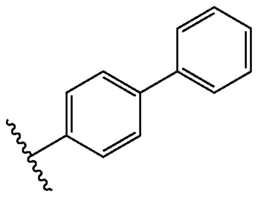
,
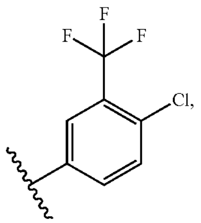
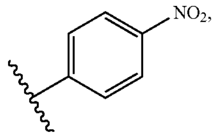
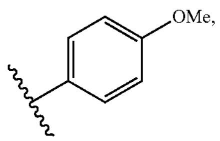
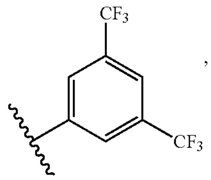
,
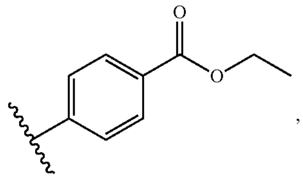
, -continued
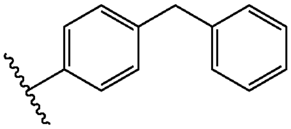,
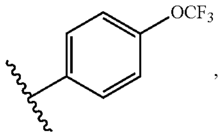,
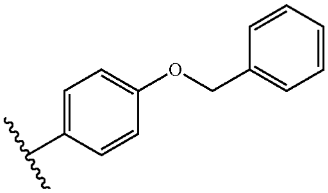,
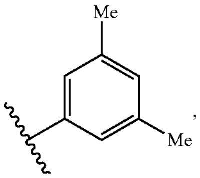,
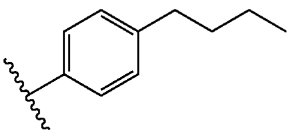,
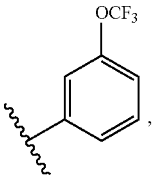,
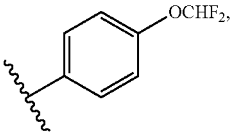
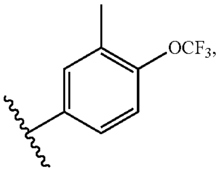,
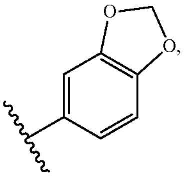
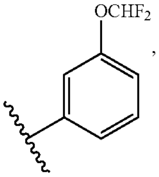,
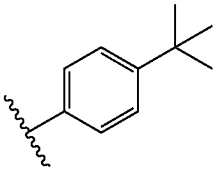,
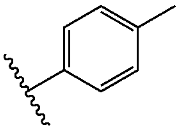,
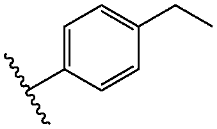,
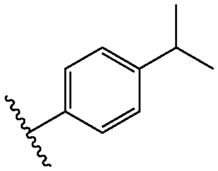,
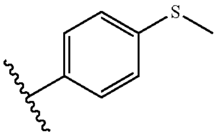,
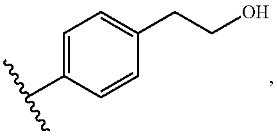,
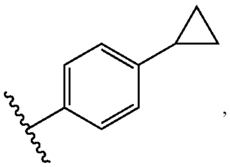,
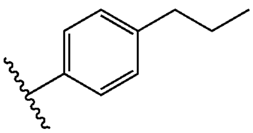,
-continued
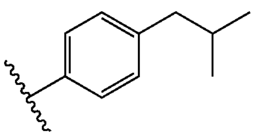
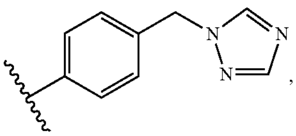,
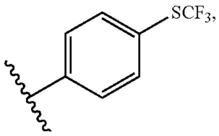
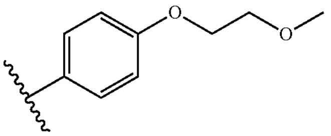,
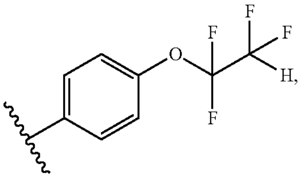,
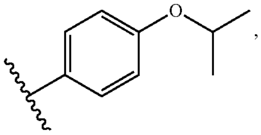,
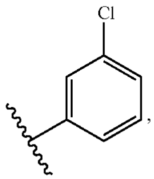,
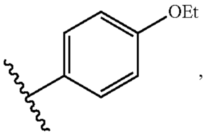,
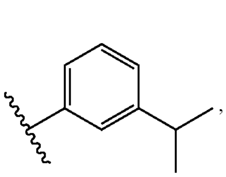,
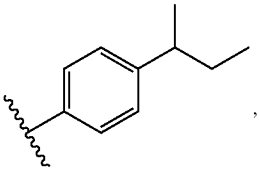,
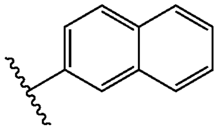
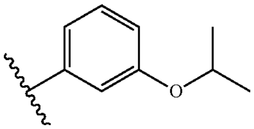,
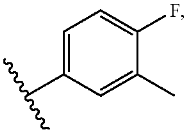,
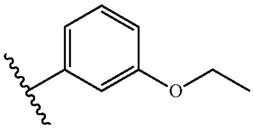,
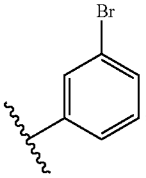,
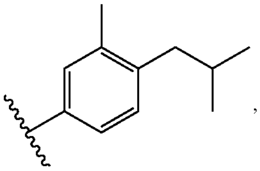,
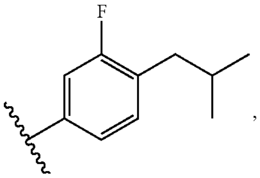,
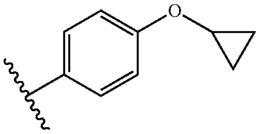,
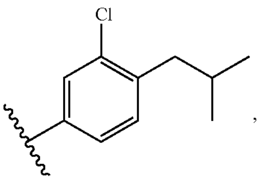
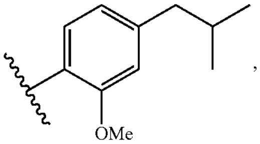, -continued

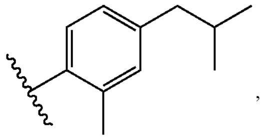,
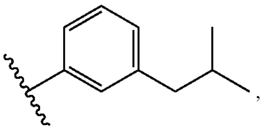,
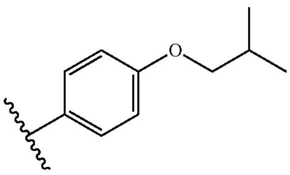,
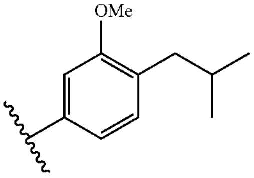,
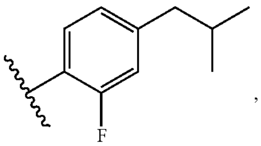,
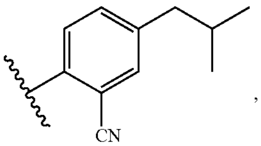,
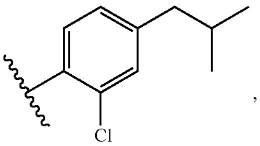,
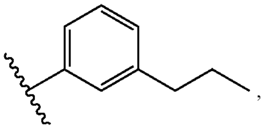,
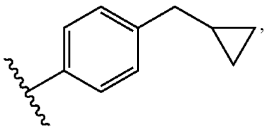,
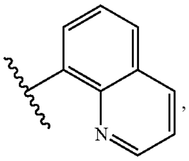,
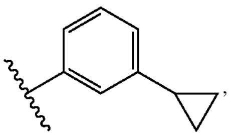,
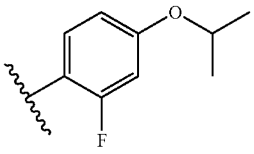,
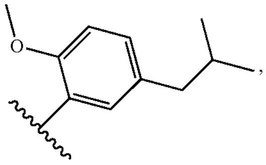,
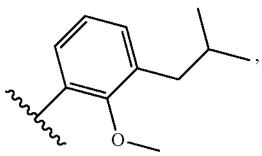,
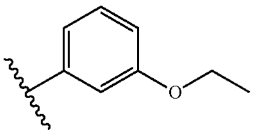,
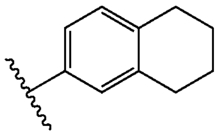,
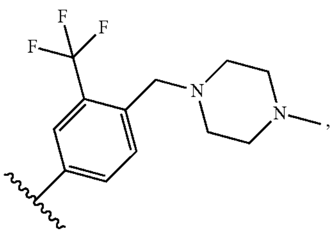,
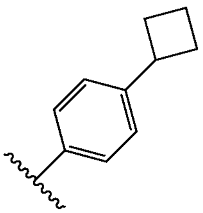,
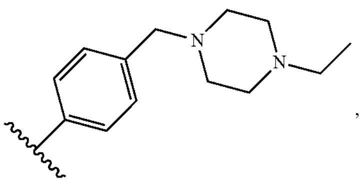, -continued

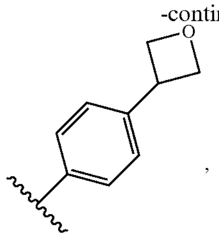,
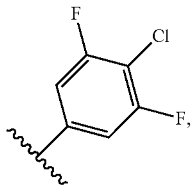
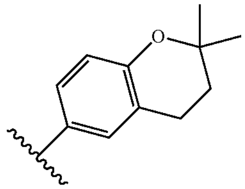,
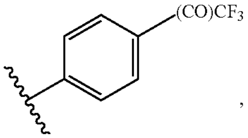,
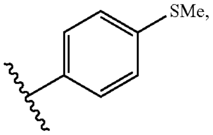
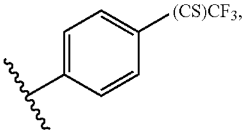
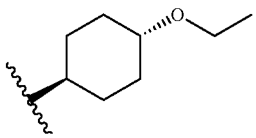,
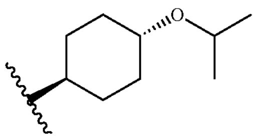,
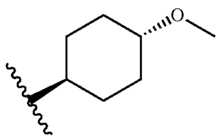, and
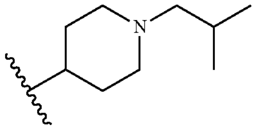.

Core Structure

The disclosed compounds or salts of formula (I) comprise a core structure having the formula

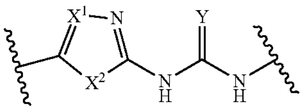

which connects ring A and ring B of the disclosed compounds or salts.

In some embodiments $X^1$ is $CR^1$, wherein $R^1$ is H or $C_1$-$C_6$alkyl (e.g., methyl), as described herein. In some embodiments, $R^1$ is H. In some embodiments, $X^1$ is N.

In some embodiments, $X^2$ is S. In some embodiments, $X^2$ is O. In some embodiments, $X^2$ is NH.

In some embodiments, the disclosure provides compounds or salts having a thiazole moiety (i.e., $X^1$ is CH and $X^2$ is S) or a thiadiazole moiety (i.e., $X^1$ is N and $X^2$ is S). In some embodiments, $X^1$ is CH.

In some embodiments, in conjunction with above or below embodiments, Y is O such that the compounds or salts comprise a core structure having the formula

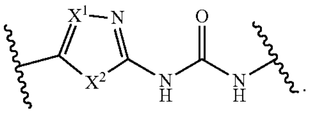

In some embodiments, in conjunction with above or below embodiments, Y is S such that the compounds or salts comprise a core structure having the formula

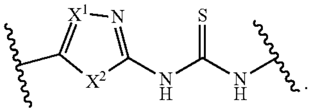.

In some embodiments, Y is O and $X^2$ is S. Thus, in some embodiments, the compounds or salts of formula (I) have a structure selected from one of the following structures:

(II)

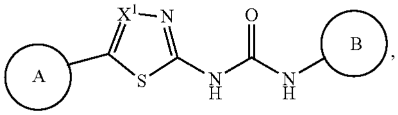, (III)

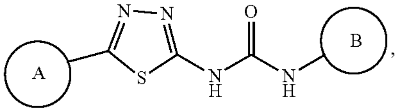, and (IV)

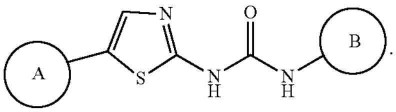.

In some embodiments, Y is S and $X^2$ is S. Thus, in some embodiments, the compounds or salts of formula (I) have a structure selected from one of the following structures:

(IIA)

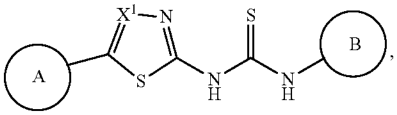, (IIIA)

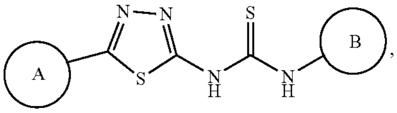, and (IVA)

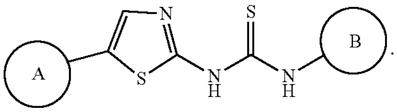.

In some embodiments, the compound or pharmaceutically acceptable salt thereof is shown in Table A below.

TABLE A

| ID | STRUCTURE |
|---|---|
| A1 | 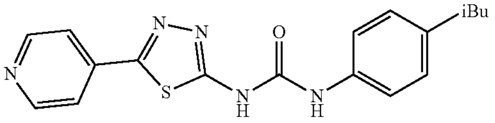 |
| A2 | 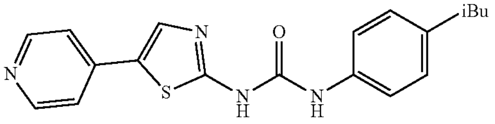 |
| A3 | 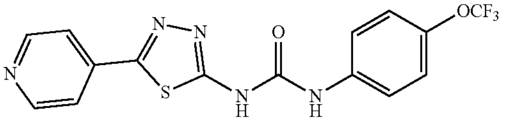 [SMILES: O=C(Nc1ccc(OC(F)(F)F)cc1)Nc1nnc(-c2ccncc2)s1] |
| A4 | 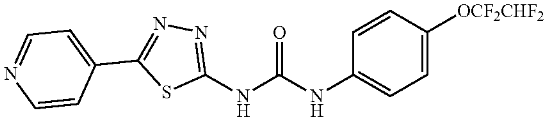 |
| A5 | 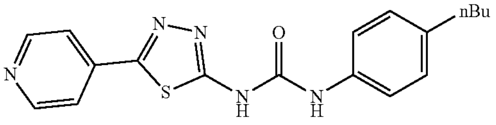 |

TABLE A-continued
| ID | STRUCTURE |
|---|---|
| A6 | 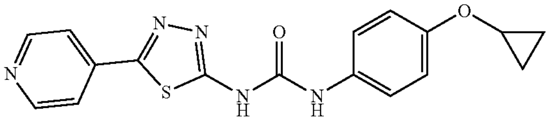 [SMILES: O=C(Nc1ccc(OC2CC2)cc1)Nc1nnc(-c2ccncc2)s1] |
| A7 | 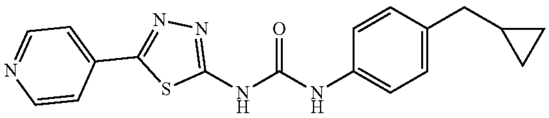 [SMILES: O=C(Nc1ccc(CC2CC2)cc1)Nc1nnc(-c2ccncc2)s1] |
| A8 | 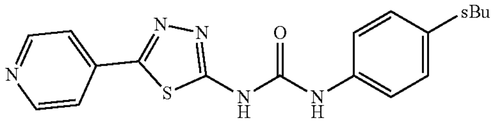 |
| A9 | 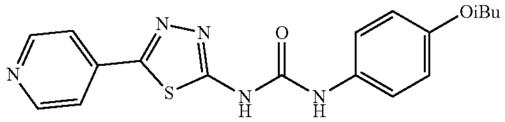 |
| A10 | 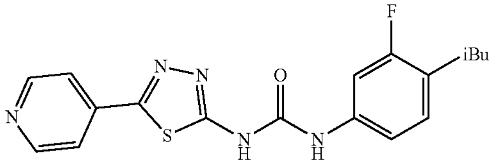 |
| A11 | 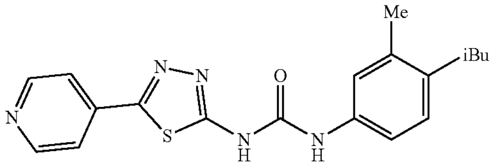 |
| A12 | 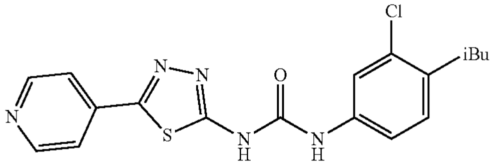 |
| A13 | 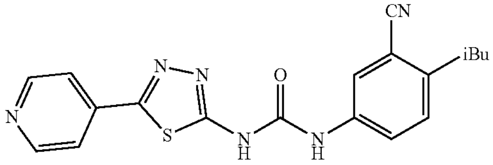 |
| A14 | 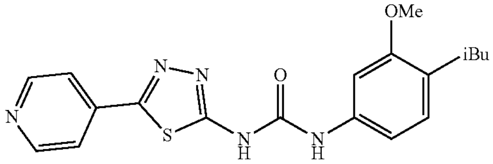 |
| A15 | 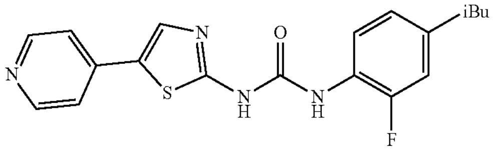 |

TABLE A-continued
| ID | STRUCTURE |
| --- | --- |
| A16 | 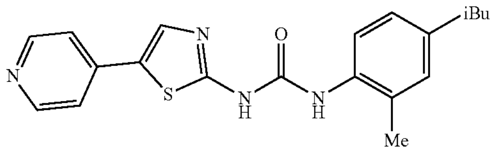 |
| A17 | 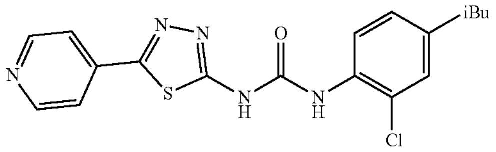 |
| A18 | 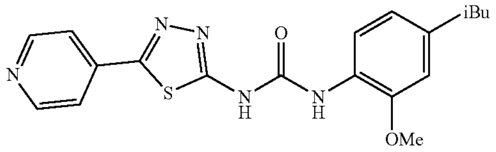 |
| A19 | 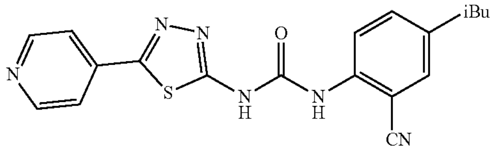 |
| A20 | 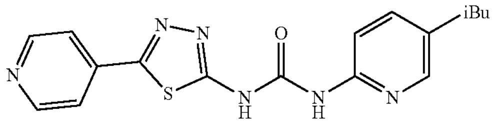 |
| A21 | 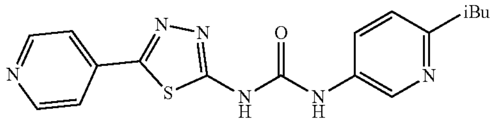 |
| A22 | 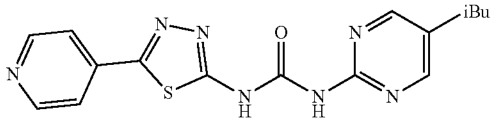 |
| A23 | 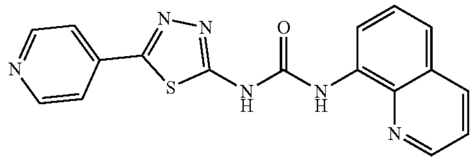 [SMILES: O=C(Nc1nnc(-c2ccncc2)s1)Nc1cccc2cccnc12] |
| A24 | 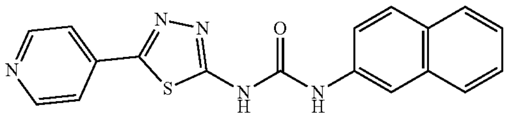 [SMILES: O=C(Nc1ccc2ccccc2c1)Nc1nnc(-c2ccncc2)s1] |
| A25 | 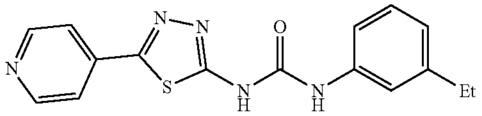 [SMILES: CCc1cccc(NC(=O)Nc2nnc(-c3ccncc3)s2)c1] |

TABLE A-continued
| ID | STRUCTURE |
|---|---|
| A26 | 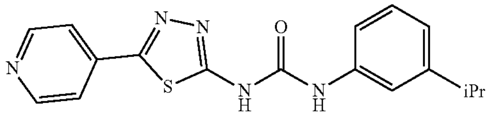 [SMILES: CC(C)c1cccc(NC(=O)Nc2nnc(-c3ccncc3)s2)c1] |
| A27 | 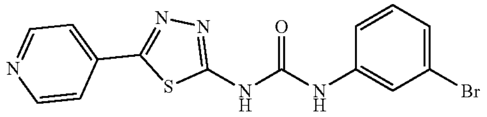 [SMILES: O=C(Nc1cccc(Br)c1)Nc1nnc(-c2ccncc2)s1] |
| A28 | 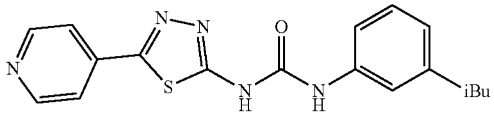 |
| A29 | 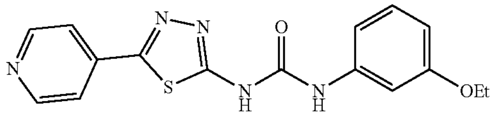 [SMILES: CCOc1cccc(NC(=O)Nc2nnc(-c3ccncc3)s2)c1] |
| A30 | 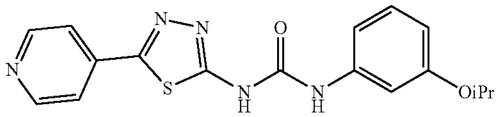 [SMILES: CC(C)Oc1cccc(NC(=O)Nc2nnc(-c3ccncc3)s2)c1] |
| A31 | 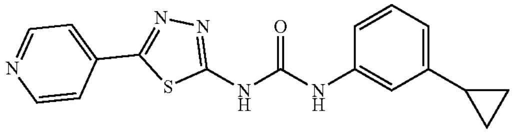 [SMILES: O=C(Nc1cccc(C2CC2)c1)Nc1nnc(-c2ccncc2)s1] |
| A32 | 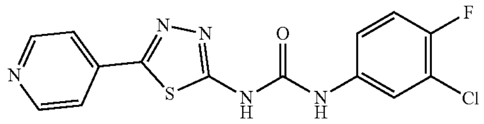 [SMILES: O=C(Nc1ccc(F)c(Cl)c1)Nc1nnc(-c2ccncc2)s1] |
| A33 | 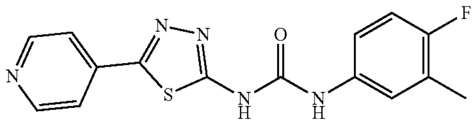 [SMILES: Cc1cc(NC(=O)Nc2nnc(-c3ccncc3)s2)ccc1F] |
| A34 | 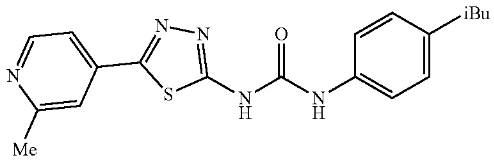 |
| A35 | 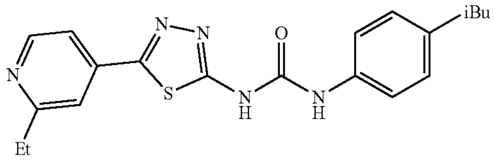 |
| A36 | 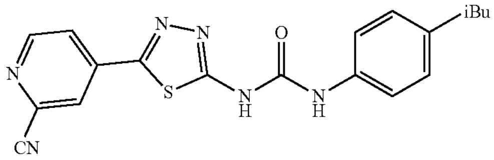 |

TABLE A-continued
| ID | STRUCTURE |
|---|---|
| A37 | 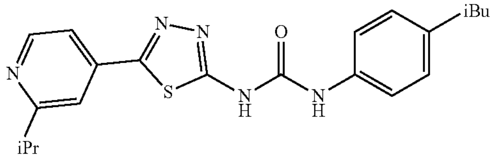 |
| A38 | 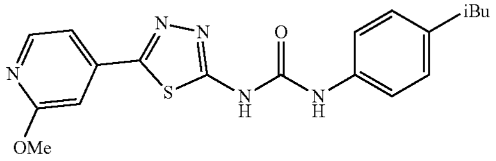 |
| A39 | 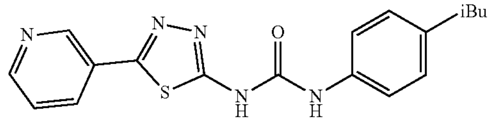 |
| A40 | 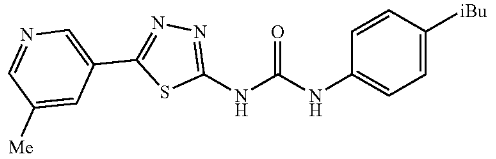 |
| A41 | 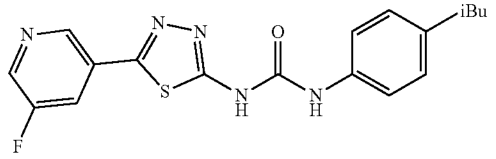 |
| A42 | 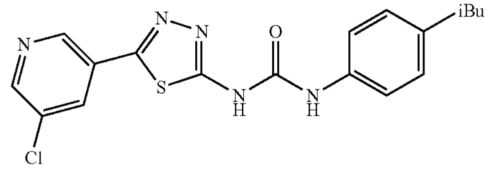 |
| A43 | 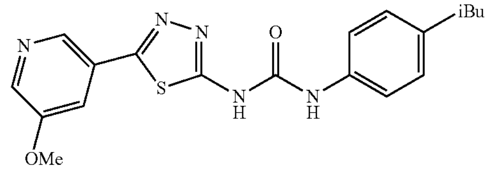 |
| A44 | 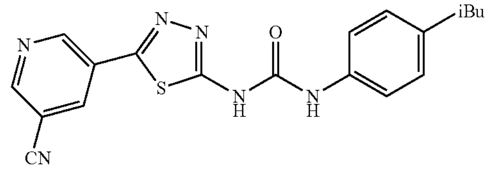 |
| A45 | 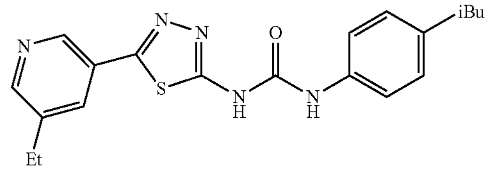 |

TABLE A-continued
| ID | STRUCTURE |
| --- | --- |
| A46 | 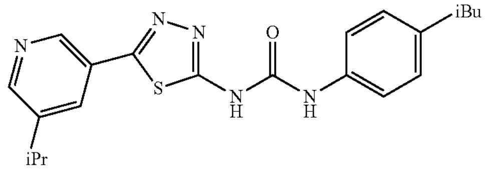 |
| A47 | 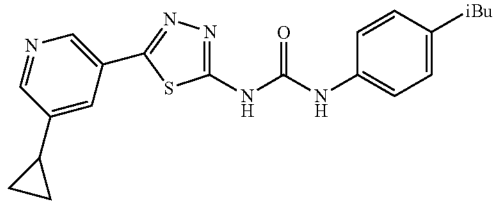 |
| A48 | 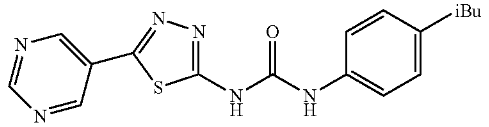 |
| A49 | 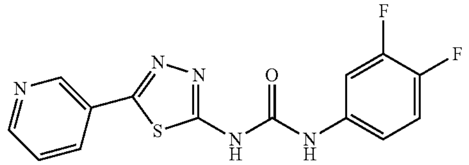 [SMILES: O=C(Nc1ccc(F)c(F)c1)Nc1nnc(-c2cccnc2)s1] |
| A50 | 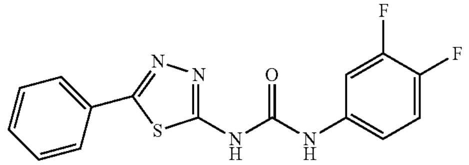 [SMILES: O=C(Nc1ccc(F)c(F)c1)Nc1nnc(-c2ccccc2)s1] |
| A51 | 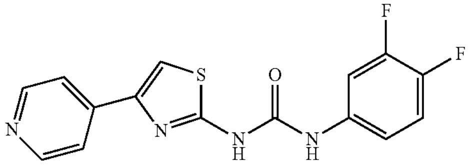 [SMILES: O=C(Nc1ccc(F)c(F)c1)Nc1nc(-c2ccncc2)cs1] |
| A52 | 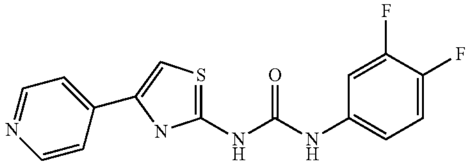 |
| A53 | 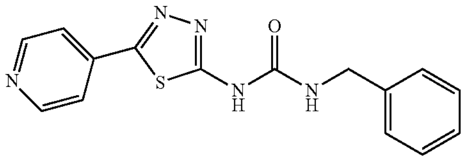 [SMILES: O=C(NCc1ccccc1)Nc1nnc(-c2ccncc2)s1] |
| A54 | 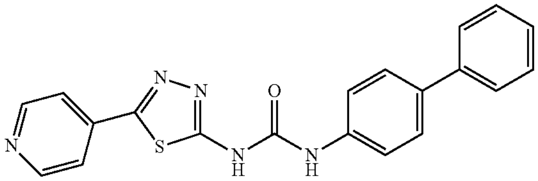 [SMILES: O=C(Nc1ccc(-c2ccccc2)cc1)Nc1nnc(-c2ccncc2)s1] |

TABLE A-continued
| ID | STRUCTURE |
| --- | --- |
| A55 | 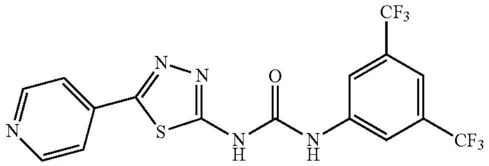 [SMILES: O=C(Nc1cc(C(F)(F)F)cc(C(F)(F)F)c1)Nc1nnc(-c2ccncc2)s1] |
| A56 | 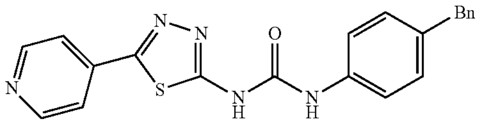 [SMILES: O=C(Nc1ccc(Cc2ccccc2)cc1)Nc1nnc(-c2ccncc2)s1] |
| A57 | 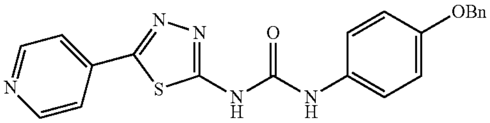 [SMILES: O=C(Nc1ccc(OCc2ccccc2)cc1)Nc1nnc(-c2ccncc2)s1] |
| A58 | 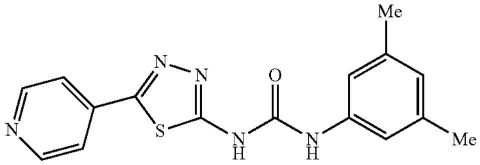 [SMILES: Cc1cc(C)cc(NC(=O)Nc2nnc(-c3ccncc3)s2)c1] |
| A59 | 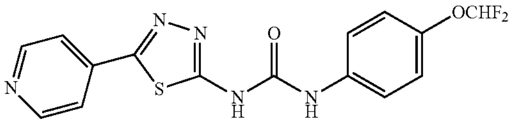 [SMILES: O=C(Nc1ccc(OC(F)F)cc1)Nc1nnc(-c2ccncc2)s1] |
| A60 | 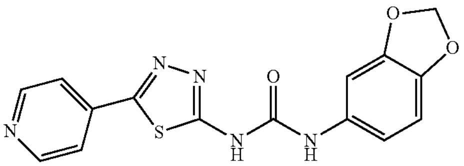 [SMILES: O=C(Nc1ccc2c(c1)OCO2)Nc1nnc(-c2ccncc2)s1] |
| A61 | 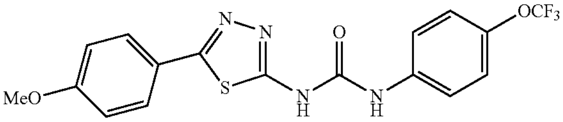 [SMILES: COc1ccc(-c2nnc(NC(=O)Nc3ccc(OC(F)(F)F)cc3)s2)cc1] |
| A62 | 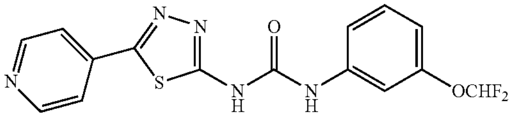 [SMILES: O=C(Nc1cccc(OC(F)F)c1)Nc1nnc(-c2ccncc2)s1] |
| A63 | 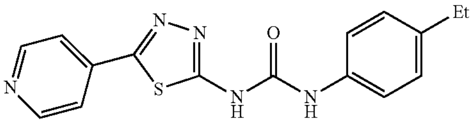 |
| A64 | 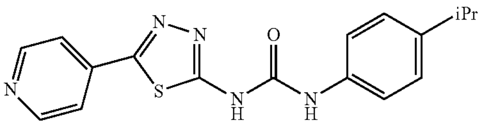 [SMILES: CC(C)c1ccc(NC(=O)Nc2nnc(-c3ccncc3)s2)cc1] |

TABLE A-continued
| ID | STRUCTURE |
|---|---|
| A65 | 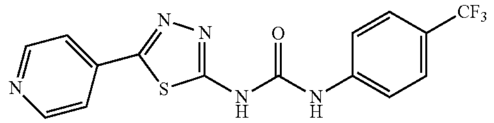 |
| A66 | 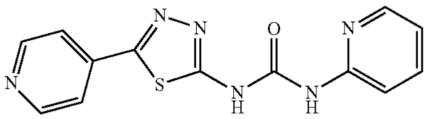 [SMILES: O=C(Nc1ccccn1)Nc1nnc(-c2ccncc2)s1] |
| A67 | 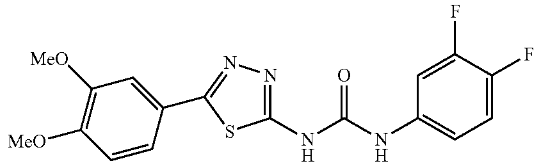 [SMILES: COc1ccc(-c2nnc(NC(=O)Nc3ccc(F)c(F)c3)s2)cc1OC] |
| A68 | 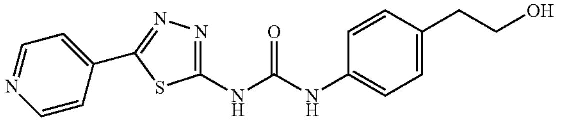 [SMILES: O=C(Nc1ccc(CCO)cc1)Nc1nnc(-c2ccncc2)s1] |
| A69 | 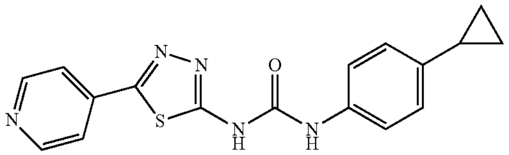 [SMILES: O=C(Nc1ccc(C2CC2)cc1)Nc1nnc(-c2ccncc2)s1] |
| A70 | 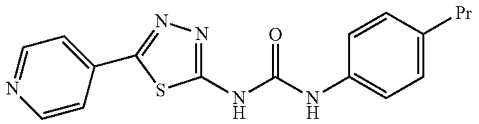 |
| A1 | 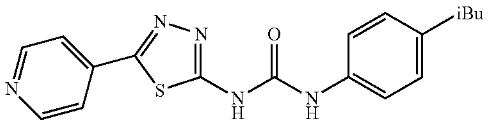 |
| A72 | 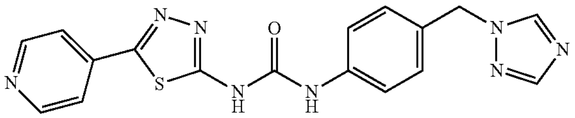 [SMILES: O=C(Nc1ccc(Cn2cncn2)cc1)Nc1nnc(-c2ccncc2)s1] |
| A73 | 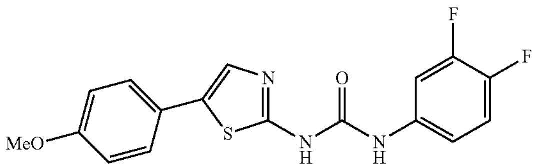 [SMILES: COc1ccc(-c2cnc(NC(=O)Nc3ccc(F)c(F)c3)s2)cc1] |
| A74 | 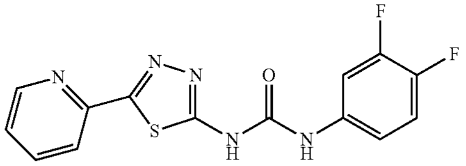 [SMILES: O=C(Nc1ccc(F)c(F)c1)Nc1nnc(-c2ccccn2)s1] |

TABLE A-continued
| ID | STRUCTURE |
|---|---|
| A75 | 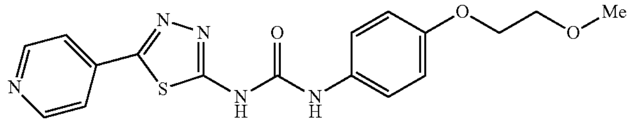 [SMILES: COCCOc1ccc(NC(=O)Nc2nnc(-c3ccncc3)s2)cc1] |
| A76 | 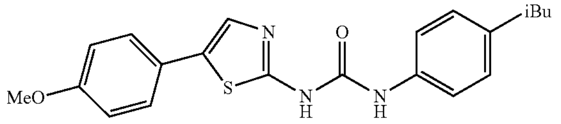 |
| A77 | 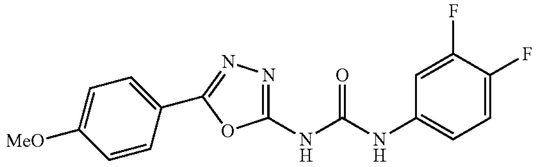 [SMILES: COc1ccc(-c2nnc(NC(=O)Nc3ccc(F)c(F)c3)o2)cc1] |
| A78 | 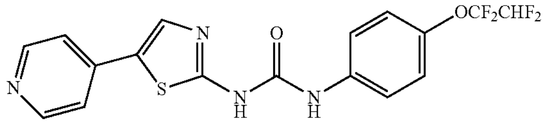 |
| A79 | 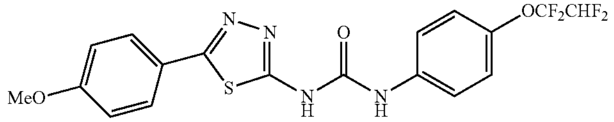 |
| A80 | 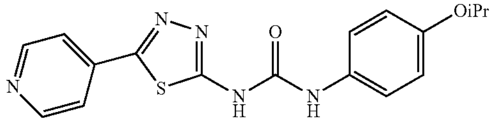 |
| A81 | 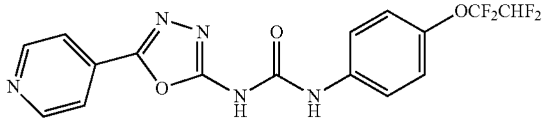 |
| A82 | 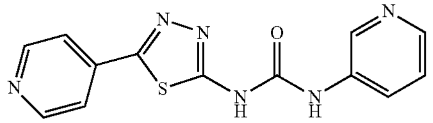 [SMILES: O=C(Nc1cccnc1)Nc1nnc(-c2ccncc2)s1] |
| A83 | 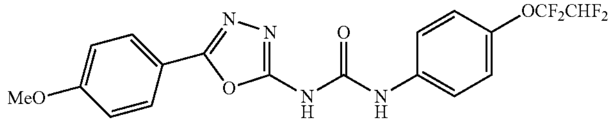 |
| A84 | 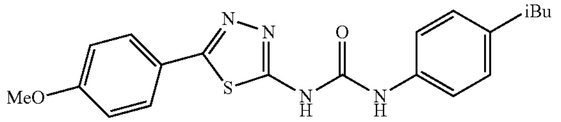 |
| A85 | 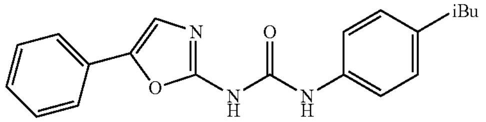 |

TABLE A-continued
| ID | STRUCTURE |
|---|---|
| A86 | 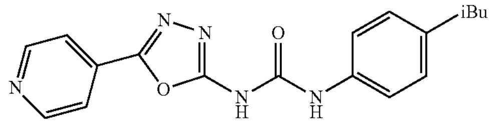 |
| A87 | 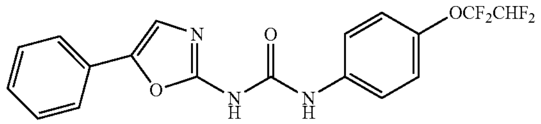 |
| A88 | 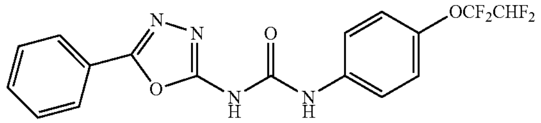 |
| A89 | 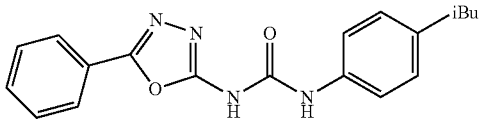 |
| A90 | 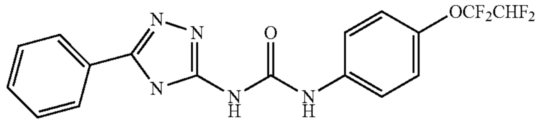 |
| A91 | 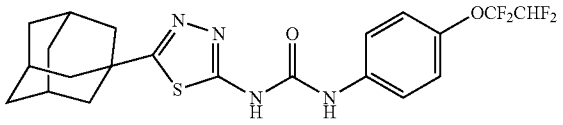 |
| A92 | 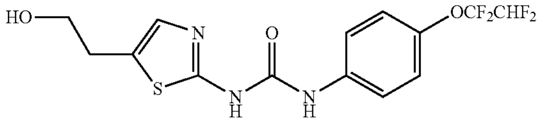 |
| A93 | 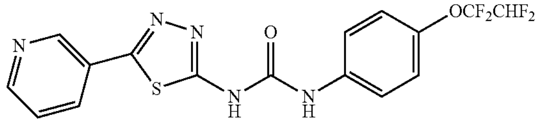 |
| A94 | 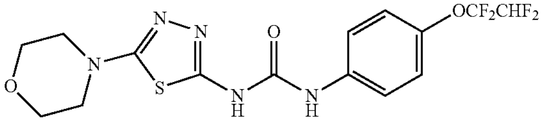 |
| A95 | 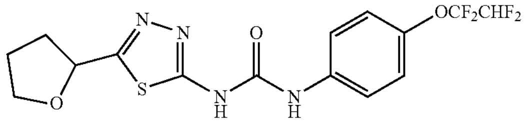 |
| A96 | 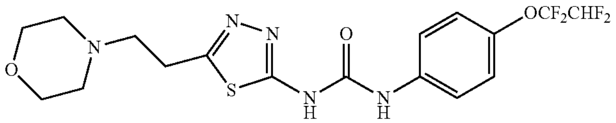 |

TABLE A-continued
| ID | STRUCTURE |
| --- | --- |
| A97 | 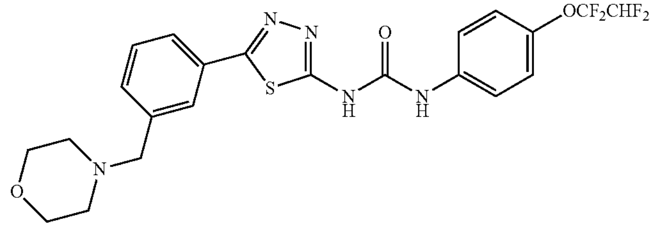 |
| A98 | 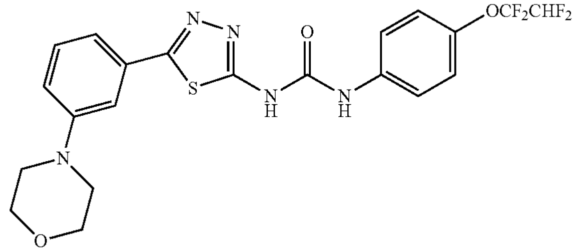 |
| A99 | 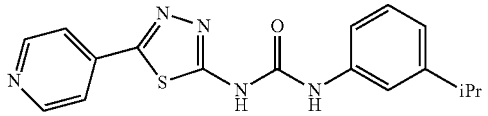 [SMILES: CC(C)c1cccc(NC(=O)Nc2nnc(-c3ccncc3)s2)c1] |
| A100 | 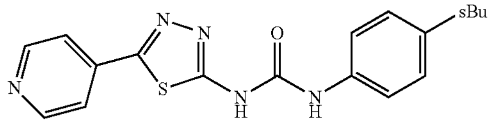 |
| A101 | 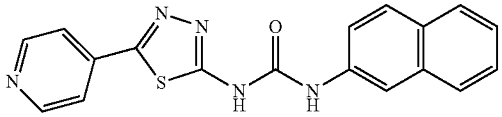 [SMILES: O=C(Nc1ccc2ccccc2c1)Nc1nnc(-c2ccncc2)s1] |
| A102 | 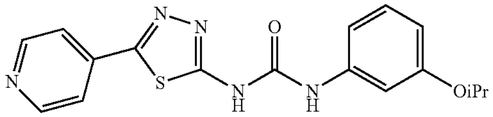 [SMILES: CC(C)Oc1cccc(NC(=O)Nc2nnc(-c3ccncc3)s2)c1] |
| A103 | 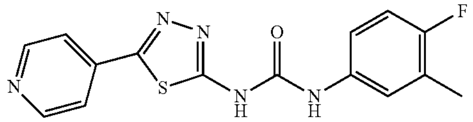 [SMILES: Cc1cc(NC(=O)Nc2nnc(-c3ccncc3)s2)ccc1F] |
| A104 | 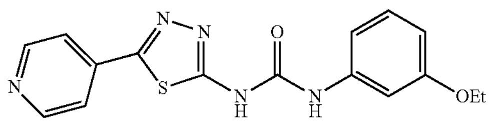 |
| A105 | 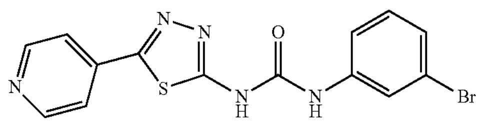 [SMILES: O=C(Nc1cccc(Br)c1)Nc1nnc(-c2ccncc2)s1] |
| A106 | 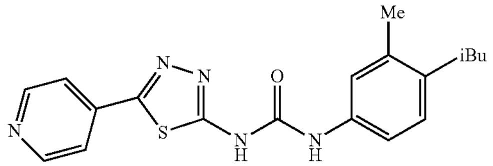 |

TABLE A-continued
| ID | STRUCTURE |
|---|---|
| A107 | 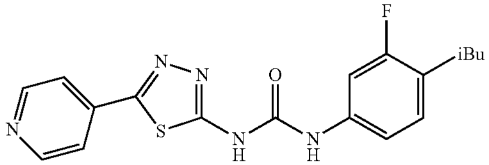 |
| A108 | 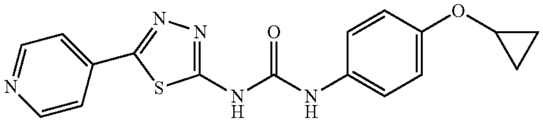 [SMILES: O=C(Nc1ccc(OC2CC2)cc1)Nc1nnc(-c2ccncc2)s1] |
| A109 | 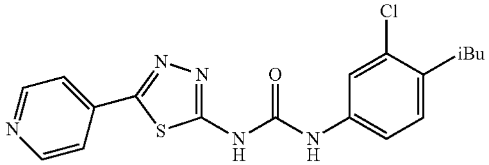 |
| A110 | 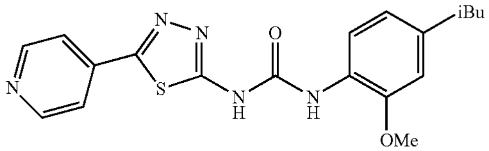 |
| A111 | 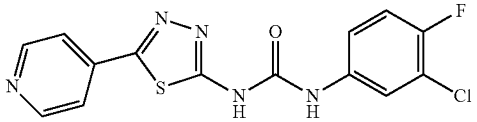 [SMILES: O=C(Nc1ccc(F)c(Cl)c1)Nc1nnc(-c2ccncc2)s1] |
| A112 | 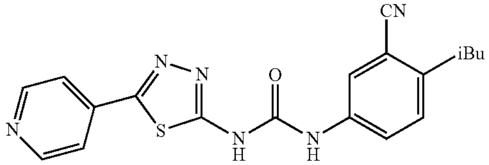 |
| A113 | 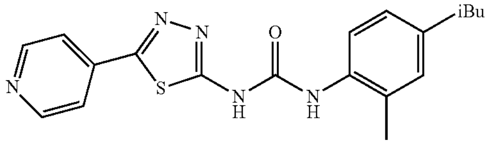 |
| A114 | 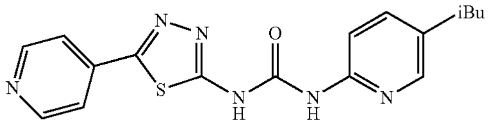 |
| A115 | 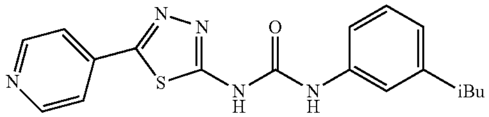 |
| A116 | 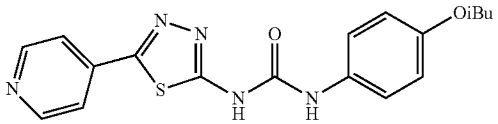 |

TABLE A-continued
| ID | STRUCTURE |
| --- | --- |
| A117 | 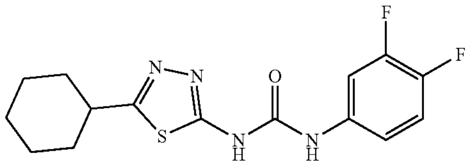 [SMILES: O=C(Nc1ccc(F)c(F)c1)Nc1nnc(C2CCCCC2)s1] |
| A118 | 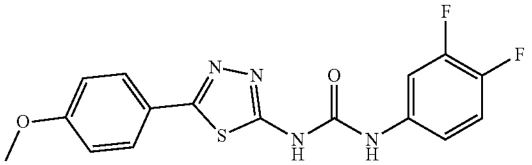 [SMILES: COc1ccc(-c2nnc(NC(=O)Nc3ccc(F)c(F)c3)s2)cc1] |
| A119 | 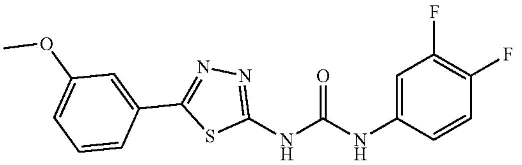 [SMILES: COc1cccc(-c2nnc(NC(=O)Nc3ccc(F)c(F)c3)s2)c1] |
| A120 | 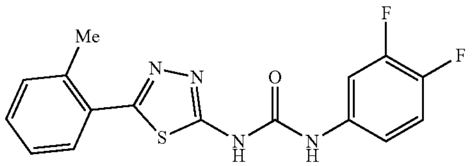 [SMILES: Cc1ccccc1-c1nnc(NC(=O)Nc2ccc(F)c(F)c2)s1] |
| A121 | 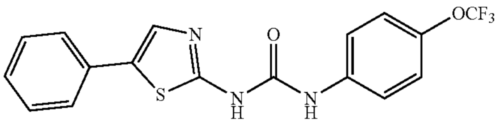 [SMILES: O=C(Nc1ccc(OC(F)(F)F)cc1)Nc1ncc(-c2ccccc2)s1] |
| A122 | 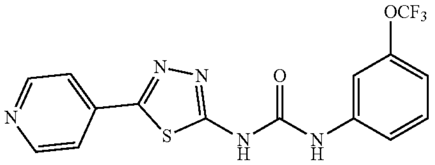 [SMILES: O=C(Nc1cccc(OC(F)(F)F)c1)Nc1nnc(-c2ccncc2)s1] |
| A123 | 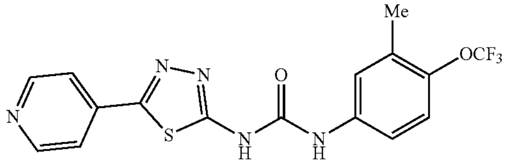 [SMILES: Cc1cc(NC(=O)Nc2nnc(-c3ccncc3)s2)ccc1OC(F)(F)F] |
| A124 | 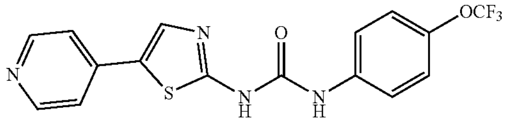 [SMILES: O=C(Nc1ccc(OC(F)(F)F)cc1)Nc1ncc(-c2ccncc2)s1] |
| A125 | 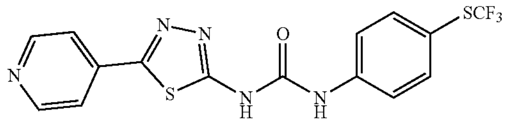 |

TABLE A-continued
| ID | STRUCTURE |
| --- | --- |
| A126 | 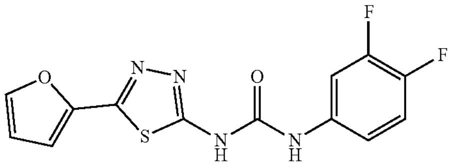 [SMILES: O=C(Nc1ccc(F)c(F)c1)Nc1nnc(-c2ccco2)s1] |
| A127 | 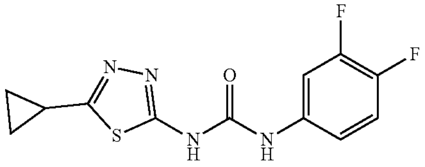 [SMILES: O=C(Nc1ccc(F)c(F)c1)Nc1nnc(C2CC2)s1] |
| A128 | 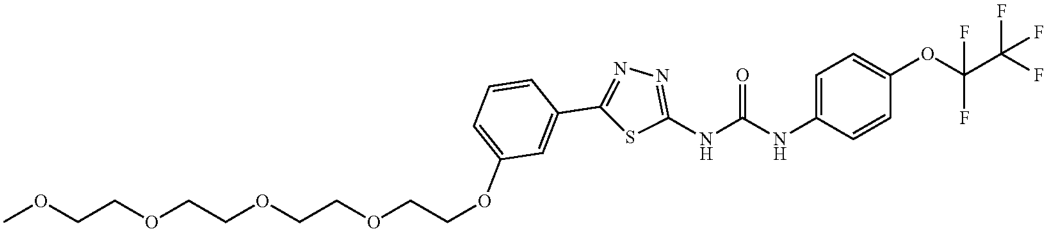 [SMILES: COCCOCCOCCOCCOc1cccc(-c2nnc(NC(=O)Nc3ccc(OC(F)(F)C(F)(F)F)cc3)s2)c1] |
| A129 | 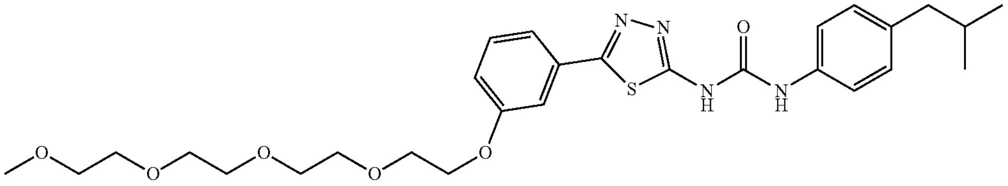 [SMILES: COCCOCCOCCOCCOc1cccc(-c2nnc(NC(=O)Nc3ccc(CC(C)C)cc3)s2)c1] |
| A130 | 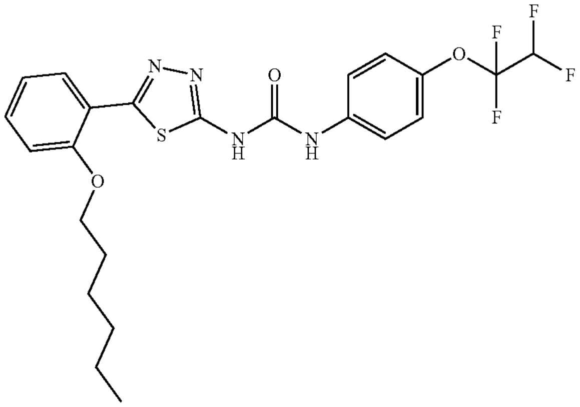 [SMILES: CCCCCCOc1ccccc1-c1nnc(NC(=O)Nc2ccc(OC(F)(F)C(F)F)cc2)s1] |
| A131 | 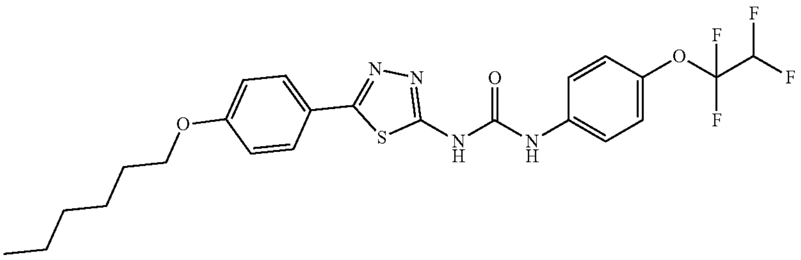 [SMILES: CCCCCCOc1ccc(-c2nnc(NC(=O)Nc3ccc(OC(F)(F)C(F)F)cc3)s2)cc1] |

TABLE A-continued
| ID | STRUCTURE |
|---|---|
| A132 | 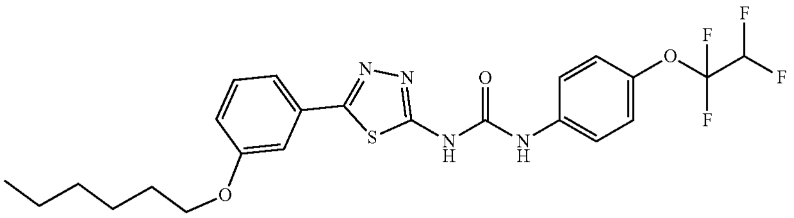 [SMILES: CCCCCCOc1cccc(-c2nnc(NC(=O)Nc3ccc(OC(F)(F)C(F)F)cc3)s2)c1] |
| A133 | 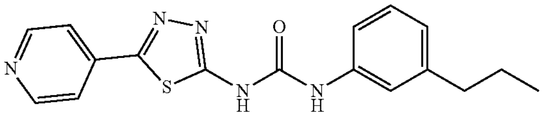 [SMILES: CCCc1cccc(NC(=O)Nc2nnc(-c3ccncc3)s2)c1] |
| A134 | 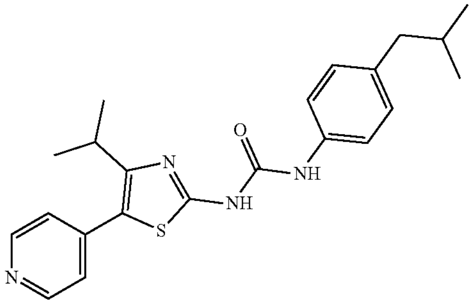 [SMILES: CC(C)Cc1ccc(NC(=O)Nc2nc(C(C)C)c(-c3ccncc3)s2)cc1] |
| A135 | 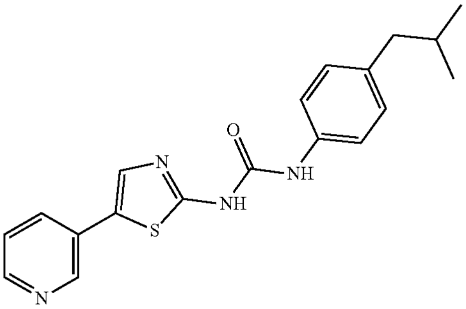 [SMILES: CC(C)Cc1ccc(NC(=O)Nc2ncc(-c3cccnc3)s2)cc1] |
| A136 | 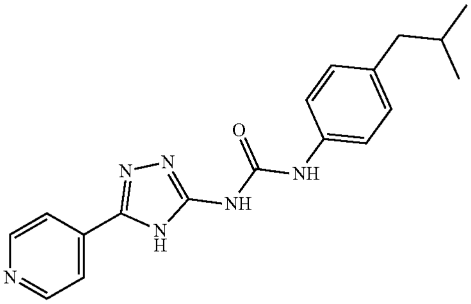 [SMILES: CC(C)Cc1ccc(NC(=O)Nc2nnc(-c3ccncc3)[nH]2)cc1] |
| A137 | 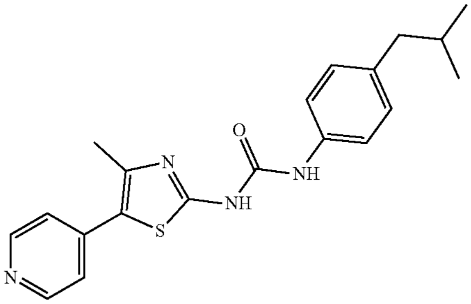 [SMILES: Cc1nc(NC(=O)Nc2ccc(CC(C)C)cc2)sc1-c1ccncc1] |

TABLE A-continued
| ID | STRUCTURE |
|---|---|
| A138 | 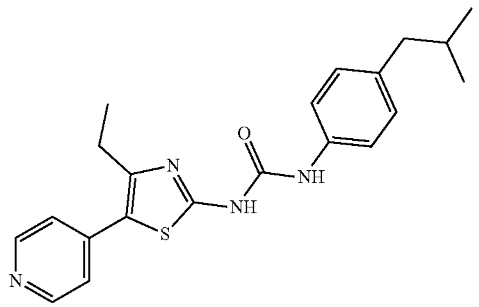 [SMILES: CCc1nc(NC(=O)Nc2ccc(CC(C)C)cc2)sc1-c1ccncc1] |
| A139 | 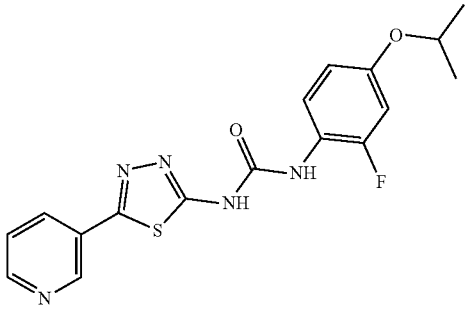 [SMILES: CC(C)Oc1ccc(NC(=O)Nc2nnc(-c3cccnc3)s2)c(F)c1] |
| A140 | 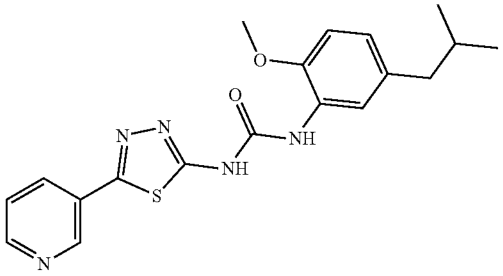 [SMILES: COc1ccc(CC(C)C)cc1NC(=O)Nc1nnc(-c2cccnc2)s1] |
| A141 | 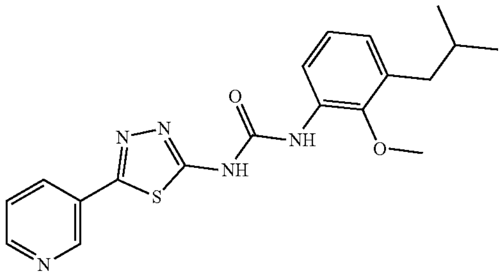 [SMILES: COc1c(CC(C)C)cccc1NC(=O)Nc1nnc(-c2cccnc2)s1] |
| A142 | 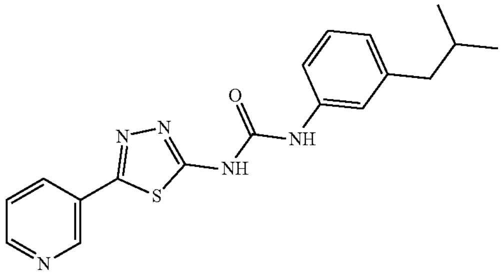 [SMILES: CC(C)Cc1cccc(NC(=O)Nc2nnc(-c3cccnc3)s2)c1] |

TABLE A-continued
| ID | STRUCTURE |
|---|---|
| A143 | 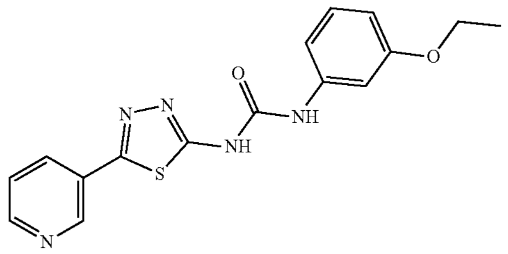 [SMILES: CCOc1cccc(NC(=O)Nc2nnc(-c3cccnc3)s2)c1] |
| A144 | 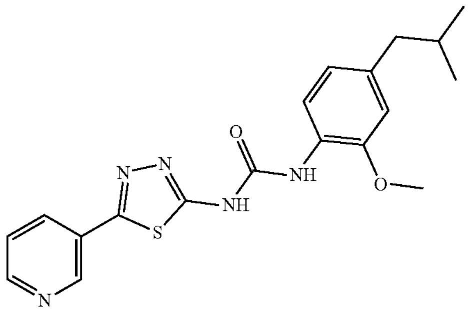 [SMILES: COc1cc(CC(C)C)ccc1NC(=O)Nc1nnc(-c2cccnc2)s1] |
| A145 | 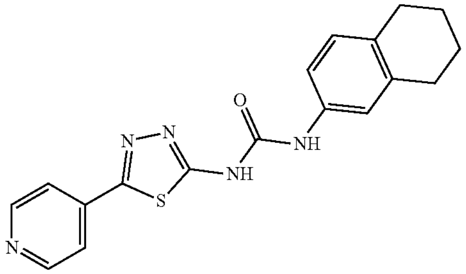 [SMILES: O=C(Nc1ccc2c(c1)CCCC2)Nc1nnc(-c2ccncc2)s1] |
| A146 | 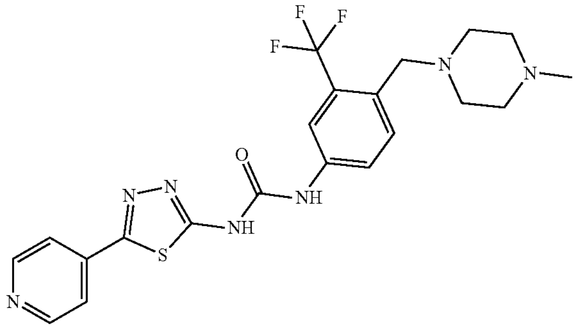 [SMILES: CN1CCN(Cc2ccc(NC(=O)Nc3nnc(-c4ccncc4)s3)cc2C(F)(F)F)CC1] |
| A147 | 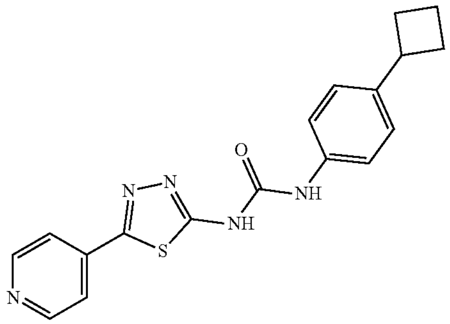 [SMILES: O=C(Nc1ccc(C2CCC2)cc1)Nc1nnc(-c2ccncc2)s1] |

TABLE A-continued
| ID | STRUCTURE |
|---|---|
| A148 | 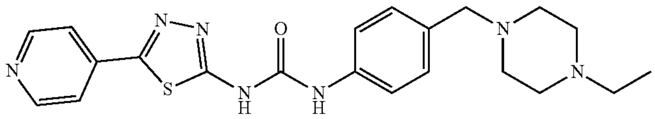 [SMILES: CCN1CCN(Cc2ccc(NC(=O)Nc3nnc(-c4ccncc4)s3)cc2)CC1] |
| A149 | 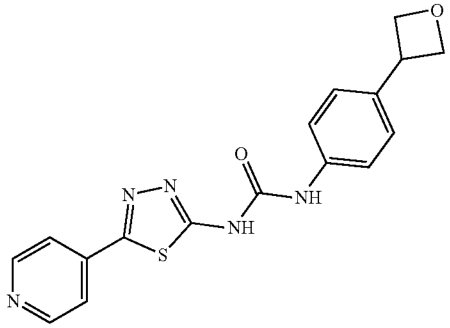 [SMILES: O=C(Nc1ccc(C2COC2)cc1)Nc1nnc(-c2ccncc2)s1] |
| A150 | 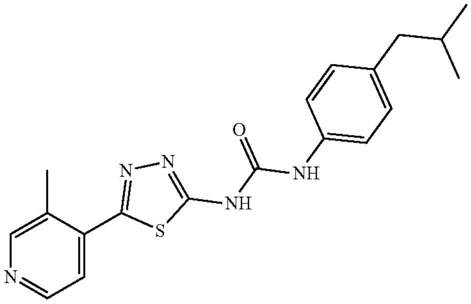 [SMILES: Cc1cnccc1-c1nnc(NC(=O)Nc2ccc(CC(C)C)cc2)s1] |
| A151 | 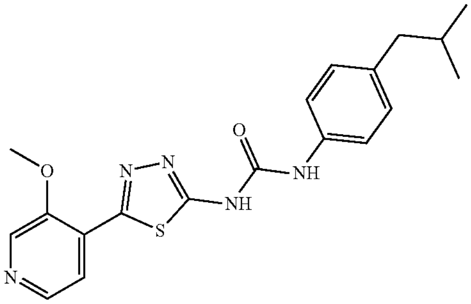 [SMILES: COc1cnccc1-c1nnc(NC(=O)Nc2ccc(CC(C)C)cc2)s1] |
| A152 | 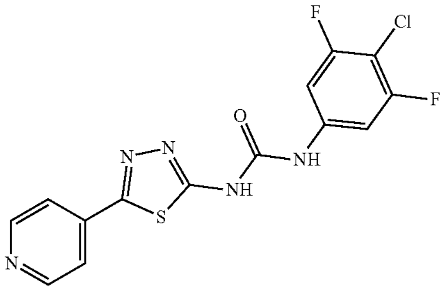 [SMILES: O=C(Nc1cc(F)c(Cl)c(F)c1)Nc1nnc(-c2ccncc2)s1] |

TABLE A-continued
| ID | STRUCTURE |
| --- | --- |
| A153 | 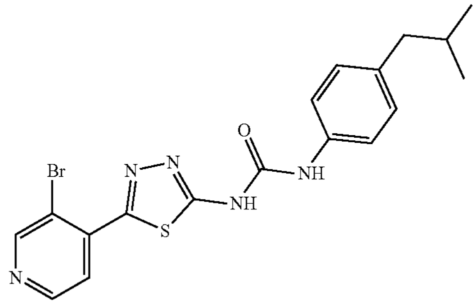 [SMILES: CC(C)Cc1ccc(NC(=O)Nc2nnc(-c3ccncc3Br)s2)cc1] |
| A154 | 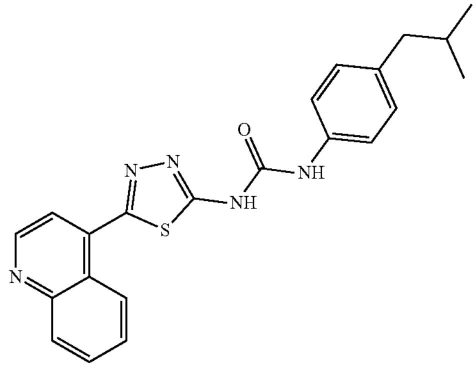 [SMILES: CC(C)Cc1ccc(NC(=O)Nc2nnc(-c3ccnc4ccccc34)s2)cc1] |
| A155 | 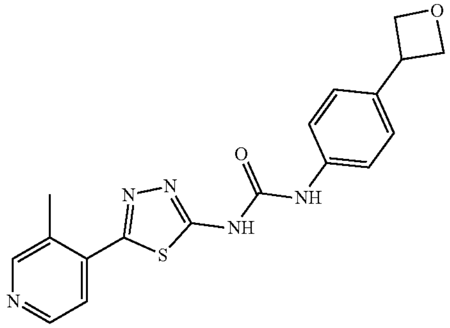 [SMILES: Cc1cnccc1-c1nnc(NC(=O)Nc2ccc(C3COC3)cc2)s1] |
| A156 | 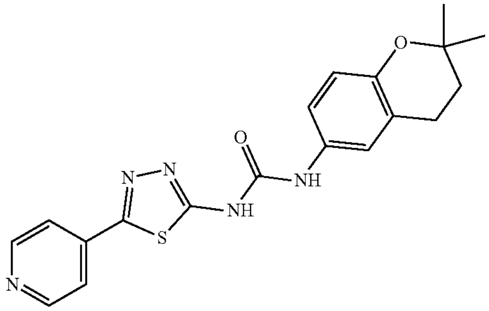 [SMILES: CC1(C)CCc2cc(NC(=O)Nc3nnc(-c4ccncc4)s3)ccc2O1] |
| A157 | 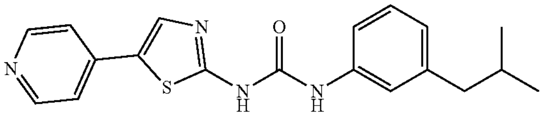 [SMILES: CC(C)Cc1cccc(NC(=O)Nc2ncc(-c3ccncc3)s2)c1] |
| A158 | 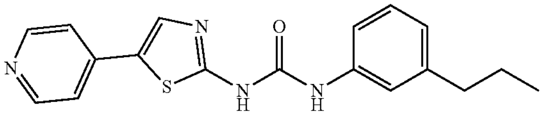 |

TABLE A-continued
| ID | STRUCTURE |
| --- | --- |
| A159 | 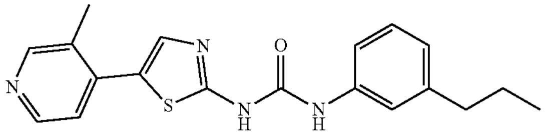 [SMILES: CCCc1cccc(NC(=O)Nc2ncc(-c3ccncc3C)s2)c1] |
| A160 | 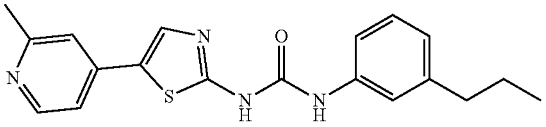 [SMILES: CCCc1cccc(NC(=O)Nc2ncc(-c3ccnc(C)c3)s2)c1] |
| A161 | 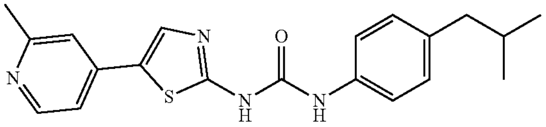 [SMILES: Cc1cc(-c2cnc(NC(=O)Nc3ccc(CC(C)C)cc3)s2)ccn1] |
| A162 | 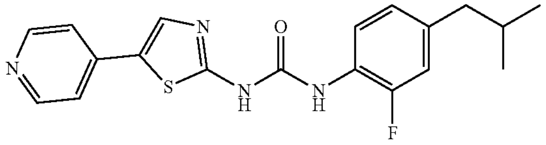 [SMILES: CC(C)Cc1ccc(NC(=O)Nc2ncc(-c3ccncc3)s2)c(F)c1] |
| A163 | 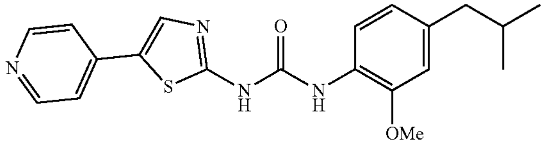 [SMILES: COc1cc(CC(C)C)ccc1NC(=O)Nc1ncc(-c2ccncc2)s1] |
| A164 | 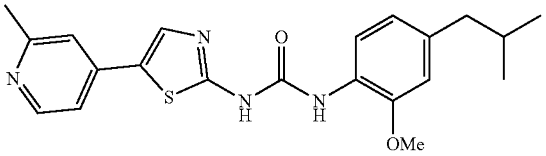 [SMILES: COc1cc(CC(C)C)ccc1NC(=O)Nc1ncc(-c2ccnc(C)c2)s1] |
| A165 | 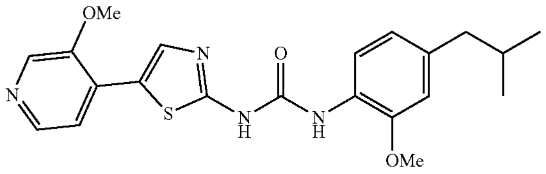 [SMILES: COc1cc(CC(C)C)ccc1NC(=O)Nc1ncc(-c2ccncc2OC)s1] |
| A166 | 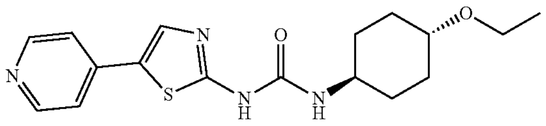 |
| A167 | 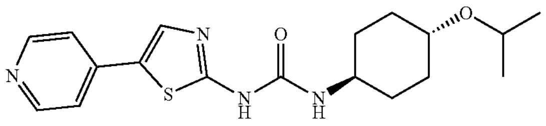 [SMILES: CC(C)O[C@H]1CC[C@H](NC(=O)Nc2ncc(-c3ccncc3)s2)CC1] |
| A168 | 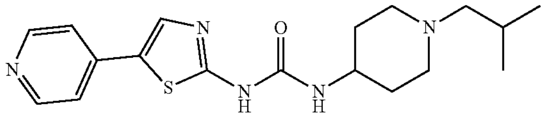 [SMILES: CC(C)CN1CCC(NC(=O)Nc2ncc(-c3ccncc3)s2)CC1] |

TABLE A-continued

| ID | STRUCTURE |
| --- | --- |
| A169 | 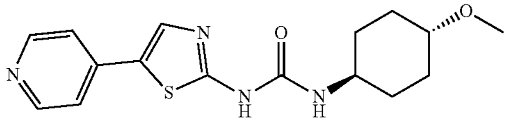 [SMILES: CO[C@H]1CC[C@H](NC(=O)Nc2ncc(-c3ccncc3)s2)CC1] |

Also provided herein are compounds, or pharmaceutically acceptable salts thereof, having a structure as shown in Table B.

TABLE B

| ID | STRUCTURE |
| --- | --- |
| B61 | 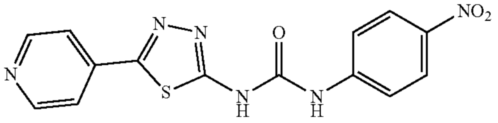 [SMILES: O=C(Nc1ccc([N+](=O)[O-])cc1)Nc1nnc(-c2ccncc2)s1] |
| B64 | 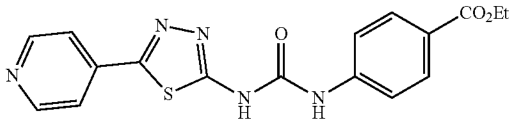 [SMILES: CCOC(=O)c1ccc(NC(=O)Nc2nnc(-c3ccncc3)s2)cc1] |
| B82 | 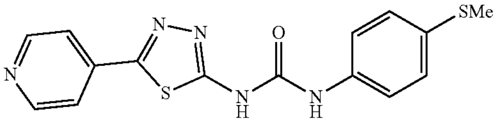 [SMILES: CSc1ccc(NC(=O)Nc2nnc(-c3ccncc3)s2)cc1] |
| B68 | 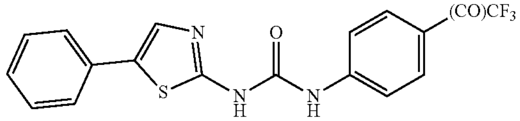 |
| B69 | 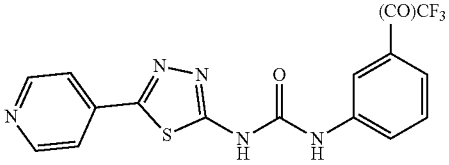 |
| B71 | 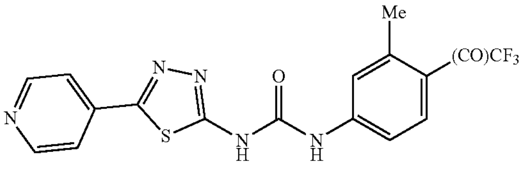 |
| B72 | 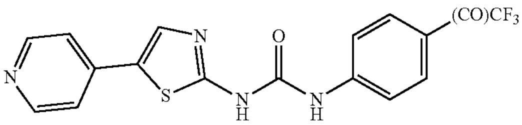 |
| B89 | 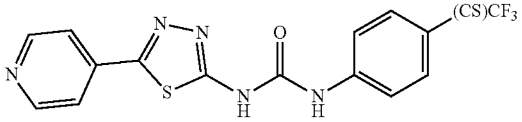 |

TABLE B-continued

| ID | STRUCTURE |
| --- | --- |
| B95 | 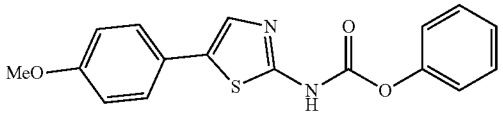 [SMILES: COc1ccc(-c2cnc(NC(=O)Oc3ccccc3)s2)cc1] |
| B97 | 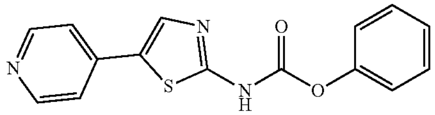 [SMILES: O=C(Nc1ncc(-c2ccncc2)s1)Oc1ccccc1] |
| B80 | 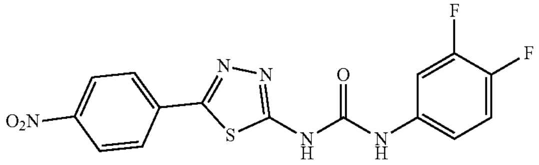 [SMILES: O=C(Nc1ccc(F)c(F)c1)Nc1nnc(-c2ccc([N+](=O)[O-])cc2)s1] |

In some embodiments, the compound or pharmaceutically acceptable salt thereof is selected from compound A1, A2, A3, A4, and A5. In some embodiments, the compound or pharmaceutically acceptable salt thereof is selected from compound A2, A3, A4, A5, A58, A62, A64, B82, A68, A1, A78, and A81. In some embodiments, the compound or pharmaceutically acceptable salt thereof is selected from compound A1, A2, A3, A4, A5, and A64. In some embodiments, the compound or pharmaceutically acceptable salt thereof is selected from compound A1, A2, A3, A4, A5, A52, and A81. In some embodiments, the compound or pharmaceutically acceptable salt thereof is compound A1. In some embodiments, the compound or pharmaceutically acceptable salt thereof is compound A2. In some embodiments, the compound or pharmaceutically acceptable salt thereof is compound A3. In some embodiments, the compound or pharmaceutically acceptable salt thereof is compound A4. In some embodiments, the compound or pharmaceutically acceptable salt thereof is compound A5. In some embodiments, the compound or pharmaceutically acceptable salt thereof is compound A52. In some embodiments, the compound or pharmaceutically acceptable salt thereof is compound A64. In some embodiments, the compound or pharmaceutically acceptable salt thereof is compound A81.

The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds described herein or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This disclosure also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that this disclosure includes mixtures/combinations of different pharmaceutically acceptable salts and also mixtures/combinations of compounds in free form and pharmaceutically acceptable salts.

Preparation of Compounds Disclosed Herein

Synthesis of the compounds described herein can be done using any suitable method. The present disclosure also provides methods of preparing a compound described herein. The compounds described herein, and pharmaceutical salts thereof, all include a core structure (e.g., a thiazole/thiadiazole moiety) linking ring A to a urea/thiourea moiety, which is linked to ring B.

One method that is used to synthesize the disclosed compounds is "Method A". Briefly, the Method A synthesis includes reacting the ring A-thiazole/thiadiazole compound (free amine) with the desired isocyanate of ring B to provide the desired compound of formula (I), which is then purified using standard techniques.

An illustrative procedure using Method A to prepare a substituted 1-phenyl-(5-(pyridyl)-1,3,4-thiadiazol-2-yl)-urea compound or 1-phenyl-(5-(pyridyl)-1,3,4-thiazol-2-yl)-urea compound is described herein. 2-Amino-5-(4-pyridinyl)-1,3,4-thiadiazole or 2-amino-5-(4-pyridinyl)-1,3,4-thiazole (1 mol. equiv.) was added to a solution of an isocyanatobenzene (1 mol. equiv.) in dichloromethane (0.1 M solution). The reaction was stirred at room temperature overnight, filtered and rinsed with dichloromethane. The precipitate was recrystallized in denatured ethanol, cooled on ice, filtered, and rinsed with ethanol and dried under vacuum to give the desired product.

Another method that is used to synthesize the disclosed compounds is "Method B". Briefly, the Method B synthesis includes reacting desired ring B moiety (free amine) with the desired carbamate of ring A-thiazole/thiadiazole compound to provide the desired compound of formula (I), which is then purified using standard techniques.

An illustrative procedure using Method B to prepare a substituted 1-phenyl-(5-(pyridyl)-1,3,4-thiadiazol-2-yl)urea compound or 1-phenyl-(5-(pyridyl)-1,3,4-thiazol-2-yl)-urea compound is described herein. 2-Amino-5-(4-pyridinyl)-1,3,4-thiadiazole or 2-amino-5-(4-pyridinyl)-1,3,4-thiazole (1 mol. equiv.) was suspended in pyridine (0.3 M solution) and cooled to 0° C. under an atmosphere of nitrogen. Phenyl carbonochloridate (1.5 mol. equiv.) was added dropwise and the solution was stirred at 0° C. for 30 min and then allowed to warm to room temperature. The reaction mixture was poured into a saturated solution of $NaHCO_3$ (50 mL) and extracted with ethyl acetate, washed with brine solution, dried ($MgSO_4$) and adsorbed to Celite®. Chromatography (ethyl acetate in hexanes, 2:1) provided the desired carbamates. Phenyl N-[5-(pyridyl)-1,3,4-thiadiazol-2-yl]carbamate or phenyl N-[5-(pyridyl)-1,3-thiazol-2-yl]carbamate (1 mol. equiv.) and an aniline (1.2 mol. equiv.) in dioxane (0.5 M solution) was placed in a sealed tube and heated at 100° C. overnight. The reaction mixture was suspended in denatured ethanol and filtered. The filtrate was resuspended in boiling ethanol, cooled with an ice bath, filtered and washed with ethanol. The filtrate was dried under vacuum to give the desired urea compounds.

Pharmaceutical Compositions

The compounds described herein can be formulated into pharmaceutical compositions that further comprise a pharmaceutically acceptable carrier, diluent, adjuvant or vehicle. In some embodiments, the present disclosure relates to a pharmaceutical composition comprising a compound described herein, and a pharmaceutically acceptable carrier, diluent, adjuvant or vehicle. In some embodiments, the present disclosure includes a pharmaceutical composition comprising a safe and effective amount of a compound described herein or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating an influenza virus infection in a patient. The term "prophylactically effective amount" refers to an amount effective in preventing and/or substantially lessening the chances or the size of influenza virus infection outbreak.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this disclosure. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Methods of Use

The compounds described herein or pharmaceutically acceptable salts thereof can be used to inhibit CDK19 activity, and thus can be used to treat conditions mediated by CDK19, such as cancer, more particularly, cancers wherein CDK19 activity plays a role (e.g., downregulation or inhibition of CDK19 activity). Suitable cancers which can be treated by the disclosed methods, include but are not limited to breast cancer, prostate cancer, cancer of the gastrointestinal tract (e.g., colorectal cancer), bladder cancer, sarcoma, cervical cancer, esophageal adenocarcinoma, acute myeloid leukemia, melanoma, and ovarian cancer. In some cases, the cancer is triple negative breast cancer.

As used herein, the terms "treat", "treatment," and "treating" refer to the reduction or amelioration of the progression, severity and/or duration of the CDK19 mediated condition (e.g., TNBC), or the amelioration of one or more symptoms (specifically, one or more discernible symptoms) of CDK19-mediated condition, resulting from the administration of one or more therapies (e.g., one or more therapeutic agents such as a compound or composition described herein).

As used herein, the term "inhibitor" as used in the context of CDK19, refers to a compound, or pharmaceutical composition that reduces the expression or activity of CDK19. Desirably, the compound or pharmaceutical composition selectively inhibits CDK19 expression or activity over that of CDK8.

As used here, the terms "decrease," "reduced," "reduction," and "decreasing" are all used herein to refer to a decrease by at least 10% as compared to a reference level, for example a decrease by at least about 5%, at least about 10%, at least about 20%, or at least about 30%, or at least about 40%, or at least about 50%, or at least about 60%, or at least about 70%, or at least about 80%, or at least about 90% or up to and including a 100% decrease (i.e., absent level as compared to a reference sample), or any decrease between 10-100% as compared to a reference level.

The disclosed compounds, or pharmaceutically acceptable salts thereof, are selective for CDK19 over other kinases (e.g., CDK8). For example, compounds of formula (I) when screened against a panel of other kinases (e.g., using KINOMEscan® assay), exhibit selectivity for inhibiting CDK19.

The inhibition of CDK19 activity can be measure by any suitable method known in the art. For example, any suitable enzyme inhibition assay (e.g., competitive binding assay) or functional cell-based assay can be used to measure CDK19 activity. An illustrative assay for measuring CDK19 activity is a FRET-based (Forster resonant energy transfer) assay.

In some embodiments, the disclosure provides a method of inhibiting cyclin dependent kinase 19 (CDK19) comprising contacting CDK19 with one or more of the disclosed compounds in an amount effective to inhibit CDK19.

In some embodiments, the disclosed compounds selectively inhibit CDK19 over CDK8. CDK8 inhibitory activity can be measured using any suitable inhibition assay, including FRET-based assays. In some embodiments, the compound is at least 2 times more selective for CDK19 over CDK8. For example, in some embodiments the compound is at least 3 times more selective for CDK19 (e.g., at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 times or more selective for CDK19 over CDK8).

In some embodiments, the compound has an $IC_{50}$ for CDK19 of less than 400 nM (e.g., 375, 350, 325, 300, 275, 250, 225 nm). In some embodiments, the compound has an $IC_{50}$ for CDK19 of less than 200 nM (e.g., 175, 150, 125, 100, 90, 80, 70, 60, 50, 40, 30, 20, 10, 5, 4, 3, 2, or less than 1 nM). In some embodiments, the compounds have an $IC_{50}$ for CDK19 of 20 nm. In some embodiments, the compounds haves an $IC_{50}$ for CDK19 of 2.5 nM.

In some embodiments, the disclosed compounds have a lethal dose 50 ($LD_{50}$) in a TNBC cell line of 500 nM or less (e.g., 500, 450, 400, 350, 300, 250, 200, 150, 100 nM or less). In some embodiments the disclosed compounds have a $LD_{50}$ in MDA-MB-231 TNBC cells of 180 nM, 178 nM, 158 nM, or 91 nM. In some embodiments, the disclosed compounds have a $LD_{50}$ in normal cells (e.g., human foreskin fibroblast cells) of 1,000 nM or more (e.g., 1,000, 1,500, 2,000, 2,500, 5,000, 7,500, 10,000 nM or more). In some embodiments, the disclosed compounds have a $LD_{50}$ in human foreskin fibroblast cells of greater than 10,000 nM. Illustrative $LD_{50}$ measurements are described herein at the Examples.

In some embodiments, the disclosure provides a method of treating a tumor expressing aberrant CD19 levels (e.g., breast cancer, or more specifically, triple negative breast cancer) in a patient comprising administering to the patient a therapeutically effective amount of a compound disclosed herein. In some embodiments, the disclosure provides a method of treating breast cancer in a patient comprising administering to the patient a therapeutically effective amount of a compound disclosed herein. In some embodiments, the treatment results in an at least 10% reduction in tumor volume. In some cases, the reduction in tumor volume is at least 20%, at least 25%, at least 30%, at least 40%, or at least 50%. The reduction can occur within 12 months of initiating therapy, within 11 months, within 10 months, within 9 months, within 8 months, within 7 months, within 6 months, within 5 months, within 4 months, within 3 months, within 2 months, or within 1 month of initiating therapy.

As used herein, the term "patient" (e.g., subject) refers to an animal, specifically a "mammal" including a non-primate (e.g., a cow, pig, horse, sheep, rabbit, guinea pig, rat, cat, dog, or mouse) and a primate (e.g., a monkey, chimpanzee, or human), and more specifically a human. In a preferred embodiment, the patient is a "human".

As used herein, an "effective amount" refers to an amount sufficient to elicit the desired biological response. As used herein, a "safe and effective amount" of a compound or composition described herein is an effective amount of the compound or composition which does not cause excessive or deleterious side effects in a patient.

As described in the Examples, when cells from a TNBC cell line (e.g., MDA-MB-231) are treated with a compound as disclosed herein, the treated cells undergo cell cycle arrest and apoptosis. In contrast, when a normal human fibroblast cell line (e.g., human foreskin fibroblast 2088 cells) are treated in the same manner, the treated cells continue to proliferate in a healthy manner. Thus, the compounds disclosed herein can selectively target a cancer cell in the presence of a healthy cell, which indicates a likelihood that healthy cells are not impacted, or minimally impacted, by the compound.

In some embodiments, the disclosure provides a method of treating cancer in patient comprising administering to the patient a therapeutically effective amount of the compound, tautomer, or salt of the disclosure. In some embodiments, the cancer is breast cancer, prostate cancer, cancer of the gastrointestinal tract (e.g., colorectal cancer), bladder cancer, sarcoma, cervical cancer, esophageal adenocarcinoma, acute myeloid leukemia, melanoma, glioma, or ovarian cancer. In some embodiments, the cancer is breast cancer. In some embodiments, the disclosure provides a method of treating a patient having triple negative breast cancer comprising administering a therapeutically effective dose of a compound or pharmaceutical composition that inhibits expression or activity of cyclin-dependent kinase 19 (CDK19).

In some embodiments, the disclosure provides a method of inhibiting cyclin dependent kinase 19 (CDK19) comprising contacting CDK19 with one or more of the compounds as disclosed herein in an amount effective to inhibit CDK19. In some cases, the compound is a compound as recited in Table C.

TABLE C

| | |
|---|---|
| A170 | 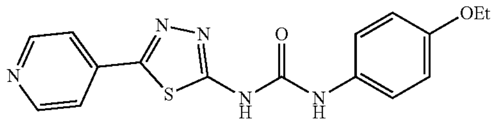 [SMILES: CCOc1ccc(NC(=O)Nc2nnc(-c3ccncc3)s2)cc1] |

TABLE C-continued

A171

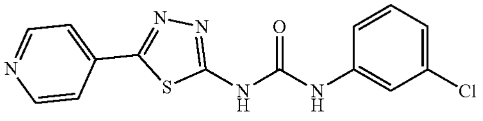 [SMILES: O=C(Nc1cccc(Cl)c1)Nc1nnc(-c2ccncc2)s1]

A172

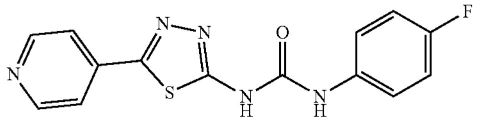 [SMILES: O=C(Nc1ccc(F)cc1)Nc1nnc(-c2ccncc2)s1]

A173

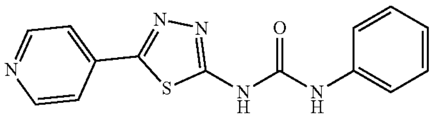 [SMILES: O=C(Nc1ccccc1)Nc1nnc(-c2ccncc2)s1]

A174

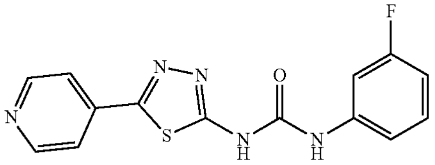 [SMILES: O=C(Nc1cccc(F)c1)Nc1nnc(-c2ccncc2)s1]

A175

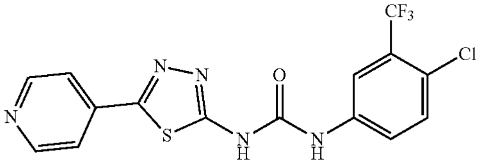 [SMILES: O=C(Nc1ccc(Cl)c(C(F)(F)F)c1)Nc1nnc(-c2ccncc2)s1]

A176

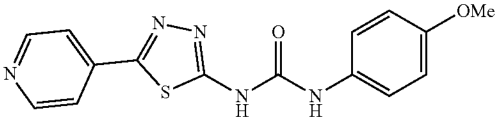 [SMILES: COc1ccc(NC(=O)Nc2nnc(-c3ccncc3)s2)cc1]

A177

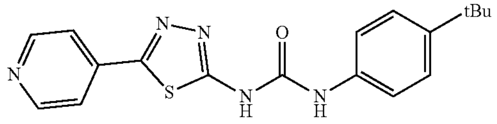

A178

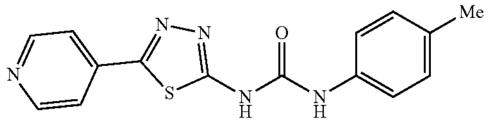

A179

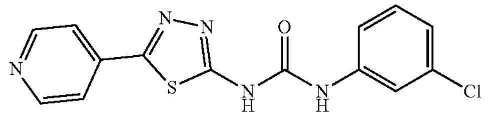 [SMILES: O=C(Nc1cccc(Cl)c1)Nc1nnc(-c2ccncc2)s1]

A180

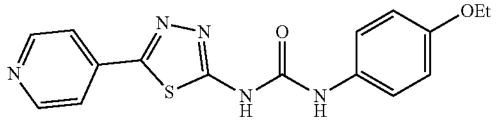 [SMILES: CCOc1ccc(NC(=O)Nc2nnc(-c3ccncc3)s2)cc1]

Combination Therapy

A compound described herein, or a pharmaceutically acceptable salt thereof, can be administered alone or in combination with an additional suitable therapy, for example, a second therapeutic agent, such as an anticancer agent.

Thus, in some embodiments, the patient undergoes one or more additional therapies in addition to treatment with a compound as disclosed herein.

When combination therapy is employed, a safe and effective amount can be achieved using a first amount of a compound as disclosed herein, or a pharmaceutically acceptable salt thereof, and a second amount of an additional suitable therapeutic agent (e.g. an anticancer agent).

In some embodiments, the second therapy is selected from chemotherapy, radiation therapy, surgery, and a combination thereof. In some embodiments, the second therapy comprises surgery to remove breast tissue.

EMBODIMENTS

1. A compound, or pharmaceutically acceptable salt thereof, having a structure of formula (I):

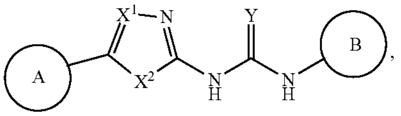

wherein:

ring A comprises a $C_6$-$C_{10}$aryl, a $C_3$-$C_{10}$cycloalkyl, a $C_5$-$C_{10}$heterocycloalkyl having 1-4 ring heteroatoms independently selected from N, O, S, or a 5-10 membered heteroaryl having 1-4 ring heteroatoms selected from N, O, and S, and ring A is optionally substituted with 1-2 $R^A$;

ring B comprises a $C_6$-$C_{10}$aryl or a 5-10 membered heteroaryl having 1-4 ring heteroatoms selected from N, O, and S, and ring B is optionally substituted with 1-3 $R^B$;

each $R^A$ is independently selected from the group consisting of $C_1$-$C_6$alkyl, $C_1$-$C_6$haloalkyl, $C_3$-$C_6$cycloalkyl, $C_1$-$C_6$alkoxy, $C_1$-$C_6$haloalkoxy, $C_1$-$C_3$alkylene-$C_6$-$C_{10}$aryl, cyano, halo, nitro,

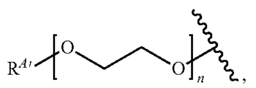

$C_1$-$C_3$alkylene-$C_5$-$C_{10}$heterocycloalkyl having 1-4 ring heteroatoms independently selected from N, O, S, and a 5-10 membered cycloheteroalkyl having 1-4 heteroatoms selected from N, O, and S;

$R^{A'}$ is $C_1$-$C_3$alkyl;

n is 1-5;

each $R^B$ is independently selected from the group consisting of $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_3$-$C_6$cycloalkoxy, $C_1$-$C_3$alkylene-$C_3$-$C_6$cycloalkyl, $C_1$-$C_3$alkylene-$C_6$-$C_{10}$aryl, —O—$C_1$-$C_3$alkylene-$C_6$-$C_{10}$aryl, —O—$C_1$-$C_3$alkylene-$C_1$-$C_6$alkoxy, —C(O)O$R^{B'}$, —S$R^{B'}$, —C(Z)$C_1$-$C_3$haloalkyl, —CN, nitro, halo, —$C_1$-$C_3$alkylene-O$R^{B'}$, —$C_1$-$C_3$alkylene-$C_6$-$C_{10}$heterocycloalkyl having 1-4 ring hetereoatoms independently selected from N, O, S, and —$C_1$-$C_3$alkylene-$C_5$-$C_6$heteroaryl having 1-4 ring heteroatoms independently selected from N, O, S;

or two ortho $R^B$ taken together with the atoms to which they are attached form a 5 or 6 membered cycloalkyl or a 5 or 6 membered cycloheteroalkyl comprising 1-3 ring heteroatoms independently selected from N, O, S;

$R^{B'}$ is H, $C_1$-$C_3$alkyl, or $C_1$-$C_6$haloalkyl;

Z IS O OR S; $X^1$ is N or $CR^1$, and $R^1$ is H or $C_1$-$C_6$alkyl;

$X^2$ is NH, O, or S;

Y is O or S; and with the proviso that (a) when ring A is unsubstituted 4-pyridinyl, Y is O, and $X^1$ is N and $X^2$ is S, ring B is not: phenyl, 2-fluorophenyl, 2-chlorophenyl, 2-methoxyphenyl, 3-fluorophenyl, 3-chlorophenyl, 3-cyanophenyl, 3-methylphenyl, 3-methoxyphenyl, 4-methylphenyl, 4-cyanophenyl, 4-methoxyphenyl, 4-ethoxyphenyl, 4-bromophenyl, 4-chlorophenyl, 4-fluorophenyl, 4-tert-butylphenyl, 2,3-dichlorophenyl, 2,4-dichlorophenyl, 2,4-difluorophenyl, 2,5-dimethoxyphenyl, 3,4-dimethylphenyl, 3,4-dichlorophenyl, 3,4-dibromophenyl, 3,4-difluorophenyl, 3-chloro-4-cyanophenyl, 3-bromo-4-cyanophenyl, 3-cyano-4-fluorophenyl, 3-fluoro-4-(trifluoromethyl)phenyl, 4-bromo-3-cyanophenyl, 4-bromo-3-methylphenyl, 4-bromo-3-(trifluoromethyl)phenyl, 4-chloro-3-cyanophenyl, 4-chloro-3-methylphenyl, 4-chloro-3-(trifluoromethyl)phenyl, 4-cyano-3-methylphenyl, 4-cyano-3-(trifluoromethyl)phenyl, 4-fluoro-3-(trifluoromethyl)phenyl, or 5-chloro-2-methoxyphenyl, (b) when ring A is unsubstituted 4-pyridinyl, Y is O, and $X^1$ is CH and $X^2$ is S, ring B is not: 3,4-dichlorophenyl or 2-chlorophenyl, and (c) when ring A is unsubstituted 3-pyridinyl, Y is O, and $X^1$ is N and $X^2$ is S, ring B is not: phenyl, 2-chlorophenyl, 2-fluorophenyl, 3-methylphenyl, 4-methylphenyl, 4-isopropylphenyl, 4-methoxyphenyl, 4-chlorophenyl, 4-bromophenyl, 4-fluorophenyl, 2,3-dichlorophenyl, 2,4-dimethylphenyl, 3,4-dimethylphenyl, 3,4-dichlorophenyl, 3-chloro-4-fluorophenyl, or naphthyl.

2. The compound or salt of embodiment 1, wherein ring A comprises a 5-10 membered heteroaryl having 1-3 ring heteroatoms selected from N, O, and S, and ring A is optionally substituted with 1-2 $R^A$ 3. The compound or salt of embodiment 1 or 2, wherein ring A comprises pyridinyl substituted with 1-2 $R^A$.

4. The compound or salt of embodiment 3, wherein the pyridinyl comprises a 3-pyridinyl.

5. The compound or salt of embodiment 3, wherein the pyridinyl comprises a 4-pyridinyl.

6. The compound or salt of any one of embodiments 1-5, wherein at least one $R^A$ is $C_1$-$C_6$alkyl, $C_3$-$C_6$cycloalkyl, or halo.

7. The compound or salt of embodiment 6, wherein ring A is selected from the group consisting of 3-methyl-4-pyridinyl, 3-ethyl-4-pyridinyl, 3-isopropyl-4-pyridinyl, 3-cyclopropyl-4-pyridinyl, 3,5-dimethyl-4-pyridinyl, 3-methyl-3-pyridinyl, 4-methyl-3-pyridinyl, and 5-chloro-3-pyridinyl.

8. The compound or salt of embodiment 1 or 2, wherein ring A comprises quinolinyl.

9. The compound or salt of embodiment 8, wherein ring A comprises 4-quinolinyl.

10. The compound or salt of embodiment 1, wherein ring A comprises a $C_6$-$C_{10}$aryl.

11. The compound or salt of embodiment 10, wherein ring A comprises a phenyl.

12. The compound or salt of embodiment 10, wherein ring A comprises a furanyl.

13. The compound or salt of embodiment 1, wherein ring A comprises a $C_3$-$C_{10}$cycloalkyl.

14. The compound or salt of embodiment 13, wherein ring A comprises a cyclohexyl.

15. The compound or salt of embodiment 13, wherein ring A comprises a cyclopropyl.

16. The compound or salt of embodiment 13, wherein ring A comprises adamantyl.

17. The compound or salt of embodiment 1, wherein ring A comprises a $C_5$-$C_{10}$heterocycloalkyl having 1-4 ring heteroatoms independently selected from N, O, S.

18. The compound or salt of embodiment 17, wherein ring A comprises morpholinyl.

19. The compound or salt of embodiment 17, wherein ring A comprises tetrahydrofuranyl.

20. The compound or salt of any one of embodiments 1-19, wherein each $R^A$ is independently selected from the group consisting of $C_1$-$C_6$alkyl, $C_1$-$C_6$haloalkyl, $C_3$-$C_6$cycloalkyl, $C_1$-$C_6$alkoxy, $C_1$-$C_6$haloalkoxy, cyano, and halo.

21. The compound or salt of embodiment 20, wherein $R^A$ is $C_1$-$C_6$ alkyl.

22. The compound or salt of embodiment 21, wherein $R^A$ is methyl.

23. The compound or salt of embodiment 20, wherein $R^A$ is $C_1$-$C_6$alkoxy.

24. The compound or salt of embodiment 23, wherein $R^A$ is methoxy.

25. The compound or salt of embodiment 23, wherein $R^A$ is hexoxy.

26. The compound or salt of any one of embodiments 1-19, wherein $R^A$ is nitro.

27. The compound or salt of any one of embodiments 1-19, wherein $R^A$ is

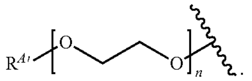

28. The compound or salt of embodiment 27, wherein n is 3

29. The compound or salt of embodiment 27 or 28, wherein $R^{A'}$ is methyl.

30. The compound or salt of any one of embodiments 1-19, wherein $R^A$ is a $C_1$-$C_3$alkylene-$C_5$-$C_{10}$heterocycloalkyl having 1-4 ring heteroatoms independently selected from N, O, S.

31. The compound or salt of embodiment 30, wherein $R^A$ is morpholino-methyl.

32. The compound or salt of any one of embodiments 1-19, wherein $R^A$ is a 5-10 membered cycloheteroalkyl having 1-4 heteroatoms selected from N, O, and S.

33. The compound or salt of embodiment 32, wherein $R^A$ is morpholinyl.

34. The compound or salt of embodiment 1, wherein ring A is selected from the group consisting of

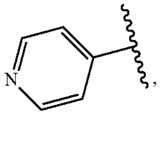, 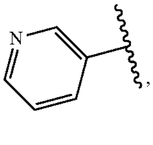, 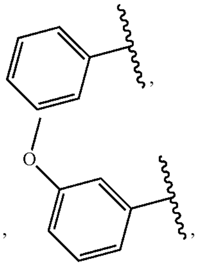,

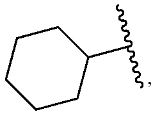, 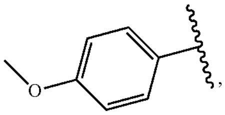,

-continued

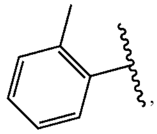, 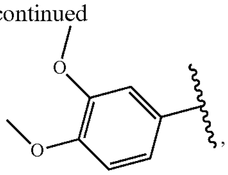,

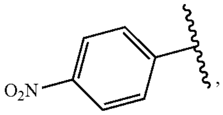, 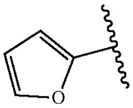, 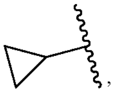,

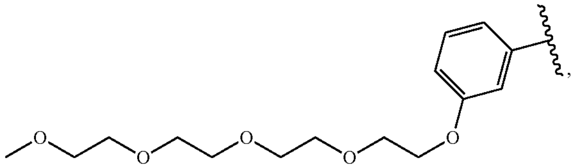,

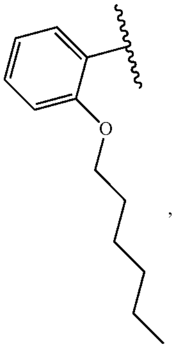, 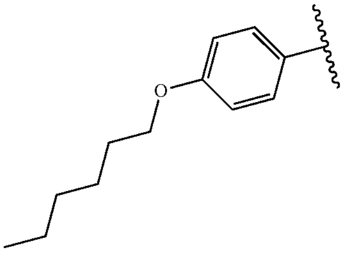,

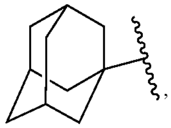, 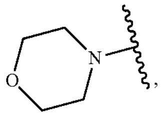, 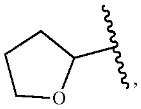,

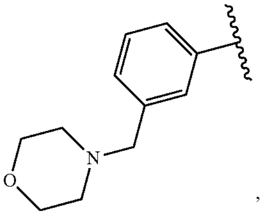, 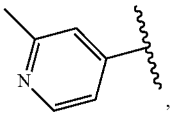,

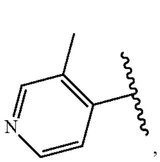, 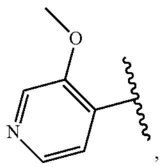, 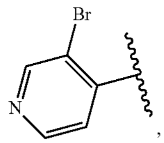, and

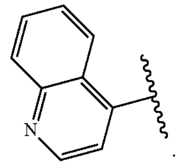.

35. The compound or salt of any one of embodiments 1-34, wherein ring B comprises a $C_6$-$C_{10}$aryl.

36. The compound or salt of embodiment 35, wherein ring B comprises phenyl.

37. The compound or salt of embodiment 35, wherein ring B comprises naphthyl.

38. The compound or salt of any one of embodiments 1-34, wherein ring B comprises a 5-10 membered heteroaryl having 1-4 ring heteroatoms selected from N, O, and S.

39. The compound or salt of embodiment 38, wherein ring B comprises quinolinyl.

40. The compound or salt of embodiment 39, wherein ring B comprises 8-quinolinyl.

41. The compound or salt of any one of embodiments 1-40, wherein $R^B$ is halo.

42. The compound or salt of embodiment 41, wherein $R^B$ is fluoro, chloro, or bromo.

43. The compound or salt of any one of embodiments 1-40, wherein $R^B$ is $C_1$-$C_6$aryl.

44. The compound or salt of embodiment 43, wherein $R^B$ is phenyl.

45. The compound or salt of any one of embodiments 1-40, wherein $R^B$ is $C_1$-$C_6$haloalkyl.

46. The compound or salt of embodiment 45, wherein $R^B$ is trifluoromethyl.

47. The compound or salt of any one of embodiments 1-40, wherein $R^B$ is nitro.

48. The compound or salt of any one of embodiments 1-40, wherein $R^B$ is $C_1$-$C_6$alkoxy.

49. The compound or salt of embodiment 48, wherein $R^B$ is selected from the group consisting of methoxy, ethoxy, isopropoxy, and isobutoxy.

50. The compound or salt of any one of embodiments 1-40, wherein $R^B$ is —C(O)O$R^{B'}$.

51. The compound or salt of embodiment 50, wherein $R^{B'}$ is methyl or ethyl.

52. The compound or salt of any one of embodiments 1-40, wherein $R^B$ is $C_1$-$C_3$alkylene-$C_6$-$C_{10}$aryl.

53. The compound or salt of embodiment 52, wherein $R^B$ is benzyl.

54. The compound or salt of any one of embodiments 1-40, wherein $R^B$ is $C_1$-$C_6$haloalkoxy.

55. The compound or salt of embodiment 54, wherein $R^B$ is selected from the group consisting of trifluoromethoxy, difluoromethoxy, and 1,1-difluoro-2,2-difluoroethoxy.

56. The compound or salt of embodiment 55, wherein $R^B$ is difluromethoxy.

57. The compound or salt of any one of embodiments 1-40, wherein $R^B$ is —O—$C_1$-$C_3$alkylene-$C_6$-$C_{10}$aryl.

58. The compound or salt of embodiment 57, wherein $R^B$ is benzyloxy.

59. The compound or salt of any one of embodiments 1-40, wherein $R^B$ is $C_1$-$C_6$alkyl.

60. The compound or salt of embodiment 59, wherein $R^B$ is selected from the group consisting of methyl, ethyl, propyl, or isopropyl, butyl, isobutyl, sec-butyl, and tert-butyl.

61. The compound or salt of any one of embodiments 1-40, wherein $R^B$ is $C_3$-$C_6$cycloalkyl.

62. The compound or salt of embodiment 61, wherein $R^B$ is cyclopropyl or cyclobutyl.

63. The compound or salt of any one of embodiments 1-40, wherein $R^B$ is $C_3$-$C_6$cycloalkoxy.

64. The compound or salt of embodiment 61, wherein $R^B$ is cyclopropoxy or cyclobutoxy.

65. The compound or salt of any one of embodiments 1-40, wherein two ortho $R^B$ taken together with the atoms to which they are attached form a 5 or 6 membered cycloheteroalkyl comprising 1-3 ring heteroatoms independently selected from N, O, S.

66. The compound or salt of embodiment 65, wherein the two ortho $R^B$ form a 1,3-dioxolane.

67. The compound or salt of any one of embodiments 1-40, wherein $R^B$ is —S$R^{B'}$.

68. The compound or salt of embodiment 67, wherein $R^{B'}$ is methyl or trifluoromethyl.
69. The compound or salt of any one of embodiments 1-40, wherein $R^B$ is —$C_1$-$C_3$alkylene-$OR^{B'}$.
70. The compound or salt of embodiment 69, wherein $R^B$ is hydroxyethyl. 71. The compound or salt of any one of embodiments 1-40, wherein $R^B$ is —$C_1$-$C_3$alkylene-$C_5$-$C_6$heteroaryl having 1-4 ring heteroatoms independently selected from N, O, S.
72. The compound or salt of embodiment 71, wherein $R^B$ is (1,2,4-triazol-1-yl)methyl.
73. The compound or salt of any one of embodiments 1-40, wherein $R^B$ is —O—$C_1$-$C_3$alkylene-$C_1$-$C_6$alkoxy.
74. The compound or salt of embodiment 73, wherein $R^B$ is 2-methoxyethoxy.
75. The compound or salt of any one of embodiments 1-40, wherein $R^B$ is —CN.
76. The compound or salt of any one of embodiments 1-40, wherein $R^B$ is —$C_1$-$C_3$alkylene-$C_3$-$C_6$cycloalkyl.
77. The compound or salt of embodiment 76, wherein $R^B$ is cyclopropylmethyl.
78. The compound or salt of any one of embodiments 1-40, wherein two ortho $R^B$ taken together with the atoms to which they are attached form a 5 or 6 membered cycloalkyl.
79. The compound or salt of embodiment 78, wherein the two ortho $R^B$ form a cyclohexyl.
80. The compound or salt of any one of embodiments 1-40, wherein two ortho $R^B$ taken together with the atoms to which they are attached form a 5 or 6 membered cycloheteroalkyl comprising 1-3 ring heteroatoms independently selected from N, O, S.
81. The compound or salt of embodiment 80, wherein the two ortho $R^B$ form a 2,2-dimethylchromanyl.
82. The compound or salt of any one of embodiments 1-40, wherein $R^B$ is a $C_1$-$C_3$alkylene-$C_6$-$C_{10}$heterocycloalkyl having 1-4 ring hetereoatoms independently selected from N, O, S.
83. The compound or salt of embodiment 82, wherein $R^B$ is (4-methylpiperazin-1-yl)methyl.
84. The compound or salt of any one of embodiments 1-40, wherein $R^B$ is —C(Z)$C_1$-$C_3$haloalkyl.
85. The compound or salt of embodiment 84, wherein $R^B$ is —C(Z)$CF_3$.
86. The compound or salt of embodiment 84 or 85, wherein Z is O.
87. The compound or salt of embodiment 84 or 85, wherein Z is S.
88. The compound or salt of any one of embodiments 1-40, wherein each $R^B$ is independently selected from the group consisting of $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_1$-$C_3$alkylene-$C_3$-$C_6$cycloalkyl, cyano, and halo.
89. The compound or salt of any one of embodiments 1-34, wherein ring B is selected from the group consisting of

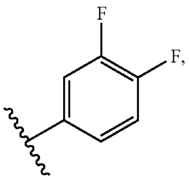 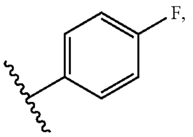 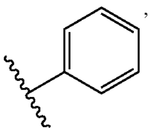 ,

-continued

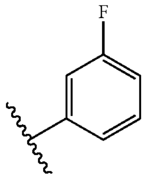 , 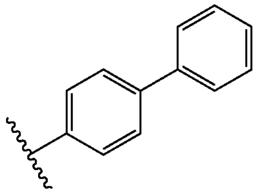 ,

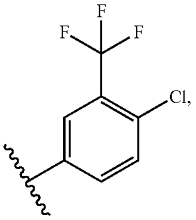 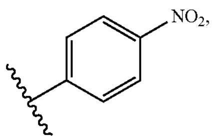

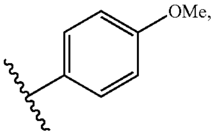 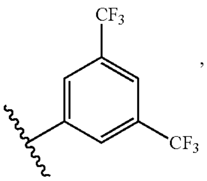 ,

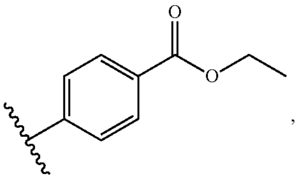 ,

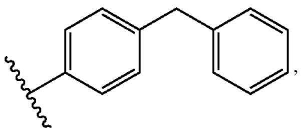 , 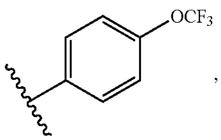 ,

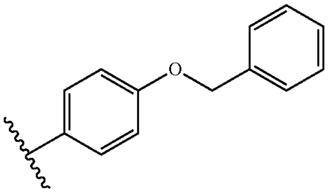 , 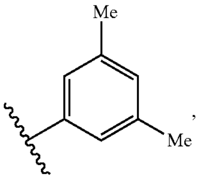 ,

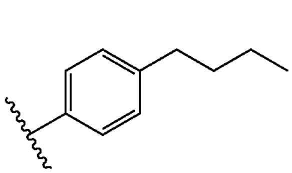 , 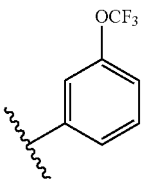 ,

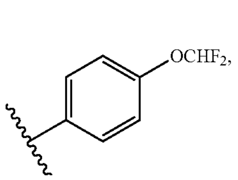 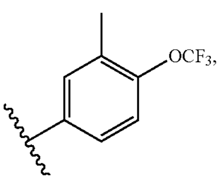

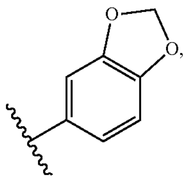 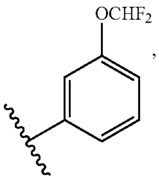 ,

-continued
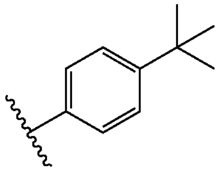, 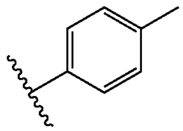,
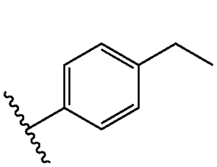, 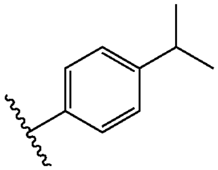,
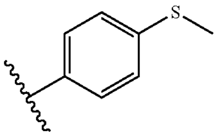, 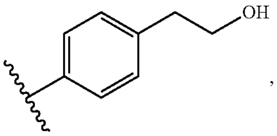,
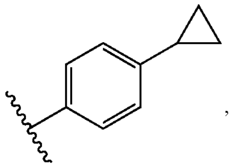, 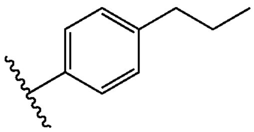,
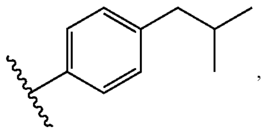, 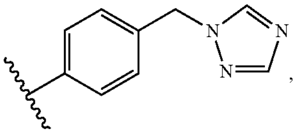,
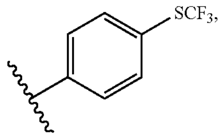 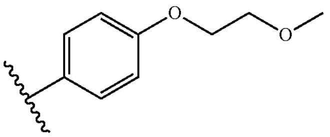,
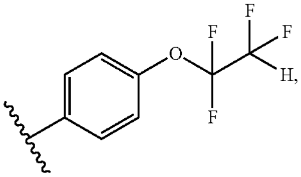 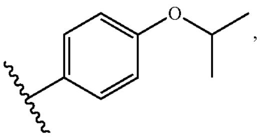,
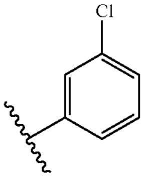, 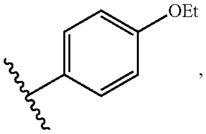,
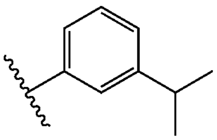, 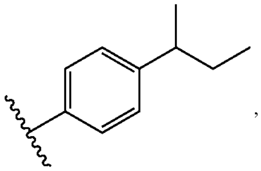,
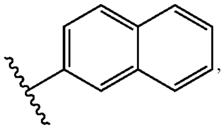, 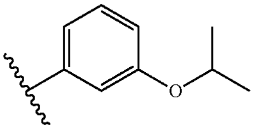,
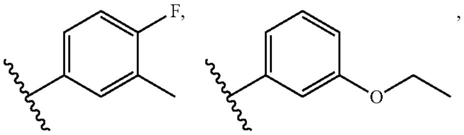,
-continued
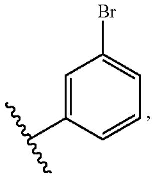, 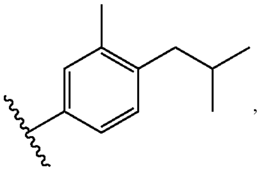,
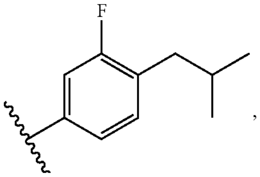, 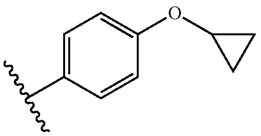,
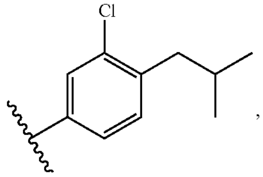, 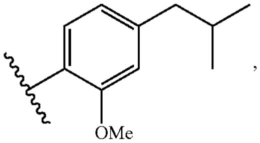,
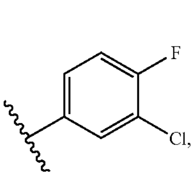 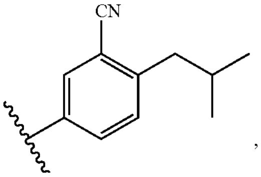,
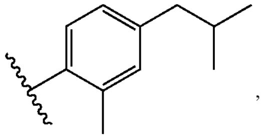, 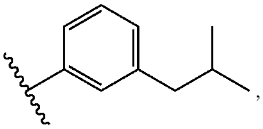,
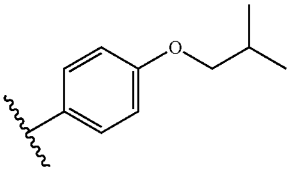, 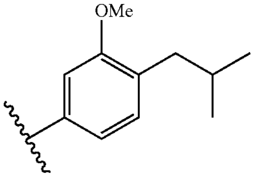,
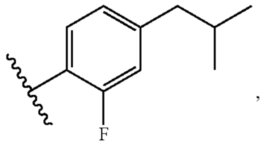, 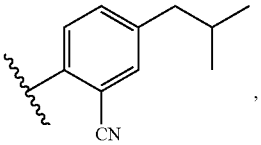,
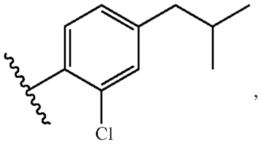, 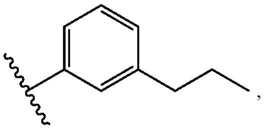,
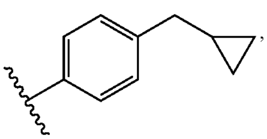, 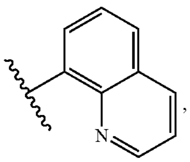,
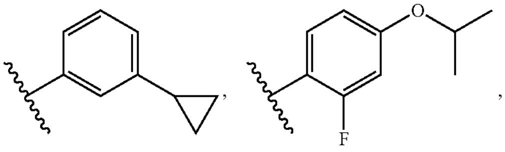, -continued

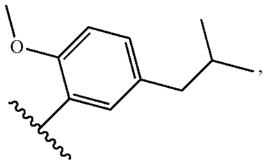
,
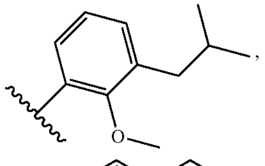
,
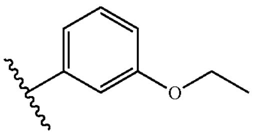
,
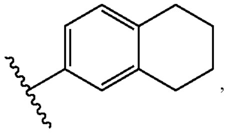
,
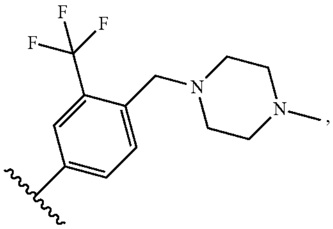
,
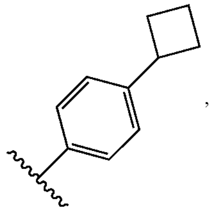
,
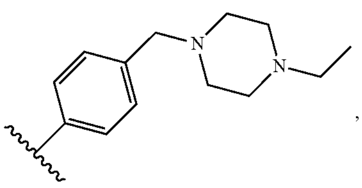
,
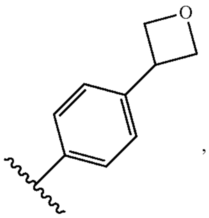
,
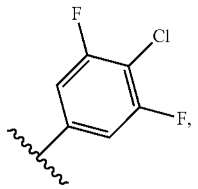

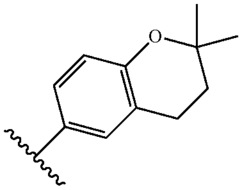
,
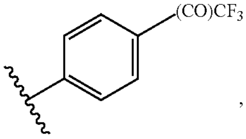
,
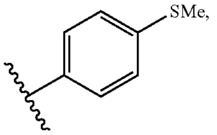

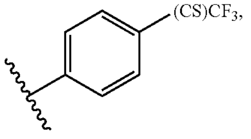

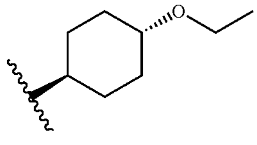
,
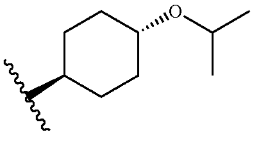
,
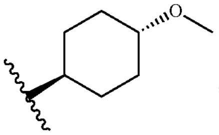
, and
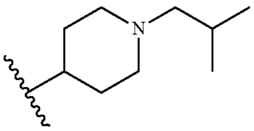
.

90. The compound or salt of any one of embodiments 1-34, wherein ring B comprises a phenyl, pyridinyl, pyrimidinyl, or naphthyl.

91. The compound or salt of embodiment 90, wherein ring B has a structure of:

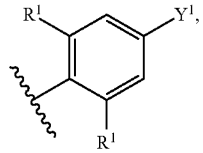

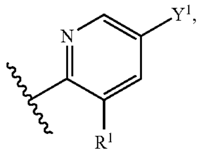

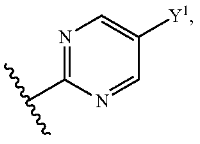
or
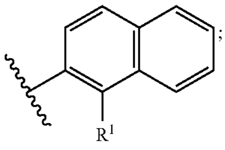

each $R^1$ is independently hydrogen, halogen, $C_1$-$C_6$alkyl, $C_3$-$C_6$cycloalkyl, $C_1$-$C_6$alkoxy, and $C_1$-$C_6$haloalkoxy; and $Y^1$ is independently selected from the group consisting of $C_1$-$C_3$alkyl, $C_3$-$C_6$cycloalkyl, $C_1$-$C_6$haloalkyl, $C_1$-$C_6$haloalkoxy, $C_1$-$C_6$alkoxy, and $C_3$-$C_6$cycloalkoxy.

92. The compound or salt of embodiment 91, wherein each $R^1$ is independently selected from the group consisting of H, D, fluoro, methyl, ethyl, and isopropyl.

93. The compound or salt of embodiment 91 or 92, wherein each $Y^1$ is independently selected from the group consisting of fluoromethyl, difluoromethyl, trifluoromethyl, trifluoromethoxy, pentafluoropropyl, isopropyl, isobutyl, cyclopropyl, 1,2-(difluoro)ethoxy, cyclopropyloxy, isopropoxy, ethoxy, and methoxy.

94. The compound or salt of embodiment 93, wherein $Y^1$ is isobutyl.

95. The compound or salt of any one of embodiments 1-93, wherein $X^1$ is N.

96. The compound or salt of any one of embodiments 1-93, wherein $X^1$ is $CR^1$.

97. The compound or salt of embodiment 96, wherein $R^1$ is H.

98. The compound or salt of embodiment 96, wherein $R^1$ is $C_1$-$C_3$alkyl.

99. The compound or salt of embodiment 98, wherein $R^1$ is methyl.

100. The compound or salt of any one of embodiments 1-99, wherein $X^2$ is NH.

101. The compound or salt of any one of embodiments 1-99, wherein $X^2$ is O.

102. The compound or salt of any one of embodiments 1-99, wherein $X^2$ is S.

103. The compound or salt of any one of embodiments 1-102, wherein Y is O.

104. The compound or salt of any one of embodiments 1-102, wherein Y is S.

105. The compound of embodiment 1 having a structure as recited in Table A.

106. A compound, or pharmaceutically acceptable salt thereof, having a structure as recited in Table B.

107. A pharmaceutical composition comprising the compound of any one of embodiments 1-106 and a pharmaceutically acceptable excipient.

108. A method of inhibiting cyclin dependent kinase 19 (CDK19) comprising contacting CDK19 with the compound or salt of any one of embodiments 1-106 or a compound, or pharmaceutically acceptable salt thereof, having a structure as recited in Table C in an amount effective to inhibit CDK19.

109. The method of embodiment 108, wherein the compound inhibits CDK19 selectively over cyclin dependent kinase 8 (CDK8).

110. The method of embodiment 109, wherein the compound is at least 2 times more selective for CDK19 over CDK8.

111. The method of embodiment 110, wherein the compound is at least 3 times more selective for CDK19 over CDK8.

112. The method of any one of embodiments 109-111, wherein the compound has an $IC_{50}$ for CDK19 of less than 400 nM.

113. The method of embodiment 112, wherein the compound has an $IC_{50}$ for CDK19 of less than 200 nM.

114. A method of treating cancer in a patient comprising administering to the patient a therapeutically effective amount of the compound or salt of any one of embodiments 1-106.

115. The method of embodiment 114, wherein the cancer is breast cancer, prostate cancer, cancer of the gastrointestinal tract (e.g., colorectal cancer), bladder cancer, sarcoma, cervical cancer, esophageal adenocarcinoma, acute myeloid leukemia, melanoma, glioma, or ovarian cancer.

116. The method of embodiment 115, wherein the cancer is breast cancer.

117. A method of treating breast cancer in a patient comprising administering to the patient a therapeutically effective amount of the compound or salt of any one of embodiments 1-106 or a compound, or pharmaceutically acceptable salt thereof, having a structure as recited in Table C.

118. The method of any one of embodiments 114-117, wherein the breast cancer is triple negative breast cancer.

119. The method of any one of embodiments 114-118, wherein the patient undergoes a second therapy.

120. The method of embodiment 119, further comprising removing breast tissue from the patient.

121. The method of any one of embodiments 114-120, further comprising administering a second therapeutic agent to the patient.

EXAMPLES

The following examples further illustrate the disclosed tablet formulation and process, but of course, should not be construed as in any way limiting its scope.

The following abbreviations are used in the Examples: TLC refers to thin layer chromatography; UV refers to ultraviolet; ACS refers to American Chemical Society; ESI refers to electrospray ionization; MS refers to mass spectrometry; LC refers to liquid chromatography; FRET refers to Förster resonant energy transfer; TNBC refers to triple negative breast cancer.

A library of approximately 100,000 compounds was screened for binding to CDK19 and/or CDK8 using a FRET-based displacement high-throughput assay resulting in the identification of 13 compounds having weak to moderate binding affinity to CDK19 and with moderate selectivity for CDK19 over CDK8. For example, a compound was identified having a CDK19 $IC_{50}$ of 330 nm and exhibited a 2-fold selectivity over CDK8 ($IC_{50}$ of 600 nm).

Additional compounds were prepared using one or both of Method A and Method B, as described herein, using the desired reagents that provide the desired compound.

General Chemical Synthesis: Reactions were performed under ambient atmosphere unless otherwise noted. Qualitative TLC analysis was performed on 250 mm thick, 60 Å, glass backed, F254 silica (Silicycle©, Quebec City, Canada). Visualization was accomplished with UV light and exposure to p-anisaldehyde or $KMnO_4$ stain solutions followed by heating. All solvents were ACS grade Sure/Seal™, and all other reagents were used as received unless otherwise noted. 2-Amino-5-(4-pyridinyl)-1,3,4-thiadiazole, 2-amino-5-(3-pyridinyl)-1,3,4-thiadiazole, 2-amino-5-(2-pyridinyl)-1,3,4-thiadiazole, 2-amino-5-(4-pyridinyl)-1,3-thiazole, 2-amino-5-(3-pyridinyl)-1,3-thiazole and 2-amino-5-(2-pyridinyl)-1,3-thiazole were sourced commercially. All isocyanates were purchased from commercial sources. Flash chromatography was performed on a Biotage Selekt purification system using silica gel flash cartridges (SiliCycle®, SiliaSep™ 40-63 μm, 60 Å). High performance liquid chromatography (HPLC) was performed on an Agilent 1260 Infinity preparative scale purification system using an Agilent PrepHT Zorbax Eclipse XDB-C18 reverse-phase column (21.2×250 mm). Structure determination was performed using 1H spectra that were recorded on a Bruker AV-500 spectrometer, and low-resolution mass spectra (ESI-MS) that were collected on a Shimadzu 20-20 ESI LCMS instrument. Structure determination was performed using 1H spectra that were recorded on either a Bruker AV-500 or AV-400 spectrometer, and low-resolution mass spectra (ESI-MS) that were collected on a Shimadzu 20-20 ESI LCMS instrument. Final compound purity was >95%, as determined by HPLC-MS. All final compound $^1H$ spectra were consistent with the expected structures.

FRET Displacement Assay to Measure $IC_{50}$: The CDK19/CDK8 $IC_{50}$ values were measured to evaluate activity and to determine CDK19/CDK8 selectivity. The $IC_{50}$ values of the disclosed compounds was measured using a LanthaScreen™ europium kinase binding assay (ThermoFisher), as described herein.

To a kinase buffer cocktail solution (e.g., 50 mM HEPES pH 7.5, 10 mM $MgCl_2$, 1 mM EGTA, 0.01% Brij-35) was added: purified recombinant his-tagged CDK19/CycC protein (5 nM), ATP-competitive kinase inhibitor scaffold kinase tracer Alexa Fluor® 665 (10 nM), biotin anti-his tag antibody (2 nM), LanthaScreen® europium-streptavidin (2 nM). An aliquot of the cocktail solution (10 μL) was added to each well of a LUMITRAC™ 200: 384 flat bottom, non-treated microtiter white plate. The plate was then covered to protect light sensitive reagents and incubated for 30 min at room temperature to equilibrate before addition of any inhibitors.

A serial dilution of the compounds was titrated into each well using an automated liquid handling Staccato integrated system at the following concentration(s) ($Log_{10}$ Molar [C]): −4.5, −5.0, −5.5, −6.0, −6.5, −7.0, −7.5, −8.0 so that a complete dose-response could be calculated. A Tecan microplate reader infinite m200 instrument was then used to measure the FRET signal of each individual well using an excitation of 317/20 nm, emission europium of 620/12 nm, and emission kinase tracer of 665/12 nm after a 3 h incubation period at room temperature until steady-state kinetics were achieved.

Results were performed in duplicate and were repeated a total of 3 independent times before data was normalized to the DMSO control group and $IC_{50}$ values reported. The results are summarized in Table 1.

The efficacy and selectivity of the disclosed compounds was evaluated in a TNBC cell line assay (MDA-MB-231), as was protein binding to human serum, and microsomal stability of the disclosed compounds, as described herein.

Triple-Negative Breast Cancer Cell Death Assay to Measure $LD_{50}$: Cells from a TNBC cell line (MDA-MB-231) and/or Human Foreskin Fibroblast 2088 (approximately 200,000 cells) were seeded into each well of a 6-welled polystyrene treated tissue culture plate and were allowed to attach for 18 h before treatment with compounds. The next day, cells were treated every 24 h with a fresh batch of media containing the test compound at one of the respective concentration(s) ($Log_{10}$ Molar [C]): −4.5, −5.0, −5.5, −6.0, −6.5, −7.0, −7.5, −8.0 so that a dose-response could be calculated. After 48 h of treatment, both adherent/non-adherent MDA-MB-231 cells were collected and stained with Trypan Blue (0.4%) solution at a 1:1 ratio. Live and dead cell counts were performed in triplicate for each condition using a Countess™ II Automated Cell Counter. $EC_{50}$ values represent the percentage of live cells after treatment, which was calculated after normalization to the DMSO only treated control group.

Lethal dose curves were then determined for both normal fibroblasts and MDA-MB-231 TNBC cells after treatment with various concentrations of either CDK8/19 dual inhibitor (CCT251921) or test compounds. Desirably, only treatment with CDK19-selective inhibitor (e.g., Compound A4) resulted in significant MDA-MB-231 cell death. Further, it was desirable that neither compound significantly killed the normal fibroblast cells.

CDK19 Overexpression Rescues Cell Death Phenotype After Inhibition: 200,000 MDA-MB-231 TNBC cells were seeded into each well of a 6-welled polystyrene treated tissue culture plate and were allowed to attach for 18 h before being transiently transfected with one of the following overexpression vectors containing the following protein sequence inserts: CDK8, CDK19, or CDK19-kinase dead (a4040c) mutant. Twenty four hours after transfection, cells were then subsequently treated for an additional 48 h with 2 μM of STF-00202062-001, a CDK19-selective inhibitor ($IC50_{CDK19}$≤2.5 nM; $IC50_{CDK8}$=126 nM). Live cells for each treatment group were quantified and normalized to the empty vector control and DMSO treated groups.

Triple-Negative Breast Cancer Patient Derived Organoid Experiment: TNBC patient derived tumor organoids were treated every 48 h with either DMSO solvent control (0.01% v/v), 2.5 μM CCT251921 (a CDK8/19 dual inhibitor), and/or 2.5 UM Compound A (CDK19-selective inhibitor) for a 14 day period. Representative images (2×) of green fluorescent protein tagged (GFP+) organoid cell populations were imaged and quantified. A significant decrease in both organoid frequency in addition to overall organoid size was observed. Cells were initially seeded at 5000/cells per well and the experiment was performed in triplicate. Organoids for each condition were then collected, dissociated, and digested into individual cells before being reseeded into new wells. No treatment was given to the cells but fresh media was administered every 48 h to simulate previous treatment conditions. After 14 days, representative images (2×) of GFP+organoid cell populations were imaged and quantified. A significant depletion of the stem cell population was observed as no treatment was re-administered yet organoids failed to regrow/form for cells treated with Compound A4 when compared to DMSO control and CCT251921 treated populations. Cells were approximately seeded at 1000/cells per well.

Microsome Assay to Measure Inhibitor Bioavailability: The bioavailability of the compounds was evaluated using a liver cell microsome assay commercially available from Cyprotex (Watertown, MA) (https://www.cyprotex.com/admepk/in-vitro-metabolism/microsomal-stability).

Inhibitor-Protein Binding Assay: The plasma binding of the compounds was evaluated using a plasma protein binding assay commercially available from Cyprotex (Watertown, MA) (https://www.cyprotex.com/admepk/protein-_binding/plasma-protein-binding).

The results of the biological assays are summarized in Table 2A and Table 2B.

Table 1 lists compounds and their $IC_{50}$ values illustrating the CDK19/CDK8 selectivity. The mass spectrometry data as available also is shown in Table 1.

TABLE 1

$IC_{50}$ and CDK19/CDK8 Selectivity

| Compound | CDK19 $IC_{50}$ (nm) | CDK8 $IC_{50}$ (nm) | CDK19 Selectivity | mass spec (m/z) |
|---|---|---|---|---|
| A49 | 240 | 560 | 2 | 332 [M − H] |
| A50 | 370 | 500 | 1 | 331 [M − H] |
| A119 | 260 | 510 | 2 | 629 [2M − H] |
| A120 | 360 | 700 | 2 | 296 [M − H] |
| A51 | | | | 332 [M − H] |
| A121 | 110 | 280 | 3 | 629 [2M − H] |
| A52 | 79 | 440 | 5 | 333 [M + H] |
| A53 | 7000 | 11000 | 2 | 312 [M + H] |
| A54 | 88 | 98 | 1 | 372 [M − H] |
| A122 | 30 | 49 | 2 | 797 [2M − H] |
| B61 | 130 | 270 | 2 | 683 [2M − H] |
| A123 | 38 | 153 | 4 | 326 [M − H] |
| A55 | 34 | 56 | 2 | 864 [2M − H] |
| B64 | 301 | 191 | <1 | 737 [2M − H] |
| A56 | 311 | 271 | <1 | 386 [M − H] |
| A3 | 4 | 53 | 13 | 761 [2M − H] |
| A57 | | | | 402 [M − H] |
| A58 | ≤2.5 | 14 | ≥6 | 324 [M − H] |
| A5 | 7 | 94 | 14 | 352 [M − H] |
| B68 | 271 | 424 | 2 | 757 [2M − H] |
| B69 | 10 | 25 | 2.5 | 761 [2M − H] |
| A59 | ≤2.5 | 9.4 | ≥4 | 725 [2M − H] |
| B71 | | | | 789 [2M − H] |
| B72 | 46 | 103 | 2 | 759 [2M − H] |
| A60 | 146 | 256 | 2 | 681 [2M − H] |
| A61 | 39 | 91 | 2 | 819 [2M − H] |
| A62 | ≤2.5 | 19.4 | ≥8 | 725 [2M − H] |
| A124 | ≤2.5 | 21 | ≥8 | 705 [2M − H] |
| A125 | 42 | 35 | 1 | 621 [2M − H] |
| A63 | ≤2.5 | | ≥1 | 324 [M − H] |
| A64 | ≤2.5 | 23 | ≥9 | 677 [2M − H] |
| A65 | 47 | 13 | <1 | 729 [2M − H] |
| A66 | | 2200 | <1 | 297 [M − H] |
| B82 | 13 | 50 | 4 | 685 [2M − H] |
| A67 | 23 | 31 | <1 | 783 [2M − H] |
| A68 | 24 | 119 | 5 | 340 [M − H] |
| A69 | ≤2.5 | 4 | ≥2 | 673 [2M − H] |
| A70 | ≤2.5 | 19 | ≥8 | 338 [M − H] |
| A1 | ≤2.5 | 82 | ≥33 | 352 [M − H] |
| A72 | 1600 | 603 | <1 | 755 [2M − H] |
| B89 | ≤2.5 | 8 | ≥3 | 793 [2M − H] |
| B80 | 70 | 76 | 1 | 376 [M − H] |
| A73 | | | | 360 [M − H] |
| A74 | | | | 665 [2M − H] |
| B95 | | | | 298 [M − H] |
| A75 | 2300 | 706 | <1 | 370 [M − H] |
| A76 | | | | 380 [M − H] |
| B97 | | | | 298 [M − H] |
| A4 | ≤2.5 | 126 | ≥50 | 825 [2M − H] |
| A2 | ≤2.5 | 80 | ≥32 | 351 [M − H] |
| A77 | 2500 | 37 | <1 | 345 [M − H] |
| A78 | 34 | 133 | 4 | 823 [2M − H] |
| A79 | 64 | 93 | 2 | 441 [M − H] |
| A80 | 74 | 80 | 1 | 354 [M − H] |
| A81 | 66 | 471 | 7 | 396 [M − H] |
| A82 | 22 | 63 | 3 | 297 [M − H] |
| A83 | 301 | 79 | <1 | 425 [M − H] |
| A84 | 24 | 50 | 2 | 365 [M − H] |
| A85 | | | | 336 [M + H] |
| A86 | | | | 336 [M − H] |
| A87 | | | | 394 [M − H] |
| A88 | | | | 395 [M − H] |
| A89 | | | | 335 [M − H] |
| A90 | | | | 396 [M + H] |
| A91 | 443 | 579 | 1 | 469 [M − H] |

TABLE 1-continued

| $IC_{50}$ and CDK19/CDK8 Selectivity | | | | |
|---|---|---|---|---|
| Compound | CDK19 $IC_{50}$ (nm) | CDK8 $IC_{50}$ (nm) | CDK19 Selectivity | mass spec (m/z) |
| A92 | 2000 | 2600 | 1 | 378 [M − H] |
| A93 | 60 | 126 | 2 | 412 [M − H] |
| A94 | 781 | 2100 | 3 | 420 [M − H] |
| A95 | 1200 | 2200 | 2 | 405 [M − H] |
| A96 | 416 | 441 | 1 | 448 [M − H] |
| A97 | 247 | 148 | <1 | 510 [M − H] |
| A98 | 186 | 134 | <1 | 496 [M − H] |
| A126 | 3 | 77 | 26 | 332 [M + H] |
| A127 | 69 | 121 | 2 | 342 [M + H] |
| A99 | ≤2.5 | 28 | ≥11 | 340 [M + H] |
| A100 | ≤2.5 | 43 | ≥17 | 354 [M + H] |
| A101 | ≤2.5 | 20 | ≥8 | 348 [M + H] |
| A102 | 35 | 134 | 4 | 356 [M + H] |
| A103 | 4 | 65 | 19 | 330 [M + H] |
| A104 | 56 | 78 | 1 | 342 [M + H] |
| A105 | ≤2.5 | 63 | ≥25 | 376 [M + H] |
| A106 | ≤2.5 | 38 | ≥15 | 368 [M + H] |
| A107 | 22 | 62 | 2.8 | 372 [M + H] |
| A108 | 37 | 65 | 2 | 354 [M + H] |
| A109 | ≤2.5 | 66 | ≥26 | 388 [M + H] |
| A110 | 1.3 | 64 | 49 | 384 [M + H] |
| A111 | ≤2.5 | 77 | ≥31 | 350 [M + H] |
| A112 | 31 | 50 | 2 | 379 [M + H] |
| A113 | 40 | 270 | 6.8 | 368 [M + H] |
| A114 | 19 | 57 | 3 | 355 [M + H] |
| A115 | ≤2.5 | 54 | ≥22 | 354 [M + H] |
| A116 | 355 | 426 | 1 | 411 [M + H] |
| A117 | 430 | 200 | <1 | 339 [M + H] |
| A118 | ≤2.5 | 27 | ≥3 | 363 [M + H] |
| A119 | 158 | 195 | 1 | 363 [M + H] |
| A120 | 317 | 638 | 2 | 347 [M + H] |
| A121 | 271 | 424 | 2 | 380 [M + H] |
| A122 | 10 | 25 | 2.5 | 382 [M + H] |
| A123 | | | | 396 [M + H] |
| A124 | 46 | 103 | 2 | 381 [M + H] |
| A125 | ≤2.5 | 8 | ≥3 | 398 [M + H] |
| A126 | 853 | 1700 | 2 | 323 [M + H] |
| A127 | 455 | 482 | 1 | 297 [M + H] |
| A128 | 194 | 300 | 2 | 619 [M + H] |
| A129 | 148 | 201 | 1 | 559 [M + H] |
| A130 | | | | 513 [M + H] |
| A131 | 92.2 | 757 | 8 | 513 [M + H] |
| A132 | | | | 513 [M + H] |
| A133 | ≤2.5 | 52 | ≥21 | 340 [M + H] |
| A134 | 1500 | 1000 | <1 | 395 [M + H] |
| A135 | | | | 353 [M + H] |
| A136 | 9400 | 28400 | 3 | 337 [M + H] |
| A137 | | | | 367 [M + H] |
| A138 | 2600 | 3200 | 1 | 381 [M + H] |
| A139 | 9.3 | 153 | 17 | 374 [M + H] |
| A140 | 154 | 176 | 1 | 384 [M + H] |
| A141 | 351 | 593 | 2 | 384 [M + H] |
| A142 | 70 | 106 | 2 | 354 [M + H] |
| A143 | 206 | 150 | <1 | 342 [M + H] |
| A144 | 31 | 4 | <1 | 384 [M + H] |
| A145 | ≤2.5 | 33 | ≥13 | 352 [M + H] |
| A146 | ≤2.2 | 23 | ≥11 | 478 [M + H] |
| A147 | ≤2.5 | 45 | ≥18 | 352 [M + H] |
| A148 | 1175 | 1306 | 1 | 424 [M + H] |
| A149 | 85 | 186 | 2 | 354 [M + H] |
| A150 | 24 | 39 | 2 | 368 [M + H] |
| A151 | 32 | 82 | 3 | 384 [M + H] |
| A152 | 27 | 88 | 3 | 368 [M + H] |
| A153 | 49 | 75 | 2 | 432 [M + H] |
| A154 | | | | |
| A155 | 83 | 122 | 1 | 368 [M + H] |
| A156 | ≤2.5 | ≤2.5 | 1 | 382 [M + H] |

TABLE 2A

| Results from MDA-MB-231 Cell Assay | | | | | |
|---|---|---|---|---|---|
| Compound | $EC_{50}$[1a] (nm) | $EC_{50}$[1b] (nm) | Caco2[2] | Efflux Ratio | Caco2[3] |
| A52 | — | | 8.03 | 1.10 | 2.30 |
| A3 | 2700 | 2600 | 0.129 | 3.30 | 0.338 |
| A5 | 6400 | 17000 | X | X | X |
| A1 | 1460 | X | 0.277 | 1.10 | 0.387 |
| A4 | 1100 | N/D | 1.63 | 9.50 | 15.4 |
| A2 | 1170 | X | 7.51 | −4.34 | 0.173 |
| A81 | X | X | 12.2 | 2.20 | 7.58 |

[1a]$EC_{50}$ measured in MDA-MB-231 TNBC cells

[1b]$EC_{50}$ measured in human fibroblast cells (control)

[2]cell permeability measured in Caco2 cell assay; (A-B Papp × $10^{-6}$ cm/s)

[3]cell permeability measured in Caco2 + elacridar assay; (A-B Papp × $10^{-6}$ cm/s)

TABLE 2B

| Results from MDA-MB-231 Cell Assay | | | | |
|---|---|---|---|---|
| Compound | Microsome Stability[1a] | Microsome Stability[1b] | Protein Binding[2a] | Protein Binding[2b] |
| A52 | 10.3 | 91.1 | X | X |
| A3 | 3.70 | 8.30 | X | X |
| A5 | X | X | X | X |
| A1 | 6.1 | 12.4 | X | X |
| A4 | 1 | 18.4 | 99.7 | 99.3 |
| A2 | 2.8 | 3.1 | 99.6 | 99.2 |
| A81 | X | X | 99.5 | 97.4 |

[1a]human microsome;

[1b]mouse microsome;

[2a]human microsome;

[2b]mouse microsome

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (for example, "such as") provided herein, is intended merely to better illuminate the invention and does not pose a limitation on the scope of the invention unless otherwise claimed. No language in the specification should be construed as indicating any non-claimed element as essential to the practice of the invention.

What is claimed:
1. A compound having a structure as recited in Table A:
TABLE A
| ID | Structure |
|---|---|
| A1 | 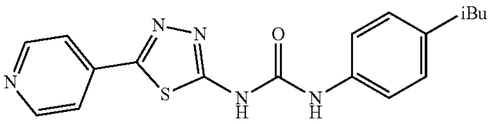 |
| A3 | 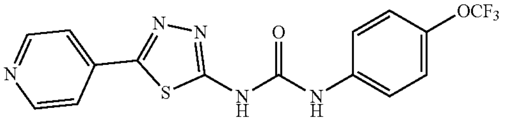 [SMILES: O=C(Nc1ccc(OC(F)(F)F)cc1)Nc1nnc(-c2ccncc2)s1] |
| A4 | 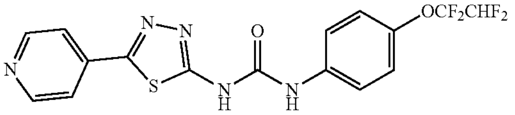 |
| A5 | 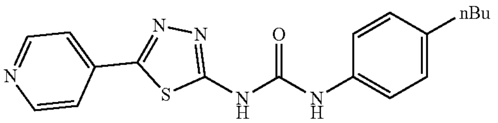 |
| A6 | 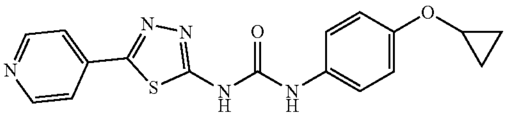 [SMILES: O=C(Nc1ccc(OC2CC2)cc1)Nc1nnc(-c2ccncc2)s1] |
| A7 | 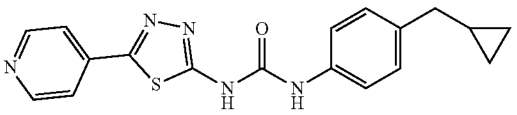 [SMILES: O=C(Nc1ccc(CC2CC2)cc1)Nc1nnc(-c2ccncc2)s1] |
| A8 | 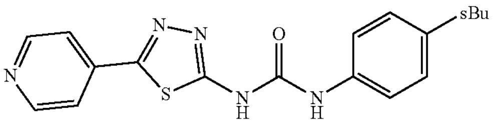 |
| A9 | 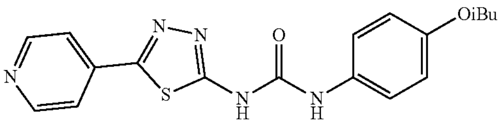 |
| A10 | 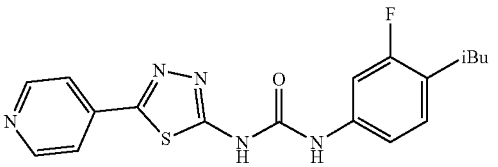 |
| A11 | 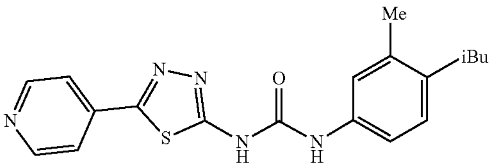 |
TABLE A-continued
| ID | Structure |
|---|---|
| A12 | 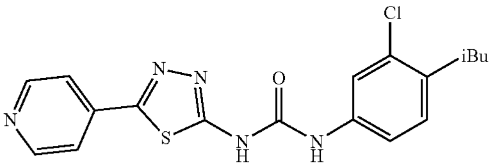 |
| A13 | 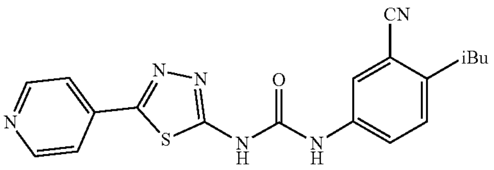 |
| A14 | 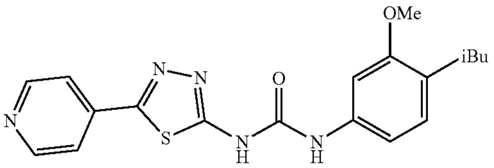 |
| A15 | 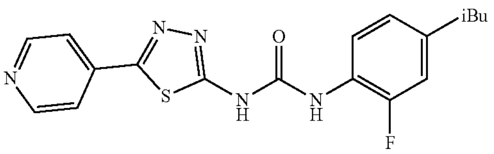 |
| A16 | 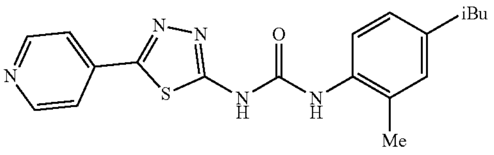 |
| A17 | 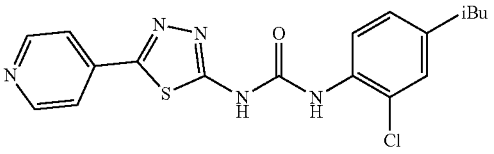 |
| A18 | 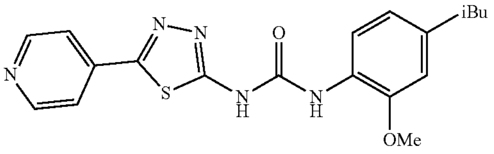 |
| A19 | 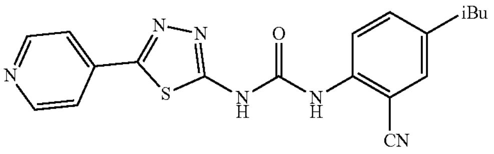 |
| A25 | 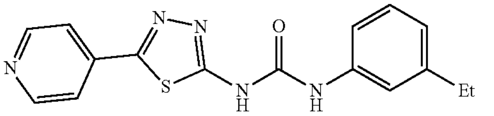 [SMILES: CCc1cccc(NC(=O)Nc2nnc(-c3ccncc3)s2)c1] |
| A26 | 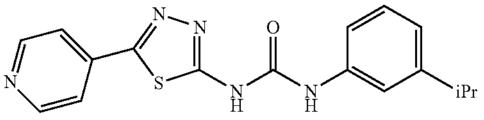 [SMILES: CC(C)c1cccc(NC(=O)Nc2nnc(-c3ccncc3)s2)c1] |

TABLE A-continued
| ID | Structure |
|---|---|
| A27 | 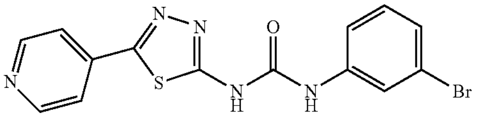 [SMILES: O=C(Nc1cccc(Br)c1)Nc1nnc(-c2ccncc2)s1] |
| A28 | 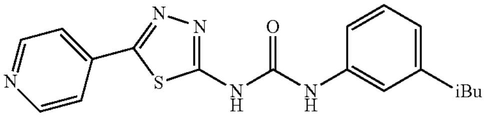 |
| A29 | 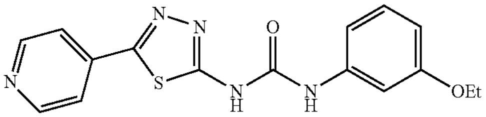 [SMILES: CCOc1cccc(NC(=O)Nc2nnc(-c3ccncc3)s2)c1] |
| A30 | 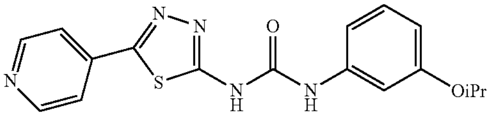 [SMILES: CC(C)Oc1cccc(NC(=O)Nc2nnc(-c3ccncc3)s2)c1] |
| A31 | 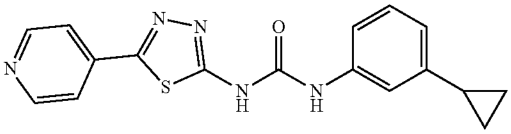 [SMILES: O=C(Nc1cccc(C2CC2)c1)Nc1nnc(-c2ccncc2)s1] |
| A32 | 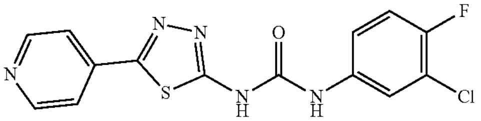 [SMILES: O=C(Nc1ccc(F)c(Cl)c1)Nc1nnc(-c2ccncc2)s1] |
| A33 | 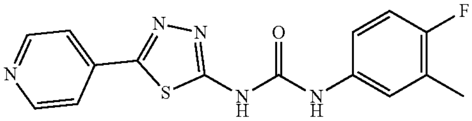 [SMILES: Cc1cc(NC(=O)Nc2nnc(-c3ccncc3)s2)ccc1F] |
| A39 | 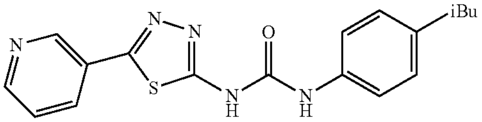 |
| A49 | 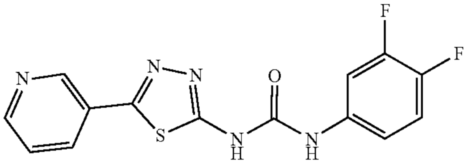 [SMILES: O=C(Nc1ccc(F)c(F)c1)Nc1nnc(-c2cccnc2)s1] |
| A54 | 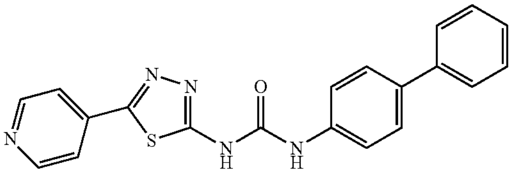 [SMILES: O=C(Nc1ccc(-c2ccccc2)cc1)Nc1nnc(-c2ccncc2)s1] |
TABLE A-continued
| ID | Structure |
|---|---|
| A55 | 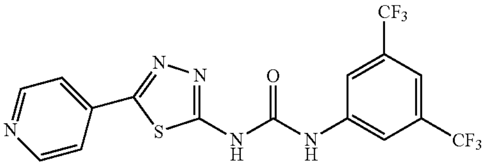 [SMILES: O=C(Nc1cc(C(F)(F)F)cc(C(F)(F)F)c1)Nc1nnc(-c2ccncc2)s1] |
| A56 | 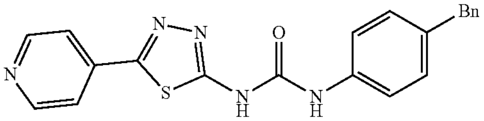 [SMILES: O=C(Nc1ccc(Cc2ccccc2)cc1)Nc1nnc(-c2ccncc2)s1] |
| A57 | 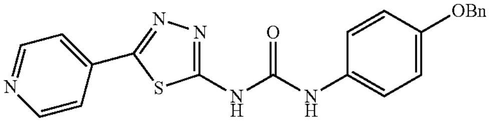 [SMILES: O=C(Nc1ccc(OCc2ccccc2)cc1)Nc1nnc(-c2ccncc2)s1] |
| A58 | 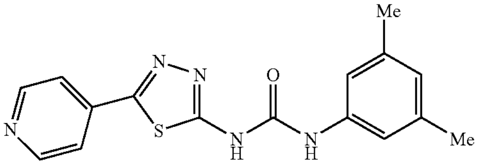 [SMILES: Cc1cc(C)cc(NC(=O)Nc2nnc(-c3ccncc3)s2)c1] |
| A59 | 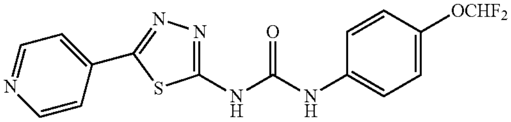 [SMILES: O=C(Nc1ccc(OC(F)F)cc1)Nc1nnc(-c2ccncc2)s1] |
| A60 | 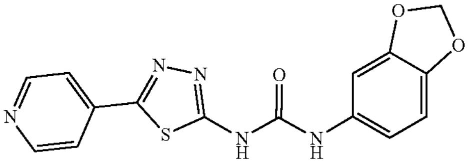 [SMILES: O=C(Nc1ccc2c(c1)OCO2)Nc1nnc(-c2ccncc2)s1] |
| A62 | 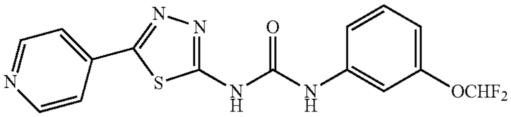 [SMILES: O=C(Nc1cccc(OC(F)F)c1)Nc1nnc(-c2ccncc2)s1] |
| A63 | 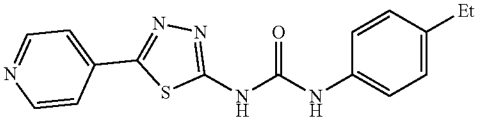 [SMILES: CCc1ccc(NC(=O)Nc2nnc(-c3ccncc3)s2)cc1] |
| A64 | 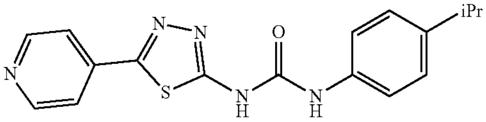 [SMILES: CC(C)c1ccc(NC(=O)Nc2nnc(-c3ccncc3)s2)cc1] |
| A65 | 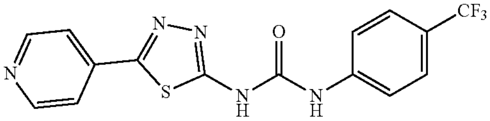 [SMILES: O=C(Nc1ccc(C(F)(F)F)cc1)Nc1nnc(-c2ccncc2)s1] |
| A68 | 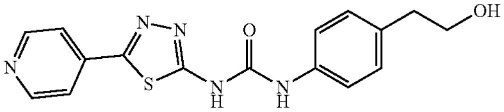 [SMILES: O=C(Nc1ccc(CCO)cc1)Nc1nnc(-c2ccncc2)s1] |

TABLE A-continued
| ID | Structure |
|---|---|
| A69 | 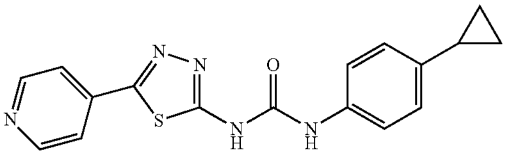 [SMILES: O=C(Nc1ccc(C2CC2)cc1)Nc1nnc(-c2ccncc2)s1] |
| A70 | 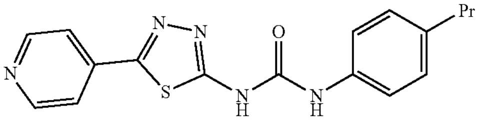 |
| A72 | 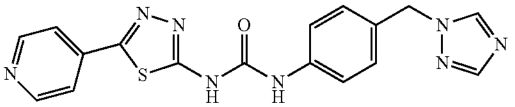 [SMILES: O=C(Nc1ccc(Cn2cncn2)cc1)Nc1nnc(-c2ccncc2)s1] |
| A74 | 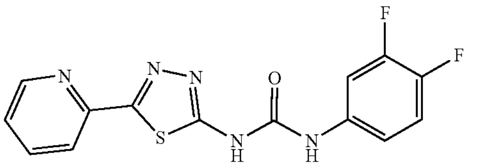 [SMILES: O=C(Nc1ccc(F)c(F)c1)Nc1nnc(-c2ccccn2)s1] |
| A75 | 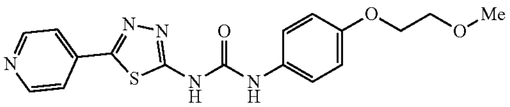 [SMILES: COCCOc1ccc(NC(=O)Nc2nnc(-c3ccncc3)s2)cc1] |
| A80 | 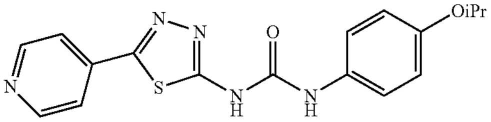 |
| A93 | 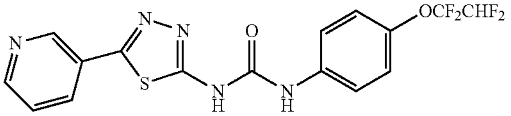 |
| A99 | 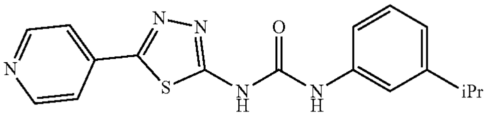 [SMILES: CC(C)c1cccc(NC(=O)Nc2nnc(-c3ccncc3)s2)c1] |
| A100 | 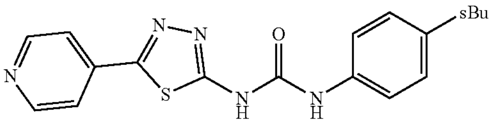 |
| A101 | 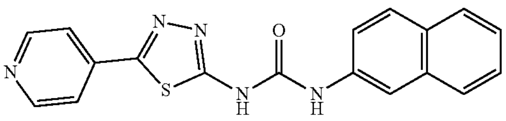 [SMILES: O=C(Nc1ccc2ccccc2c1)Nc1nnc(-c2ccncc2)s1] |
| A102 | 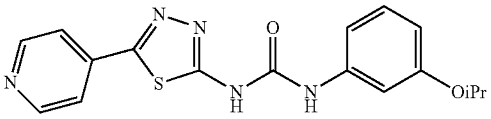 [SMILES: CC(C)Oc1cccc(NC(=O)Nc2nnc(-c3ccncc3)s2)c1] |
TABLE A-continued
| ID | Structure |
|---|---|
| A104 | 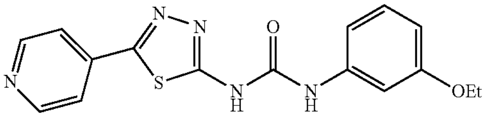 [SMILES: CCOc1cccc(NC(=O)Nc2nnc(-c3ccncc3)s2)c1] |
| A106 | 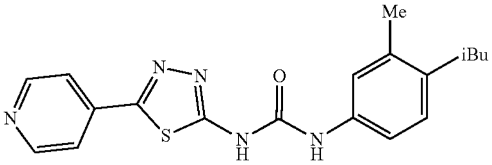 |
| A107 | 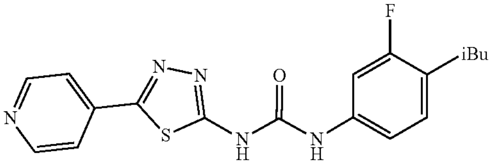 |
| A108 | 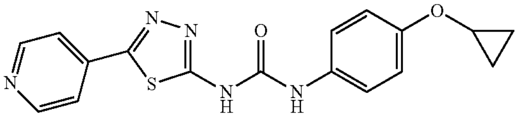 [SMILES: O=C(Nc1ccc(OC2CC2)cc1)Nc1nnc(-c2ccncc2)s1] |
| A109 | 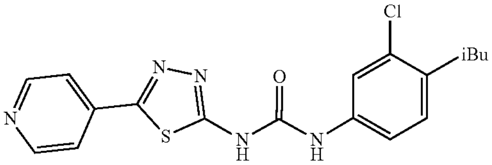 |
| A110 | 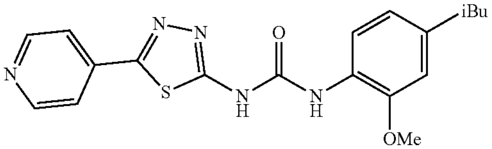 |
| A111 | 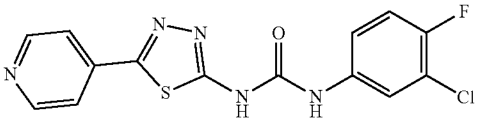 [SMILES: O=C(Nc1ccc(F)c(Cl)c1)Nc1nnc(-c2ccncc2)s1] |
| A112 | 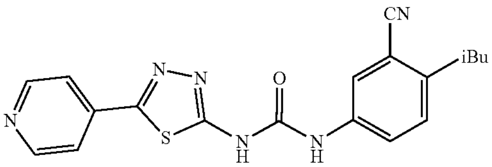 |
| A113 | 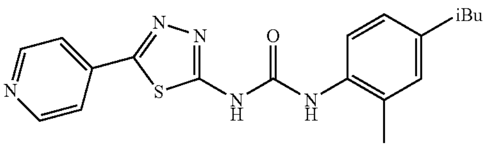 |
| A114 | 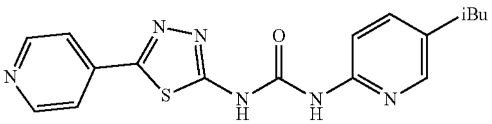 |

TABLE A-continued
| ID | Structure |
|---|---|
| A115 | 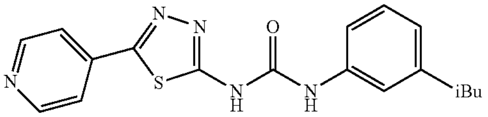 |
| A116 | 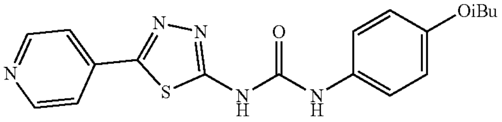 |
| A122 | 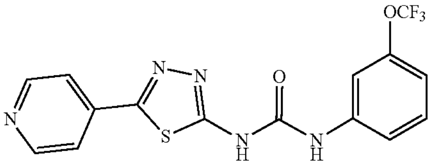 [SMILES: O=C(Nc1cccc(OC(F)(F)F)c1)Nc1nnc(-c2ccncc2)s1] |
| A123 | 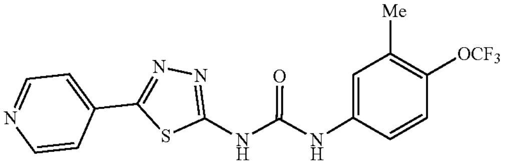 [SMILES: Cc1cc(NC(=O)Nc2nnc(-c3ccncc3)s2)ccc1OC(F)(F)F] |
| A125 | 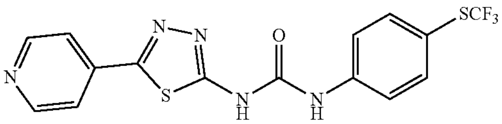 |
| A133 | 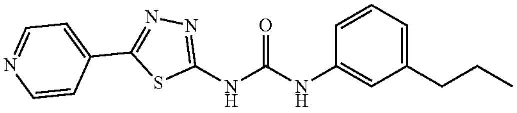 [SMILES: CCCc1cccc(NC(=O)Nc2nnc(-c3ccncc3)s2)c1] |
| A139 | 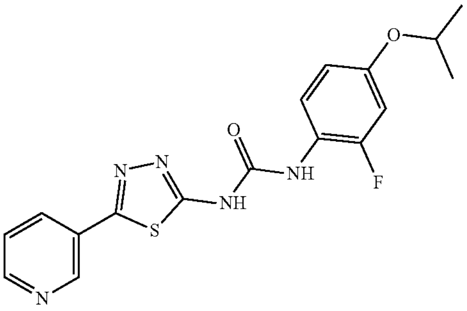 [SMILES: CC(C)Oc1ccc(NC(=O)Nc2nnc(-c3cccnc3)s2)c(F)c1] |
| A140 | 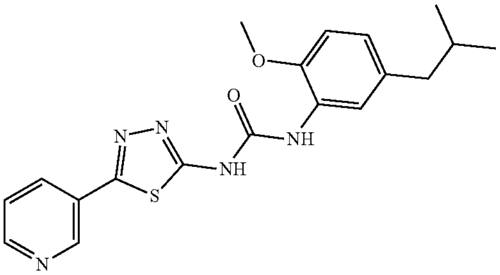 [SMILES: COc1ccc(CC(C)C)cc1NC(=O)Nc1nnc(-c2cccnc2)s1] |
TABLE A-continued
| ID | Structure |
|---|---|
| A141 | 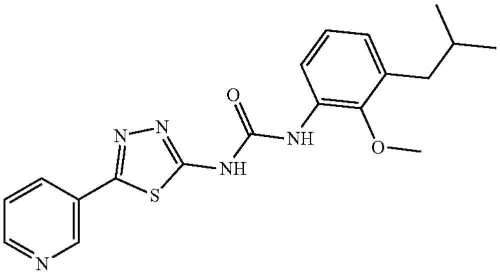 [SMILES: COc1c(CC(C)C)cccc1NC(=O)Nc1nnc(-c2cccnc2)s1] |
| A142 | 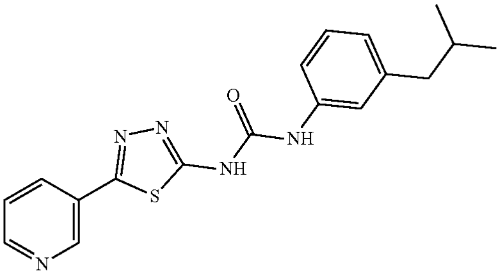 [SMILES: CC(C)Cc1cccc(NC(=O)Nc2nnc(-c3cccnc3)s2)c1] |
| A143 | 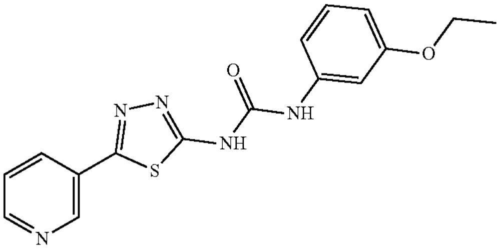 [SMILES: CCOc1cccc(NC(=O)Nc2nnc(-c3cccnc3)s2)c1] |
| A144 | 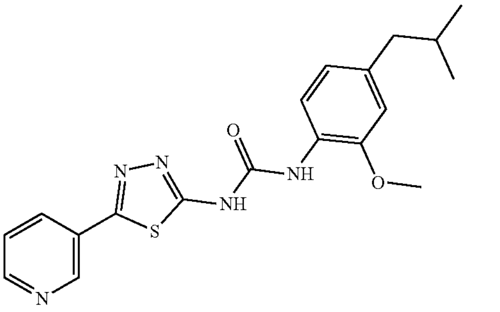 [SMILES: COc1cc(CC(C)C)ccc1NC(=O)Nc1nnc(-c2cccnc2)s1] |
| A146 | 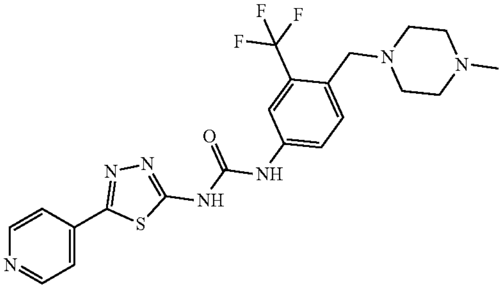 [SMILES: CN1CCN(Cc2ccc(NC(=O)Nc3nnc(-c4ccncc4)s3)cc2C(F)(F)F)CC1] |

TABLE A-continued
| ID | Structure |
|---|---|
| A147 | 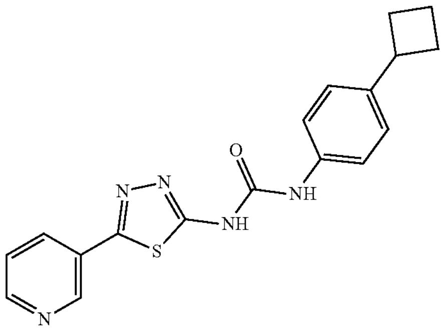 [SMILES: O=C(Nc1ccc(C2CCC2)cc1)Nc1nnc(-c2cccnc2)s1] |
| A148 | 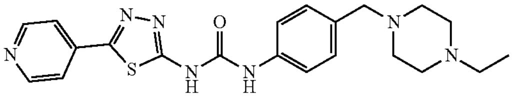 [SMILES: CCN1CCN(Cc2ccc(NC(=O)Nc3nnc(-c4ccncc4)s3)cc2)CC1] |
TABLE A-continued
| ID | Structure |
|---|---|
| A149 | 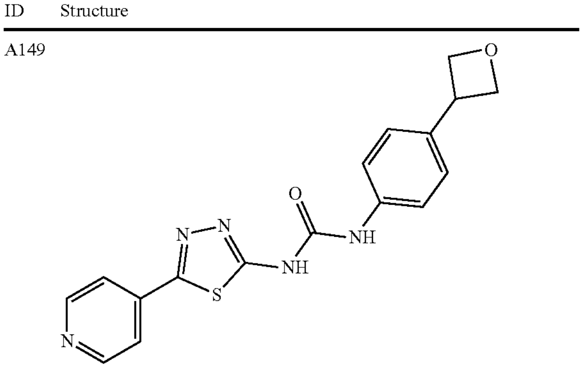 |
| A152 | 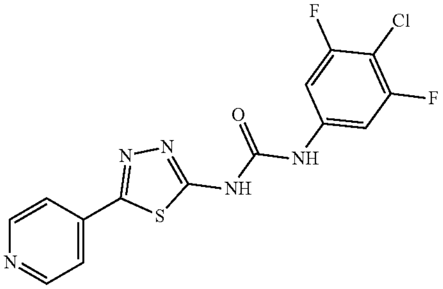 [SMILES: O=C(Nc1cc(F)c(Cl)c(F)c1)Nc1nnc(-c2ccncc2)s1] |
* * * * *